US011274307B2

(12) United States Patent
Erickson et al.

(10) Patent No.: US 11,274,307 B2
(45) Date of Patent: Mar. 15, 2022

(54) COMPOSITIONS AND METHODS FOR INHIBITING FACTOR D

(71) Applicant: 396419 B.C. Ltd., Victoria (CA)

(72) Inventors: Carl Erickson, Corte Madera, CA (US); Christopher P. Rusconi, Durham, NC (US); Kevin G. McLure, Oakland, CA (US)

(73) Assignee: 396419 B.C. Ltd., Victoria (CA)

( * ) Notice: Subject to any disclaimer, the term of this patent is extended or adjusted under 35 U.S.C. 154(b) by 0 days.

(21) Appl. No.: 16/742,741

(22) Filed: Jan. 14, 2020

(65) Prior Publication Data

US 2020/0392502 A1    Dec. 17, 2020

Related U.S. Application Data

(60) Continuation of application No. 16/121,458, filed on Sep. 4, 2018, now abandoned, which is a division of application No. 15/693,361, filed on Aug. 31, 2017, now Pat. No. 10,174,325, which is a continuation of application No. PCT/US2017/014458, filed on Jan. 20, 2017.

(60) Provisional application No. 62/297,095, filed on Feb. 18, 2016, provisional application No. 62/281,092, filed on Jan. 20, 2016.

(51) Int. Cl.
*C12N 15/115* (2010.01)
*A61K 31/7105* (2006.01)

(52) U.S. Cl.
CPC ........ *C12N 15/115* (2013.01); *A61K 31/7105* (2013.01); *C12N 2310/16* (2013.01)

(58) Field of Classification Search
None
See application file for complete search history.

(56) References Cited

U.S. PATENT DOCUMENTS

| | | | |
|---|---|---|---|
| 5,270,163 A | 12/1993 | Gold et al. | |
| 5,475,096 A | 12/1995 | Gold et al. | |
| 6,140,490 A | 10/2000 | Biesecker et al. | |
| 6,333,034 B1 | 12/2001 | Gupta-Bansal et al. | |
| 6,653,340 B1 | 11/2003 | Babu et al. | |
| 6,956,107 B2 | 10/2005 | Fung et al. | |
| 7,112,327 B2 | 9/2006 | Fung et al. | |
| 7,927,592 B2 | 4/2011 | Fung et al. | |
| 7,943,135 B2 | 5/2011 | Fung et al. | |
| 7,999,082 B2 | 8/2011 | Holers et al. | |
| 8,007,791 B2 | 8/2011 | Hass et al. | |
| 8,067,002 B2 | 11/2011 | An et al. | |
| 8,124,090 B2 | 2/2012 | Fung et al. | |
| 8,273,352 B2 | 9/2012 | Huang et al. | |
| 8,435,512 B2 | 5/2013 | Bansal et al. | |
| 8,492,082 B2 | 7/2013 | De et al. | |
| 8,580,735 B2 | 11/2013 | Francois et al. | |
| 8,664,362 B2 | 3/2014 | Bansal | |
| 8,703,136 B2 | 4/2014 | Baas et al. | |
| 8,753,625 B2 | 6/2014 | Fung et al. | |
| 8,858,943 B2 | 10/2014 | Burbidge et al. | |
| 8,911,733 B2 | 12/2014 | Holers et al. | |
| 8,921,523 B2 | 12/2014 | Alard et al. | |
| 8,940,299 B2 | 1/2015 | Medof et al. | |
| 8,981,060 B2 | 3/2015 | Bansal | |
| 9,066,925 B2 | 6/2015 | Tomlinson et al. | |
| 9,085,555 B2 | 7/2015 | Altmann et al. | |
| 9,278,108 B2 | 3/2016 | Takenaka et al. | |
| 9,803,194 B2 | 10/2017 | May et al. | |
| 9,873,727 B2 | 1/2018 | Sullenger et al. | |
| 10,174,325 B2 | 1/2019 | Erickson et al. | |
| 10,308,943 B2 | 6/2019 | Erickson et al. | |
| 10,428,330 B2 | 10/2019 | Erickson et al. | |
| 2004/0038869 A1 | 2/2004 | Finney et al. | |
| 2007/0065433 A1 | 3/2007 | Mollnes et al. | |
| 2007/0093443 A1 | 4/2007 | Madison et al. | |
| 2007/0149616 A1 | 6/2007 | Clark et al. | |
| 2007/0178068 A1 | 8/2007 | Reich et al. | |
| 2007/0196367 A1 | 8/2007 | Dinu | |
| 2008/0269318 A1 | 10/2008 | Romano | |
| 2009/0092980 A1 | 4/2009 | Arenz et al. | |
| 2009/0117171 A1 | 5/2009 | Francois et al. | |
| 2009/0269356 A1 | 10/2009 | Epstein et al. | |
| 2011/0044983 A1 | 2/2011 | Lambris et al. | |
| 2011/0060027 A1 | 3/2011 | Benedict et al. | |
| 2011/0160636 A1 | 6/2011 | Bansal | |
| 2011/0165648 A1 | 7/2011 | Campagne et al. | |
| 2011/0190221 A1 | 8/2011 | Francois et al. | |
| 2012/0087905 A1 | 4/2012 | Lachmann | |

(Continued)

FOREIGN PATENT DOCUMENTS

| JP | 5825673 B2 | 12/2015 |
|---|---|---|
| WO | WO-9119813 A1 | 12/1991 |

(Continued)

OTHER PUBLICATIONS

Altschul, et al. Basic local alignment search tool. J Mol Biol. Oct. 5, 1990;215(3):403-10.

Altschul, et al. Gapped BLAST and PSI-BLAST: a new generation of protein database search programs. Nucleic Acids Res. Sep. 1, 1997;25(17):3389-402.

Ambati et al. Immunology of age-related macular degeneration. Nature Reviews Immunology 13(6):438-451 (May 24, 2013). DOI: 10.1038/nri3459.

Berchuck, et al. All-trans-retinal sensitizes human RPE cells to alternative complement pathway-induced cell death. Invest Ophthalmol Vis Sci. Apr. 12, 2013;54(4):2669-77.

(Continued)

*Primary Examiner* — Brian Whiteman

(74) *Attorney, Agent, or Firm* — Wilson Sonsini Goodrich & Rosati

(57) ABSTRACT

The application discloses methods and compositions for the inhibition of the alternative complement pathway. The methods and compositions involve the use of aptamers for inhibiting complement Factor D. The application further provides anti-Factor D aptamers for the treatment of dry age-related macular degeneration, geographic atrophy, wet age-related macular degeneration or Stargardt disease.

17 Claims, 16 Drawing Sheets

Specification includes a Sequence Listing.

(56) References Cited

U.S. PATENT DOCUMENTS

| | | | |
|---|---|---|---|
| 2012/0107315 | A1 | 5/2012 | Behrens et al. |
| 2012/0190578 | A1 | 7/2012 | Seddon et al. |
| 2013/0035388 | A1 | 2/2013 | Mcgeer et al. |
| 2013/0237589 | A1 | 9/2013 | Benedict et al. |
| 2014/0235701 | A1 | 8/2014 | Jin et al. |
| 2014/0371133 | A1 | 12/2014 | Francois et al. |
| 2015/0044205 | A1 | 2/2015 | Yaspan et al. |
| 2015/0104445 | A1 | 4/2015 | Uknis et al. |
| 2015/0239837 | A1 | 8/2015 | Wiles et al. |
| 2016/0061840 | A1 | 3/2016 | Lee et al. |
| 2017/0328909 | A1 | 11/2017 | Bock et al. |
| 2018/0030446 | A1 | 2/2018 | Benedict et al. |
| 2018/0051287 | A1 | 2/2018 | Erickson et al. |
| 2019/0010499 | A1 | 1/2019 | Erickson et al. |
| 2019/0161755 | A1 | 5/2019 | Erickson et al. |

FOREIGN PATENT DOCUMENTS

| | | | |
|---|---|---|---|
| WO | WO-9927133 | A1 | 6/1999 |
| WO | WO-2007084765 | A2 | 7/2007 |
| WO | WO-2007103549 | A2 | 9/2007 |
| WO | WO-2012178083 | A1 | 12/2012 |
| WO | WO-2015168468 | A1 | 11/2015 |
| WO | WO-2017087919 | A1 | 5/2017 |
| WO | WO-2017127761 | A1 | 7/2017 |
| WO | WO-2018136827 | A1 | 7/2018 |
| WO | WO-2018136831 | A1 | 7/2018 |
| WO | WO-2019022986 | A1 | 1/2019 |

OTHER PUBLICATIONS

Co-pending U.S. Appl. No. 16/514,628, filed Jul. 17, 2019.
Co-pending U.S. Appl. No. 16/541,482, filed Aug. 15, 2019.
Del Amo et al. Intravitreal clearance and volume of distribution of compounds in rabbits: In silico prediction and pharmacokinetic simulations for drug development. Eur J Pharm Biopharm 95(Pt B):215-226 (Sep. 2015). Epub Jan. 17, 2015. doi: 10.1016/j.ejpb.2015.01.003 . . . .
EP17742071.8 Extended European Search Report dated Aug. 12, 2019.
Forneris et al. Chapter 630: Complement Factor D. Handbook of Proteolytic Enzymes. vol. 3, pp. 2841-2848 (2013).
Forneris, et al. Structures of C3b in complex with factors B and D give insight into complement convertase formation. Science. Dec. 24, 2010;330(6012):1816-20. doi: 10.1126/science.1195821.
Gold, et al. Aptamer-based multiplexed proteomic technology for biomarker discovery. PLoS One. Dec. 7, 2010;5(12):e15004. doi: 10.1371/journal.pone.0015004.
Harper et al. Reaction of serine proteases with substituted isocoumarins: discovery of 3,4-dichloroisocoumarin, a new general mechanism based serine protease inhibitor.Biochemistry 24(8):1831-1841 (Apr. 1985).
Hedstrom, Lizbeth. Serine protease mechanism and specificity. Chem Rev. Dec. 2002;102(12):4501-24.
Jing, et al. Structural basis of profactor D activation: from a highly flexible zymogen to a novel self-inhibited serine protease, complement factor D. EMBO J. Feb. 15, 1999;18(4):804-14.
Jing, et al. Structures of native and complexed complement factor D: implications of the atypical His57 conformation and self-inhibitory loop in the regulation of specific serine protease activity. J Mol Biol. Oct. 9, 1998;282(5):1061-81.
Kam, et al. Human complement proteins D, C2, and B. Active site mapping with peptide thioester substrates. J Biol Chem. Mar. 15, 1987;262(8):3444-51.
Karlin, et al. Applications and statistics for multiple high-scoring segments in molecular sequences. Proc Natl Acad Sci U S A. Jun. 15, 1993;90(12):5873-7.
Karlin, et al. Methods for assessing the statistical significance of molecular sequence features by using general scoring schemes. Proc Natl Acad Sci U S A. Mar. 1990;87(6):2264-8.
Katschke, et al. Inhibiting alternative pathway complement activation by targeting the factor D exosite. J Biol Chem. Apr. 13, 2012;287(16):12886-92. doi: 10.1074/jbc.M112.345082. Epub Feb. 23, 2012.
Katschke, et al. Structural and functional analysis of a C3b-specific antibody that selectively inhibits the alternative pathway of complement. J Biol Chem. Apr. 17, 2009;284(16):10473-9.
Lao et al. Selection of Aptamers Targeting the Sialic Acid Receptor of Hemagglutinin by Epitope-Specific SELEX. Chemical Communications 50(63):8719-8722 (2014).
Loyet, et al. Complement inhibition in cynomolgus monkeys by anti-factor d antigen-binding fragment for the treatment of an advanced form of dry age-related macular degeneration. J Pharmacol Exp Ther. Dec. 2014;351(3):527-37.
Loyet et al. Activation of the Alternative Complement Pathway in Vitreous is Controlled by Genetics in Age-Related Macular Degeneration. 53(10):6628-6637 (Sep. 2012).
Macugen®. Drugs at FDA. Revised Jul. 2011. URL:<https://www.accessdata.fda.gov/drugsatfda_docs/label/2011/021756s018lbl.pdf>.
McHarg, et al. Age-related macular degeneration and the role of the complement system. Mol Immunol. Sep. 2015;67(1):43-50. doi: 10.1016/j.molimm.2015.02.032. Epub Mar. 21, 2015.
Molday, et al. ATP-binding cassette transporter ABCA4: molecular properties and role in vision and macular degeneration. J Bioenerg Biomembr. Dec. 2007;39(5-6):507-17.
Narayana, et al. Structure of human factor D. A complement system protein at 2.0 A resolution. J Mol Biol. Jan. 14, 1994;235(2):695-708.
Ouellet, et al. Hi-Fi SELEX: A High-Fidelity Digital-PCR Based Therapeutic Aptamer Discovery Platform. Biotechnol Bioeng. Aug. 2015;112(8):1506-22.
Ouellet, et al. Hi-Fi SELEX: A High-Fidelity Digital-PCR Based Therapeutic Aptamer Discovery Platform. Supporting Information. Biotechnol Bioeng. Aug. 2015;112(8):1506-22.
Pangburn, MK. Alternative pathway of complement. Methods Enzymol. 1988;162:639-53.
PCT Application PCT/US2018/042317 as filed Jul. 16, 2018.
PCT/US2017/014458 International Search Report dated Apr. 19, 2017.
PCT/US2017/014458 Written Opinion dated Apr. 19, 2017.
PCT/US2018/014573 International Search Report dated May 7, 2018.
PCT/US2018/014579 International Search Report and Written Opinion dated Apr. 13, 2018.
PCT/US2018/042317 International Search Report and Written Opinion dated Oct. 29, 2018.
Preclinical and Phase 1A Clinical Evaluation of an Anti-VEGF Pegylated Aptamer (EYE001) for the Treatment of Exudative Age-Related Macular Degeneration. The Eyetech Study Group. Retina 22(2):143-152 (2002).
Shukla et al. Pegaptanib sodium for ocular vascular disease. Indian J Ophthalmol. 55(6):427-30 (Nov.-Dec. 2007).
U.S. Appl. No. 15/990,547 Notice of Allowance dated May 30, 2019.
U.S. Appl. No. 16/121,458 Office Action dated Jul. 18, 2019.
U.S. Appl. No. 15/693,361 Notice of Allowance dated Aug. 30, 2018.
U.S. Appl. No. 15/693,361 Office Action dated May 25, 2018.
U.S. Appl. No. 15/990,547 Office Action dated Dec. 12, 2018.
Volanakis, et al. Complement factor D, a novel serine protease. Protein Sci. Apr. 1996; 5(4): 553-564. doi: 10.1002/pro.5560050401.
Wiles et al. Preclinical Evaluation of Orally Bioavailable Small-Molecule Inhibitors of Complement Factor D as a Potential Treatment for Paroxysmal Nocturnal Hemoglobinuria. Achillion Pharmaceuticals Inc. Abstract ID: 4819. Presented at the 56th Annual Meeting of the American Society of Hematology, San Francisco, California, USA, Dec. 6-9, 2014. One page.
Wootton, et al. Statistics of local complexity in amino acid sequences and sequence databases. Computers & Chemistry. vol. 17, Issue 2, Jun. 1993, pp. 149-163.

(56) References Cited

OTHER PUBLICATIONS

Yang, et al. Buried Hydrogen Bond Interactions Contribute to the High Potency of Complement Factor D Inhibitors. ACS Med. Chem. Lett., 2016, 7 (12), pp. 1092-1096. DOI: 10.1021/acsmedchemlett.6b00299.
Del Amo et al. Rabbit as an animal model for intravitreal pharmacokinetics: Clinical predictability and quality of the published data. Experimental Eye Research 137:111-124 (Aug. 2015). DOI: https://doi.org/10.1016/j.exer.2015.05.003.
U.S. Appl. No. 16/541,482 Non-Final Office Action dated Apr. 23, 2021.

```
  16                        26                        36                        46                        56
   ILGGREAFAFAHARPYMASVQIN----GAHLCGGVLVAEQWVLSAAHCLEDA
   1         10                20                30                40

66                        76                        86                        96                       106
   ADGKVQVLLGAHSISQ-PEPSKRLYDVLRAVPHPDSQPDTI--DHDLLLI
            50                60                70                80

116                       126                       136                       146
   QLSEKATLG---PAVRPLPWQRVDRDVAPGTLCDVAGWGIVNHA-GRRPDS
            100               110               120               130               140

156                       166                       176                       186                       196
   LQHVLLPVLDRATCNRRTHHDGAITERIMCAFS--NRRDSCKGDSGGPL
            150               160               170               180

206                       216                       226
   VCG---GVLEGVVTSGSRV-CGNRKRPGIYTRVASYAAWIDSVLA---
            190               200               210               220

SEQ ID NO: 94
```

FIG. 14

COMPOSITIONS AND METHODS FOR INHIBITING FACTOR D

CROSS-REFERENCE

This application is a continuation application of U.S. patent application Ser. No. 16/121,458, filed on Sep. 4, 2018, which application is a divisional application of U.S. patent application Ser. No. 15/693,361, filed on Aug. 31, 2017, now U.S. Pat. No. 10,174,325, issued on Jan. 8, 2019, which application is a continuation application of International Patent Application No. PCT/US2017/014458, filed on Jan. 20, 2017, which application claims the benefit of U.S. Provisional Application No. 62/281,092, filed on Jan. 20, 2016, and 62/297,095, filed on Feb. 18, 2016, which applications are incorporated herein by reference in their entireties.

SEQUENCE LISTING

The instant application contains a Sequence Listing which has been submitted electronically in ASCII format and is hereby incorporated by reference in its entirety. Said ASCII copy, created on Jan. 19, 2017, is named 49644-701_601_SL.txt and is 37,821 bytes in size.

BACKGROUND OF THE INVENTION

Visual impairment is a national and global health concern that has a negative impact on physical and mental health. The number of people with visual impairment and blindness is increasing due to an overall aging population. Visual impairment and blindness can be caused by any one of a large number of eye diseases and disorders affecting people of all ages. In one example, age-related macular degeneration (AMD) is an eye disorder that is currently the leading cause of vision loss in people fifty years of age or older in industrialized countries. It is estimated that by 2020, the number of people with AMD could exceed 196 million and by 2040, that number is expected to rise to 288 million. AMD is a degenerative eye disease that progresses from early stages to advanced stages of the disease. Risk factors for the disease include aging, lifestyle factors such as smoking, and genetics. The clearest indicator of progression to AMD is the appearance of drusen, yellow-white deposits under the retina, and it is an important component of both forms of AMD: exudative ("wet") and non-exudative ("dry"). Wet AMD causes vision loss due to abnormal blood vessel growth in the choriocapillaris through Bruch's membrane. The most advanced form of dry AMD, known as geographic atrophy, is generally more gradual and occurs when light-sensitive cells in the macula atrophy, blurring and eliminating vision in the affected eye. While there are currently some promising treatments for wet AMD, no FDA-approved treatment exists for dry AMD or geographic atrophy.

A second example is childhood-onset Stargardt Disease ("STGD"), also known as Stargardt 1, a genetic, rare juvenile macular dystrophy generally associated with loss of central vision in the first two decades of life. STGD has a prevalence of approximately 1/20,000 affecting approximately 30,000 people in the US. STGD affects many ages, with the childhood-onset population at highest risk and most need. Patients with childhood-onset STGD tend to develop early severe visual acuity loss, significantly compromised retinal function, and rapid retinal pigment epithelial (RPE) cell atrophy with accompanying loss of retinal function. The median ages of onset and the median age at baseline examination are 8.5 (range, 3-16) and 12 years (range, 7-16), respectively. Patients with adult-onset disease are more likely to preserve visual acuity for a longer time and show slighter retinal dysfunction. STGD is an autosomal recessive genetic disease or complex heterozygous disease, caused by mutations in the ABCA4 gene. The ABCA4 gene encodes the photoreceptor protein ABCA4 Transporter, which is responsible for removal of all-trans-retinal from photoreceptor cells. Accumulation of all-trans-retinal in photoreceptor cells is believed to damage RPE cells via oxidative stress, and trigger or promote complement-mediated damage to RPE cells, leading to retinal atrophy. A related disease termed Stargardt-like macular dystrophy, also known as STGD3, is inherited in a dominant autosomal manner and is due to mutations in the ELOVL4 gene. ELOVL4 encodes the ELOVL4 protein, ELOVL fatty acid elongase 4. Mutations in ELOVL4 protein associated with STGD lead to mis-folding and accumulation of ELOVL4 protein aggregates in retinal cells, which impact retinal cell function, eventually leading to cell death and retinal atrophy. No treatments exist for STGD or Stargardt-like disease.

SUMMARY OF THE INVENTION

In one aspect, a pharmaceutical composition is provided for treating an ocular disease, comprising a therapeutically effective amount of an aptamer, wherein the aptamer inhibits a function associated with complement Factor D. In some cases, the aptamer binds to complement Factor D. In some instances, the aptamer binds to a catalytic cleft of complement Factor D. In one aspect, a pharmaceutical composition for treating an ocular disease, comprising a therapeutically effective amount of an aptamer, wherein said aptamer inhibits a function associated with complement Factor D, wherein said aptamer binds to an active site, catalytic cleft, or exosite of complement Factor D.

In some instances, the aptamer can bind to an exosite of complement Factor D. In some cases, the aptamer binds to a region of complement Factor D that is recognized by an anti-Factor D antibody or antibody fragment thereof, wherein the anti-Factor D antibody or antibody fragment thereof inhibits a function associated with complement Factor D. In some examples, the anti-Factor D antibody or antibody fragment thereof is an anti-fD Fab having an amino acid sequence of heavy chain variable region according to SEQ ID NO: 71 and a light chain variable region according to SEQ ID NO: 72; an anti-fD Fab having an amino acid sequence of heavy chain variable region according to SEQ ID NOS: 85 or 86 and an amino acid sequence of light chain variable region according to SEQ ID NOS: 87-89; or MAb 166-32 or LS-C135735. In some cases, the aptamer binds to a region of complement Factor D that is recognized by an anti-Factor D small molecule or peptide, wherein the anti-Factor D small molecule or peptide inhibits a function associated with complement Factor D. In some cases, the small molecule is dichloroisocoumarin (DIC) or any one of the small molecules depicted in FIGS. 13A-D. In some cases, the region is an epitope recognized by the anti-Factor D antibody or antibody fragment thereof. In some cases, the aptamer is an RNA aptamer, a modified RNA aptamer, a DNA aptamer, a modified DNA aptamer, or any combination thereof. In some cases, the aptamer is coupled to a high-molecular weight polyethylene glycol (PEG) polymer. The PEG polymer can have a molecular weight of about 10 kDa to about 80 kDa. The pharmaceutical composition can be formulated for intravitreal administration. The pharmaceutical composition can be formulated for topical administration. In some cases, the ocular disease is macular degeneration. In some cases, the ocular disease is age-related macular degeneration. In some cases, the ocular disease is dry age-related macular degeneration. In some cases, the ocular disease is geographic atrophy. In some cases, the ocular disease is wet age-related macular degeneration. In some cases, the ocular disease is Stargardt disease. In some cases, the aptamer has an intraocular half-life of greater than about 7 days in a human. In some cases, the aptamer inhibits a function of complement Factor D with an $IC_{50}$ of about 50 nM or less as measured by a C3 hemolysis assay. In some cases, the aptamer inhibits a function of complement Factor D with an $IC_{50}$ of about 5 nM or less as measured by a C3 hemolysis assay. In some cases, the aptamer increases activity of complement Factor D as measured by a Factor D esterase activity assay as compared to a control, and further inhibits activity of complement Factor D as measured by a hemolysis assay. In other cases, the aptamer inhibits activity of complement Factor D as measured by a Factor D esterase activity assay as compared to a control, and further inhibits activity of complement Factor D as measured by a hemolysis assay. In yet other cases, the aptamer does not inhibit activity of complement Factor D as measured by a Factor D esterase activity assay as compared to a control, and does inhibit activity of complement Factor D as measured by a hemolysis assay. In some cases, the aptamer binds to complement Factor D with a $K_d$ of less than about 50 nM. In some cases, the aptamer binds to complement Factor D with a $K_d$ of less than about 5 nM. In some cases, the aptamer binds to complement Factor D with a $K_d$ of less than about 500 pM. In some cases, the aptamer binds to complement Factor D with a $K_d$ of less than about 50 pM. In some cases, the aptamer binds to complement Factor D with a $K_d$ of less than about 5 pM. In some cases, the aptamer binds to the catalytic cleft, the active site, the exosite, and/or the self-inhibitory loop of fD with a $K_d$ of less than about 50 nM, 5 nM, 50 pM, or 5 pM. In some instances, the aptamer binds to complement Factor D with a specificity at least 10-fold greater than the aptamer binds to any of C3, C5, Factor B, Factor H or Factor I at relative serum concentrations. In some instances, the aptamer binds to complement Factor D with a specificity at least 50-fold greater than the aptamer binds to any of C3, C5, Factor B, Factor H or Factor I at relative serum concentrations. In some instances, the aptamer binds to complement Factor D with a specificity at least 100-fold greater than the aptamer binds to any of C3, C5, Factor B, Factor H or Factor I at relative serum concentrations. In some cases, the therapeutically effective amount is about 0.01 mg to about 60 mg in about 25p to about 100 µl volume per eye. In some cases, the pharmaceutical composition is formulated for delivery to a subject once every 4 weeks. In some cases, the pharmaceutical composition is formulated for delivery to a subject once every 6 weeks. In some cases, the pharmaceutical composition is formulated for delivery to a subject once every 8 weeks. In some cases, the pharmaceutical composition is formulated for delivery to a subject once every 10 weeks. In some cases, the pharmaceutical composition is formulated for delivery to a subject once every 12 weeks.

In another aspect, a method is provided for treating an ocular disease in a subject, the method comprising: administering to the subject a pharmaceutical composition comprising a therapeutically effective amount of an aptamer, wherein the aptamer inhibits a function associated with complement Factor D. In some cases, the aptamer binds to complement Factor D. In some instances the aptamer binds to a catalytic cleft of complement Factor D. In some instances, the aptamer binds to an exosite of complement Factor D. In some cases, the aptamer binds to a region of complement Factor D that is recognized by an anti-Factor D antibody or antibody fragment thereof, wherein the anti-Factor D antibody or antibody fragment thereof inhibits a function associated with complement Factor D. In some cases, the anti-Factor D antibody or antibody fragment thereof is an anti-fD Fab having an amino acid sequence of heavy chain variable region according to SEQ ID NO: 71 and a light chain variable region according to SEQ ID NO: 72; or an anti-fD Fab having an amino acid sequence of heavy chain variable region according to SEQ ID NOS: 85 or 86 and an amino acid sequence of light chain variable region according to SEQ ID NOS: 87-89; or MAb 166-32 or LS-C135735. In some cases, the aptamer binds to a region of complement Factor D that is recognized by an anti-Factor D small molecule or peptide, wherein the anti-Factor D small molecule or peptide inhibits a function associated with complement Factor D. In some cases, the small molecule is dichloroisocoumarin (DIC) or any one of the small molecules depicted in FIGS. 13A-D. In some cases, the region is an epitope recognized by an anti-Factor D antibody or antibody fragment thereof. In some cases, the aptamer is an RNA aptamer, a modified RNA aptamer, a DNA aptamer, a modified DNA aptamer, or any combination thereof. In some cases, the aptamer is coupled to a high-molecular weight polyethylene glycol (PEG) polymer. In some cases, the PEG polymer has a molecular weight of about 10 kDa to about 80 kDa. In some cases, pharmaceutical composition is administered by intravitreal administration. In some cases, the pharmaceutical composition is administered by topical administration. In some cases, the ocular disease is macular degeneration. In some cases, the ocular disease is age-related macular degeneration. In some cases, the ocular disease is dry age-related macular degeneration. In some cases, the ocular disease is geographic atrophy. In some cases, the ocular disease is wet age-related macular degeneration. In some cases, the ocular disease is Stargardt disease. In some cases, the aptamer has an intraocular half-life of greater than about 7 days. In some cases, the aptamer inhibits a function of complement Factor D with an $IC_{50}$ of about 50 nM or less as measured by a C3 hemolysis assay. In some cases, the aptamer inhibits a function of complement Factor D with an $IC_{50}$ of about 5 nM or less as measured by a C3 hemolysis assay. In some cases, the aptamer increases activity of complement Factor D as measured by a Factor D esterase activity assay as compared to a control, and further inhibits activity of complement Factor D as measured by a hemolysis assay. In other cases, the aptamer inhibits activity of complement Factor D as measured by a Factor D esterase activity assay as compared to a control, and further inhibits activity of complement Factor D as measured by a hemolysis assay. In yet other cases, the aptamer does not inhibit activity of complement Factor D as measured by a Factor D esterase activity assay as compared to a control, and does inhibit activity of complement Factor D as measured by a hemolysis assay. In some instances, the aptamer binds to complement Factor D with a $K_d$ of less than about 50 nM. In some instances, the aptamer binds to complement Factor D with a $K_d$ of less than about 5 nM. In some instances, the aptamer binds to complement Factor D with a $K_d$ of less than about 500 pM. In some instances, the aptamer binds to complement Factor D with a $K_d$ of less than about 50 pM. In some instances, the aptamer binds to complement Factor D with a $K_d$ of less than about 5 pM. In some cases, the aptamer binds to the catalytic cleft, the active site, the exosite, and/or the self-inhibitory loop of fD with a $K_d$ of less than about 50 nM, 5 nM, 50 pM, or 5 pM. In some cases, the aptamer binds to complement Factor D with a specificity at least 10-fold greater than the aptamer binds to any of C3, C5, Factor B, Factor H or Factor I at relative serum concentrations. In some cases, the aptamer binds to complement Factor D with a specificity at least 50-fold greater than the aptamer binds to any of C3, C5, Factor B, Factor H or Factor I at relative serum concentrations. In some cases, the aptamer binds to complement Factor D with a specificity at least 100-fold greater than aptamer binds to any of C3, C5, Factor B, Factor H or Factor I at relative serum concentrations. In some cases, the therapeutically effective amount comprises about 0.01 mg to about 60 mg in about 25 µl to about 100 µl volume per eye. In some cases, the pharmaceutical composition is administered to the subject once every 4 weeks. In some cases, the pharmaceutical composition is administered to the subject once every 6 weeks. In some cases, the pharmaceutical composition is administered to the subject once every 8 weeks. In some cases, the pharmaceutical composition is administered to the subject once every 10 weeks. In some cases, the pharmaceutical composition is administered to the subject once every 12 weeks.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIGS. 2A & 2B demonstrate IVT inhibition of Factor D at various IVT concentrations of an anti-Factor D aptamer. Effective inhibition of IVT Factor D inhibition was modeled using a standard 2 compartment model, assuming reported IVT half-lives for Fabs (7 days, LUCENTIS®) and PEGylated aptamers (10 days, MACUGEN®) and 1:1 inhibition of Factor D by each therapy at the relevant IVT concentrations ($IC_{50}$ data). As depicted in FIG. 2A, effective inhibition curves after IVT injection are shown for an anti-Factor D Fab (dashed line), an anti-Factor D aptamer VT-001 (solid line), and the intercept with the serum level of Factor D (dotted line) can be visualized as a surrogate for loss of clinically relevant Factor D inhibition. FIG. 2B depicts the predicted IVT drug concentration (nM) of PEGylated aptamer (dotted line) and an anti-Factor D antibody (solid line) over the number of weeks post IVT injection.

FIG. 3A discloses SEQ ID NO: 95. FIG. 3B discloses SEQ ID NOS: 95 and 65, respectively, in order of appearance.

FIG. 14 depicts the amino acid sequence of human complement Factor D, chymotrypsin numbering scheme, and fD numbering scheme.

DETAILED DESCRIPTION OF THE INVENTION

Figure 1:
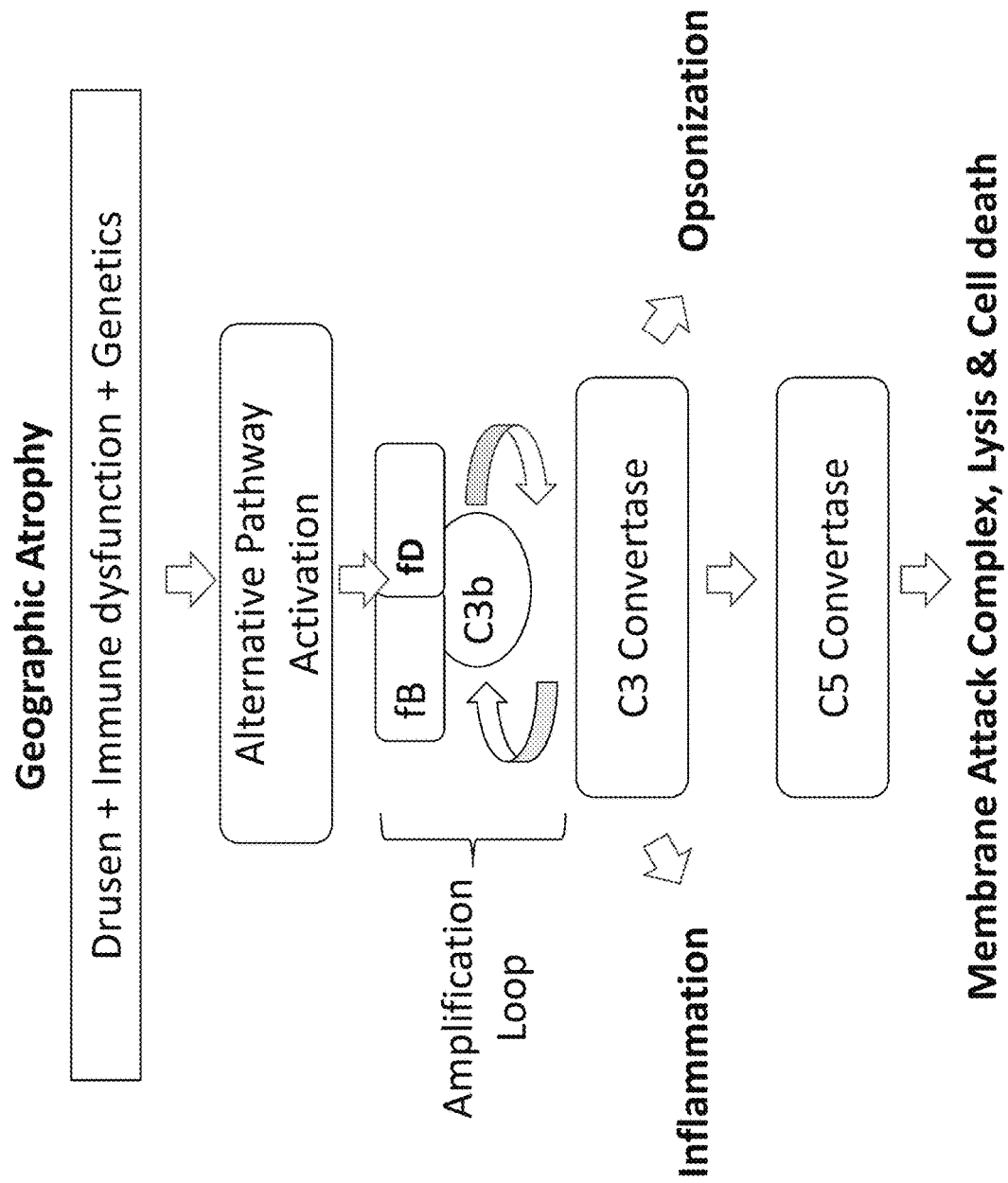
FIG. 1 depicts aspects of the alternative complement pathway.
Figure 2A:
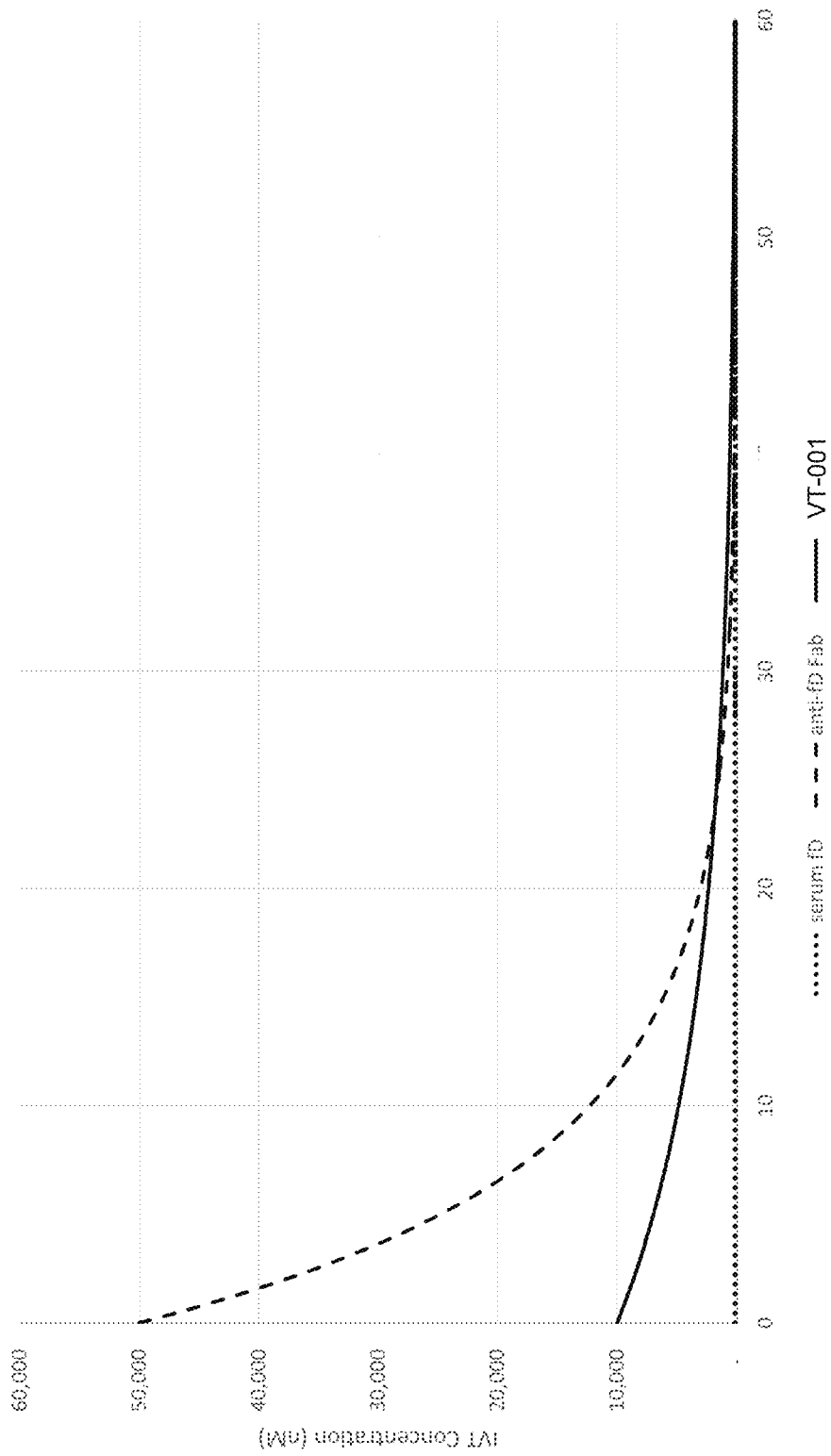
FIG. 2A and FIG. 2B depict modeling of the intravitreal (IVT) inhibition of Factor D by an anti-Factor D aptamer at various IVT concentrations.
Figure 2B:
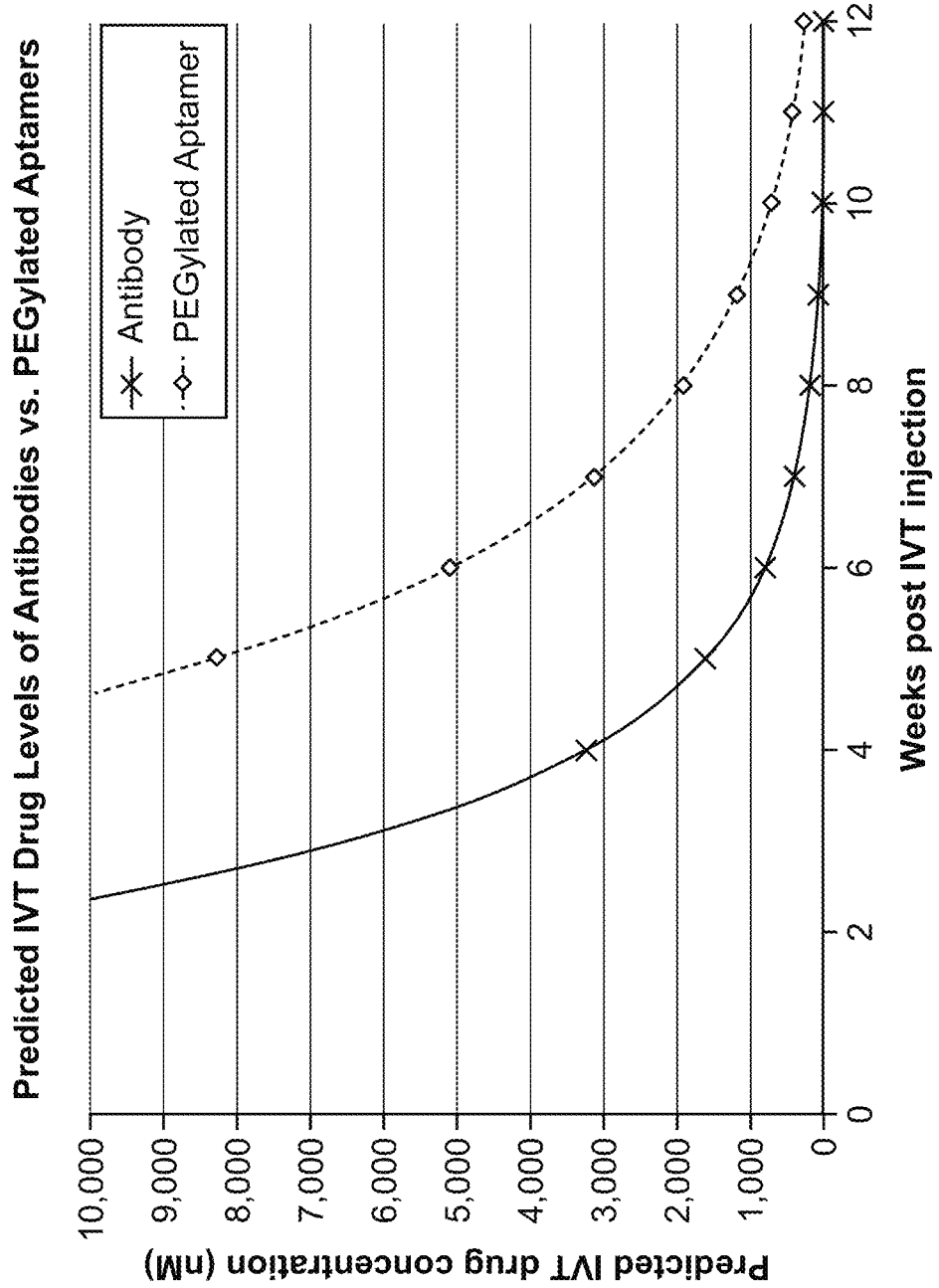

The disclosure herein provides methods and compositions for the treatment of ocular diseases or disorders. In some cases, the ocular disease is macular degeneration. In some cases, macular degeneration is age-related macular degeneration. In some cases, age-related macular degeneration is dry age-related macular degeneration. In some cases, dry age-related macular degeneration is advanced dry age-related macular degeneration (i.e., geographic atrophy). In some cases, the ocular disease is wet age-related macular degeneration. In some cases, the ocular disease is Stargardt disease. In some cases, the methods and compositions involve the inhibition of the alternative complement pathway. In some cases, the methods and compositions involve the inhibition of a function associated with Factor D (fD). In some cases, the methods and compositions involve the inhibition of a function associated with fD for the treatment of ocular diseases. In some cases, the methods and compositions involve the inhibition of a function associated with fD for the treatment of dry age-related macular degeneration or geographic atrophy. In some cases, the methods and compositions involve the inhibition of a function associated with fD for the treatment of wet age-related macular degeneration. In some cases, the methods and compositions involve the inhibition of a function associated with fD for the treatment of Stargardt disease. In some cases, the methods and compositions include the use of an anti-fD aptamer.

The practice of some embodiments disclosed herein employ, unless otherwise indicated, conventional techniques of immunology, biochemistry, chemistry, molecular biology, microbiology, cell biology, genomics and recombinant DNA, which are within the skill of the art. See for example Sambrook and Green, Molecular Cloning: A Laboratory Manual, 4th Edition (2012); the series Current Protocols in Molecular Biology (F. M. Ausubel, et al. eds.); the series Methods In Enzymology (Academic Press, Inc.), PCR 2: A Practical Approach (M. J. MacPherson, B. D. Hames and G. R. Taylor eds. (1995)), Harlow and Lane, eds. (1988) Antibodies, A Laboratory Manual, and Culture of Animal Cells: A Manual of Basic Technique and Specialized Applications, 6th Edition (R. I. Freshney, ed. (2010)).

In general, "sequence identity" refers to an exact nucleotide-to-nucleotide or amino acid-to-amino acid correspondence of two polynucleotides or polypeptide sequences, respectively. Typically, techniques for determining sequence identity include determining the nucleotide sequence of a polynucleotide and/or determining the amino acid sequence encoded thereby, and comparing these sequences to a second nucleotide or amino acid sequence. Two or more sequences (polynucleotide or amino acid) can be compared by determining their "percent identity." The percent identity of two sequences, whether nucleic acid or amino acid sequences, is the number of exact matches between two aligned sequences divided by the length of the shorter sequences and multiplied by 100. Percent identity may also be determined, for example, by comparing sequence information using the advanced BLAST computer program, including version 2.2.9, available from the National Institutes of Health. The BLAST program is based on the alignment method of Karlin and Altschul, Proc. Natl. Acad. Sci. USA 87:2264-2268 (1990) and as discussed in Altschul, et al., J. Mol. Biol. 215:403-410 (1990); Karlin And Altschul, Proc. Natl. Acad. Sci. USA 90:5873-5877 (1993); and Altschul et al., Nucleic Acids Res. 25:3389-3402 (1997). Briefly, the BLAST program defines identity as the number of identical aligned symbols (generally nucleotides or amino acids), divided by the total number of symbols in the shorter of the two sequences. The program may be used to determine percent identity over the entire length of the proteins being compared. Default parameters are provided to optimize searches with short query sequences in, for example, with the blastp program. The program also allows use of an SEG filter to mask-off segments of the query sequences as determined by the SEG program of Wootton and Federhen, Computers and Chemistry 17:149-163 (1993). Ranges of desired degrees of sequence identity are approximately 80% to 100% and integer values therebetween. Typically, the percent identities between a disclosed sequence and a claimed sequence are at least 80%, at least 85%, at least 90%, at least 95%, or at least 98%.

The terms "peptide" and "protein" are used interchangeably herein to refer to polymers of amino acids of any length. A polypeptide can be any protein, peptide, protein fragment or component thereof. A polypeptide can be a protein naturally occurring in nature or a protein that is ordinarily not found in nature. A polypeptide can consist largely of the standard twenty protein-building amino acids or it can be modified to incorporate non-standard amino acids. A polypeptide can be modified, typically by the host cell, by e.g., adding any number of biochemical functional groups, including phosphorylation, acetylation, acylation, formylation, alkylation, methylation, lipid addition (e.g. palmitoylation, myristoylation, prenylation, etc) and carbohydrate addition (e.g. N-linked and O-linked glycosylation, etc). Polypeptides can undergo structural changes in the host cell such as the formation of disulfide bridges or proteolytic cleavage. The peptides described herein may be therapeutic peptides utilized for e.g., the treatment of a disease.

The term "aptamer" as used herein refers to an oligonucleotide and/or nucleic acid analogues that can bind to a specific target molecule. Aptamers can include RNA, DNA, any nucleic acid analogue, and/or combinations thereof. Aptamers can be single-stranded oligonucleotides. Without wishing to be bound by theory, aptamers are thought to bind to a three-dimensional structure of a target molecule. Aptamers may be monomeric (composed of a single unit) or multimeric (composed of multiple units). Multimeric aptamers can be homomeric (composed of multiple identical units) or heteromeric (composed of multiple non-identical units).

The term "exosite" as used herein may refer to a protein domain or region of a protein that is capable of binding to another protein. The exosite may also be referred to herein as a "secondary binding site", for example, a binding site that is remote from or separate from a primary binding site (e.g., an active site). In some cases, the primary and secondary binding sites may overlap. Binding of a molecule to an exosite may cause a physical change in the protein (e.g., a conformational change). In some cases, the activity of a protein may be dependent on occupation of the exosite. In some examples, the exosite may be distinct from an allosteric site.

The term "catalytic cleft" or "active site" as used herein refers to a domain of an enzyme in which a substrate molecule binds to and undergoes a chemical reaction. The active site may include amino acid residues that form temporary bonds with the substrate (e.g., a binding site) and amino acid residues that catalyze a reaction of that substrate (e.g., catalytic site). The active site may be a groove or pocket (e.g., a cleft) of the enzyme which can be located in a deep tunnel within the enzyme or between the interfaces of multimeric enzymes.

The term "epitope" as used herein refers to the part of an antigen (e.g., a substance that stimulates an immune system to generate an antibody against) that is specifically recognized by the antibody. In some cases, the antigen is a protein or peptide and the epitope is a specific region of the protein or peptide that is recognized and bound by an antibody. In some cases, the aptamers described herein bind to a region of fD that is an epitope for an anti-fD antibody or antibody fragment thereof, wherein the anti-fD antibody inhibits a function associated with fD. In some cases, the aptamer binding region of fD overlaps with at least 50%, at least 60%, at least 70%, at least 80%, at least 90%, at least 95%, or 100% of the epitope for an anti-fD antibody or the binding site of another fD-inhibiting molecule.

The terms "subject" and "patient" are used interchangeably herein to refer to a vertebrate, preferably a mammal, more preferably a human. Mammals include, but are not limited to, murines, simians, humans, farm animals, sport animals, and pets. Tissues, cells, and their progeny of a biological entity obtained in vivo or cultured in vitro are also encompassed.

The Complement System and the Alternative Complement Pathway

The complement system is a part of the innate immune system that enhances the ability of antibodies and phagocytic cells to clear pathogens from an organism. Although the system is not adaptable and does not change over the course of an individual's lifetime, it can be recruited and brought into action by the adaptive immune system.

The complement system consists of a number of small proteins found in the blood, in general synthesized by the liver, and normally circulating as inactive precursors (proproteins). When stimulated by one of several triggers, proteases in the system cleave specific proteins to release cytokines and initiate an amplifying cascade of further cleavages. The end result of this complement activation or complement fixation cascade is massive amplification of the response and activation of the cell-killing membrane attack complex. Over 30 proteins and protein fragments make up the complement system, including serum proteins, serosal proteins, and cell membrane receptors.

The alternative complement pathway is a rapid, antibody-independent route for complement system activation and amplification. The alternative pathway comprises several components: C3, Factor B (fB), and fD. Activation of the alternative pathway occurs when C3b, a proteolytic cleavage form of C3, is bound to an activating surface agent such as a bacterium. fB is then bound to C3b, and cleaved by fD to yield the C3 convertase C3bBb. Amplification of C3 convertase activity occurs as additional C3b is produced and deposited. The amplification response is further aided by the binding of the positive regulator protein properdin (Factor P), which stabilizes the active convertase against degradation, extending its half-life from 1-2 minutes to 18 minutes.

The C3 convertase further assembles into a C5 convertase (C3b3bBb). This complex subsequently cleaves complement component C5 into two components: the C5a polypeptide (9 kDa) and the C5b polypeptide (170 kDa). The C5a polypeptide binds to a 7 transmembrane G-protein coupled receptor, which was originally associated with leukocytes and is now known to be expressed on a variety of tissues including hepatocytes and neurons. The C5a molecule is the primary chemotactic component of the human complement system and can trigger a variety of biological responses including leukocyte chemotaxis, smooth muscle contraction, activation of intracellular signal transduction pathways, neutrophil-endothelial adhesion, cytokine and lipid mediator release and oxidant formation.

The alternative complement pathway is believed to play a role in the pathogenesis of a variety of ischemic, inflammatory and autoimmune diseases including age-related macular degeneration, geographic atrophy, Stargardt disease, systemic lupus erythematosus, rheumatoid arthritis, and asthma. Thus, components of the alternative complement pathway may be important targets for the treatment of these diseases.

Age-Related Macular Degeneration

Age-related macular degeneration ("AMD") is a chronic and progressive eye disease that is the leading cause of irreparable vision loss in the United States, Europe, and Japan. AMD is characterized by the progressive deterioration of the central portion of the retina referred to as the macula. The clearest indicator of progression to AMD is the appearance of drusen, yellow-white deposits under the retina, which are plaques of material that are derived from the metabolic waste products of retinal cells. The appearance of drusen is an important component of both forms of AMD: exudative ("wet") and non-exudative ("dry"). The presence of numerous, intermediate-to-large drusen is associated with the greatest risk of progression to late-stage disease, characterized by geographic atrophy and/or neovascularization. The majority of patients with wet AMD experience severe vision loss in the affected eye within months to two years after diagnosis of the disease, although vision loss can occur within hours or days. Dry AMD is more gradual and occurs when light-sensitive cells in the macula slowly atrophy, gradually blurring central vision in the affected eye. Vision loss is exacerbated by the formation and accumulation of drusen and sometimes the deterioration of the retina, although without abnormal blood vessel growth and bleeding. Geographic atrophy is a term used to refer to advanced dry AMD. Geographic atrophy is characterized by an "island" of atrophied photoreceptors cells. It is believed that the alternative complement pathway may play a role in the pathogenesis of AMD.

Stargardt Disease

Stargardt Disease ("STGD") is a rare, genetic, macular dystrophy with an incidence of 1/20,000, affecting approximately 30,000 individuals in the United States. STGD is an autosomal recessive or complex heterozygous genetic disease caused by mutations in the ABCA4 gene. The ABCA4 gene encodes the photoreceptor protein ABCA4 Transporter, which is responsible for removal of all-trans-retinal from photoreceptor cells. Accumulation of all-trans-retinal in photoreceptor cells is believed to damage RPE cells via oxidative stress, and trigger or promote complement-mediated damage to RPE cells, leading to retinal atrophy. STGD is characterized by the progressive deterioration of the central portion of the retina referred to as the macula, generally beginning in the first two decades of life. The clearest indicator of progression of STGD is the appearance of drusen, yellow-white deposits under the retina, which are plaques of material that are derived from the metabolic waste products of retinal cells, including all-trans-retinal and other vitamin A-related metabolites. The onset of STGD is typically between the ages of 6-20 years, with early symptoms including difficulties in reading and adjusting to light. Patients with childhood-onset STGD tend to develop early severe visual acuity loss, significantly compromised retinal function, and rapid retinal pigment epithelial (RPE) cell atrophy with accompanying loss of retinal function. The median ages of onset and the median age at baseline examination are 8.5 (range, 3-16) and 12 years (range, 7-16), respectively. Patients with adult-onset disease are more likely to preserve visual acuity for a longer time and show slighter retinal dysfunction. Accumulation of all-trans-retinal in photoreceptor cells leads to inflammation, oxidative stress, deposition of auto-fluorescent lipofuscin pigments in the retinal pigment epithelium and retinal atrophy. Lipofuscin deposits (drusen), and oxidative products, trigger the alternative complement pathway into an inflammatory response leading to cell death. Data supporting the role of alternative complement in STGD include human cell models, genetic mouse models and the accumulation of complement factors in humans in drusen during disease progression. Therefore, inhibitors of complement, particularly complement factor D, are anticipated to stop or slow the progression of vision loss in individuals with STGD. A related disease termed Stargardt-like macular dystrophy, also known as STGD3, is inherited in a dominant autosomal manner and is due to mutations in the ELOVL4 gene. ELOVL4 encodes the ELOVL4 protein, ELOVL fatty acid elongase 4. Mutations in ELOVL4 protein associated with STGD lead to mis-folding and accumulation of ELOVL4 protein aggregates in retinal cells, which impact retinal cell function, eventually leading to cell death and retinal atrophy. Complement pathway activation is also thought to play a role in Stargardt-like disease, and therefore inhibitors of complement, particularly complement factor D, are anticipated to stop or slow the progression of vision loss in individuals with Stargardt-like disease.

Aptamers

In some cases, the methods and compositions described herein utilize one or more aptamers for the treatment of an ocular disease. The term aptamer as used herein refers to oligonucleotide molecules that bind to a target (e.g., a protein) with high affinity and specificity through non-Watson-Crick base pairing interactions. Generally, the aptamers described herein are non-naturally occurring oligonucleotides (i.e., synthetically produced) that are isolated and used for the treatment of a disorder or a disease. Aptamers can bind to essentially any target molecule including, without limitation, proteins, oligonucleotides, carbohydrates, lipids, small molecules, and even bacterial cells. The aptamers described herein are oligonucleotides that bind to proteins of the alternative complement pathway. Whereas many naturally occurring oligonucleotides, such as mRNA, encode information in their linear base sequences, aptamers can be distinguished from these naturally occurring oligonucleotides in that binding of the aptamer to a target molecule is dependent upon secondary and tertiary structures of the aptamer rather than a conserved linear base sequence and the aptamer generally does not encode information in its linear base sequence.

Aptamers may be suitable as therapeutic agents and may be preferable to other therapeutic agents because: 1) aptamers may be fast and economical to produce because aptamers can be developed entirely by in vitro processes; 2) aptamers may have low toxicity and may lack an immunogenic response; 3) aptamers may have high specificity and affinity for their targets; 4) aptamers may have good solubility; 5) aptamers have tunable pharmacokinetic properties; 6) aptamers are amenable to site-specific conjugation of PEG and other carriers; and 7) aptamers may be stable at ambient temperatures.

Aptamers as described herein may include any number of modifications than can affect the function or affinity of the aptamer. For example, aptamers may be unmodified or they may contain modified nucleotides to improve stability, nuclease resistance or delivery characteristics. Examples of such modifications may include chemical substitutions at the sugar and/or phosphate and/or base positions, for example, at the 2' position of ribose, the 5 position of pyrimidines, and the 8 position of purines, various 2'-modified pyrimidines and modifications with 2'-amino (2'-NH2), 2'-fluoro (2'-F), and/or 2'-O-methyl (2'-OMe) substituents. In some cases, aptamers described herein comprise a 2'-OMe modification to increase in vivo stability. In some cases, the aptamers described herein contain modified nucleotides to improve the affinity and specificity of the aptamers for a specific epitope, exosite or active site. Examples of modified nucleotides include those modified with guanidine, indole, amine, phenol, hydroxymethyl, or boronic acid. In other cases, pyrimidine nucleotide triphosphate analogs or CE-phosphoramidites may be modified at the 5 position to generate, for example, 5-benzylaminocarbonyl-2'-deoxyuridine (BndU); 5-[N-(phenyl-3-propyl)carboxamide]-2'-deoxyuridine (PPdU); 5-(N-thiophenylmethylcarboxyamide)-2'-deoxyuridine (ThdU); 5-(N-4-fluorobenzylcarboxyamide)-2'-deoxyuridine (FBndU); 5-(N-(1-naphthylmethyl)carboxamide)-2'-deoxyuridine (NapdU); 5-(N-2-naphthylmethylcarboxyamide)-2'-deoxyuridine (2NapdU); 5-(N-1-naphthylethylcarboxyamide)-2'-deoxyuridine (NEdU); 5-(N-2-naphthylethylcarboxyamide)-2'-deoxyuridine (2NEdU); 5-(N-tryptaminocarboxyamide)-2'-deoxyuridine (TrpdU); 5-isobutylaminocarbonyl-2'-deoxyuridine (IbdU); 5-(N-tyrosylcarboxyamide)-2'-deoxyuridine (TyrdU); 5-(N-isobutylaminocarbonyl-2'-deoxyuridine (iBudU); 5-(N-benzylcarboxyamide)-2'-O-methyluridine, 5-(N-benzylcarboxyamide)-2'-fluorouridine, 5-(N-phenethylcarboxyamide)-2'-deoxyuridine (PEdU), 5-(N-3,4-methylenedioxybenzylcarboxyamide)-2'-deoxyuridine (MBndU), 5-(N-imidizolylethylcarboxyamide)-2'-deoxyuridine (ImdU), 5-(N-isobutylcarboxyamide)-2'-O-methyluridine, 5-(N-isobutylcarboxyamide)-2'-fluorouridine, 5-(N—R-threoninylcarboxyamide)-2'-deoxyuridine (ThrdU), 5-(N-tryptaminocarboxyamide)-2'-O-methyluridine, 5-(N-tryptaminocarboxyamide)-2'-fluorouridine, 5-(N-[1-(3-trimethylamonium)propyl]carboxyamide)-2'-deoxyuridine chloride, 5-(N-naphthylmethylcarboxyamide)-2'-O-methyluridine, 5-(N-naphthylmethylcarboxyamide)-2'-fluorouridine, 5-(N-[1-(2,3-dihydroxypropyl)]carboxyamide)-2'-deoxyuridine), 5-(N-2-naphthylmethylcarboxyamide)-2'-O-methyluridine, 5-(N-2-naphthylmethylcarboxyamide)-2'-fluorouridine, 5-(N-1-naphthylethylcarboxyamide)-2'-O-methyluridine, 5-(N-1-naphthylethylcarboxyamide)-2'-fluorouridine, 5-(N-2-naphthylethylcarboxyamide)-2'-O-methyluridine, 5-(N-2-naphthylethylcarboxyamide)-2'-fluorouridine, 5-(N-3-benzofuranylethylcarboxyamide)-2'-deoxyuridine (BFdU), 5-(N-3-benzofuranylethylcarboxyamide)-2'-O-methyluridine, 5-(N-3-benzofuranylethylcarboxyamide)-2'-fluorouridine, 5-(N-3-benzothiophenylethylcarboxyamide)-2'-deoxyuridine (BTdU), 5-(N-3-benzothiophenylethylcarboxyamide)-2'-O-methyluridine, 5-(N-3-benzothiophenylethylcarboxyamide)-2'-fluorouridine; 5-[N-(1-morpholino-2-ethyl)carboxamide]-2'-deoxyuridine (MOEdu); R-tetrahydrofuranylmethyl-2'-deoxyuridine (RTMdU); 3-methoxybenzyl-2'-deoxyuridine (3MBndU); 4-methoxybenzyl-2'-deoxyuridine (4MBndU); 3,4-dimethoxybenzyl-2'-deoxyuridine (3,4DMBndU); S-tetrahydrofuranylmethyl-2'-deoxyuridine (STMdU); 3,4-methylenedioxyphenyl-2-ethyl-2'-deoxyuridine (MPEdU); 4-pyridinylmethyl-2'-deoxyuridine (PyrdU); or 1-benzimidazol-2-ethyl-2'-deoxyuridine (BidU); 5-(amino-1-propenyl)-2'-deoxyuridine; 5-(indole-3-acetamido-1-propenyl)-2'-deoxyuridine; or 5-(4-pivaloylbenzamido-1-propenyl)-2'-deoxyuridine.

Modifications of the aptamers contemplated in this disclosure include, without limitation, those which provide other chemical groups that incorporate additional charge, polarizability, hydrophobicity, hydrogen bonding, electrostatic interaction, and functionality to the nucleic acid aptamer bases or to the nucleic acid aptamer as a whole. Modifications to generate oligonucleotide populations that are resistant to nucleases can also include one or more substitute internucleotide linkages, altered sugars, altered bases, or combinations thereof. Such modifications include, but are not limited to, 2'-position sugar modifications, 5-position pyrimidine modifications, 8-position purine modifications, modifications at exocyclic amines, substitution of 4-thiouridine, substitution of 5-bromo or 5-iodo-uracil; backbone modifications, phosphorothioate or alkyl phosphate modifications, methylations, and unusual base-pairing combinations such as the isobases isocytidine and isoguanosine. Modifications can also include 3' and 5' modifications such as capping, e.g., addition of a 3'-3'-dT cap to increase exonuclease resistance.

The length of the aptamer can be variable. In some cases, the length of the aptamer is less than 100 nucleotides. In some cases, the length of the aptamer is greater than 10 nucleotides. In some cases, the length of the aptamer is between 10 and 90 nucleotides. The aptamer can be, without limitation, about 10, about 15, about 20, about 25, about 30, about 35, about 40, about 45, about 50, about 55, about 60, about 65, about 70, about 75, about 80, about 85, or about 90 nucleotides in length.

In some instances, a polyethylene glycol (PEG) polymer chain is covalently bound to the aptamer, referred to herein as PEGylation. Without wishing to be bound by theory, PEGylation may increase the half-life and stability of the aptamer in physiological conditions. In some cases, the PEG polymer is covalently bound to the 5' end of the aptamer. In some cases, the PEG polymer is covalently bound to the 3' end of the aptamer. In some cases, the PEG polymer is covalently bound to specific site on a nucleobase within the aptamer, including the 5-position of a pyrimidine or 8-position of a purine.

In some cases, an aptamer described herein may be conjugated to a PEG having the general formula, H—(O—CH$_2$—CH$_2$)$_n$—OH. In some cases, an aptamer described herein may be conjugated to a methoxy-PEG (mPEG) of the general formula, CH$_3$O—(CH$_2$—CH$_2$—O)$_n$—H. In some cases, the aptamer is conjugated to a linear chain PEG or mPEG. The linear chain PEG or mPEG may have an average molecular weight of up to about 30 kD. Multiple linear chain PEGs or mPEGs can be linked to a common reactive group to form multi-arm or branched PEGs or mPEGs. For example, more than one PEG or mPEG can be linked together through an amino acid linker (e.g., lysine) or another linker, such as glycerine. In some cases, the aptamer is conjugated to a branched PEG or branched mPEG. Branched PEGs or mPEGs may be referred to by their total mass (e.g., two linked 20 kD mPEGs have a total molecular weight of 40 kD). Branched PEGs or mPEGs may have more than two arms. Multi-arm branched PEGs or mPEGs may be referred to by their total mass (e.g. four linked 10 kD mPEGs have a total molecular weight of 40 kD). In some cases, an aptamer of the present disclosure is conjugated to a PEG polymer having a total molecular weight from about 5 kD to about 200 kD, for example, about 5 kD, about 10 kD, about 20 kD, about 30 kD, about 40 kD, about 50 kD, about 60 kD, about 70 kD, about 80 kD, about 90 kD, about 100 kD, about 110 kD, about 120 kD, about 130 kD, about 140 kD, about 150 kD, about 160 kD, about 170 kD, about 180 kD, about 190 kD, or about 200 kD. In one non-limiting example, the aptamer is conjugated to a PEG having a total molecular weight of about 40 kD.

In some cases, the reagent that may be used to generate PEGylated aptamers is a branched PEG N-Hydroxysuccinimide (mPEG-NHS) having the general formula:

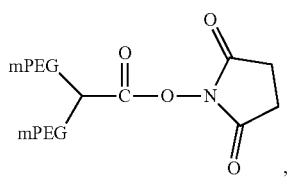

with a 20 kD, 40 kD or 60 kD total molecular weight (e.g., where each mPEG is about 10 kD, 20 kD or about 30 kD). As described above, the branched PEGs can be linked through any appropriate reagent, such as an amino acid (e.g., lysine or glycine residues).

In one non-limiting example, the reagent used to generate PEGylated aptamers is [N$^2$-(monomethoxy 20K polyethylene glycol carbamoyl)-N$^6$-(monomethoxy 20K polyethylene glycol carbamoyl)]-lysine N-hydroxysuccinimide having the formula:

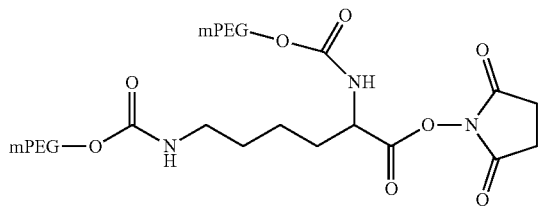

In yet another non-limiting example, the reagent used to generate PEGylated aptamers has the formula:

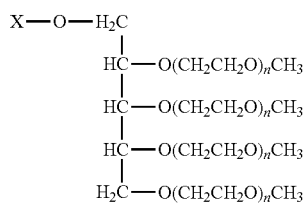

where X is N-hydroxysuccinimide and the PEG arms are of approximately equivalent molecular weight. Such PEG architecture may provide a compound with reduced viscosity compared to a similar aptamer conjugated to a two-armed or single-arm linear PEG.

In some examples, the reagent used to generate PEGylated aptamers has the formula:

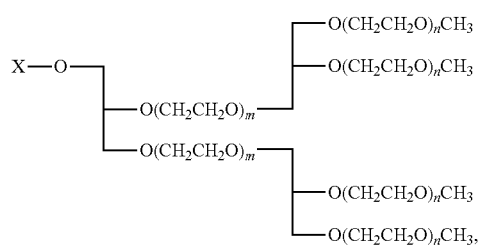

where X is N-hydroxysuccinimide and the PEG arms are of different molecular weights, for example, a 40 kD PEG of this architecture may be composed of 2 arms of 5 kD and 4 arms of 7.5 kD. Such PEG architecture may provide a compound with reduced viscosity compared to a similar aptamer conjugated to a two-armed PEG or a single-arm linear PEG.

In some cases, the reagent that may be used to generate PEGylated aptamers is a non-branched mPEG-Succinimidyl Propionate (mPEG-SPA), having the general formula:

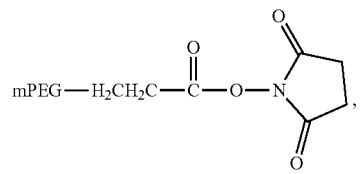

where mPEG is about 20 kD or about 30 kD. In one example, the reactive ester may be —O—CH$_2$—CH$_2$—CO$_2$—NHS.

In some instances, the reagent that may be used to generate PEGylated aptamers may include a branched PEG linked through glycerol, such as the Sunbright™ series from NOF Corporation, Japan. Non-limiting examples of these reagents include:

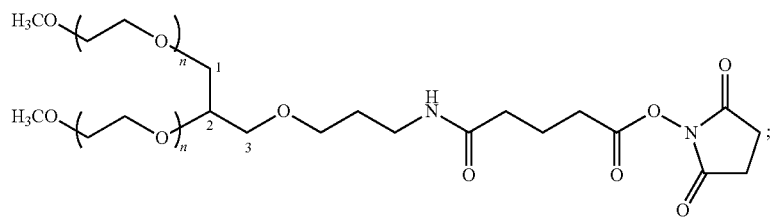

(SUNBRIGHT® GL2-400GS2)

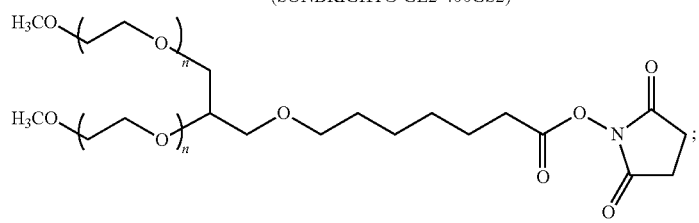

(SUNBRIGHT® GL2-400HS)

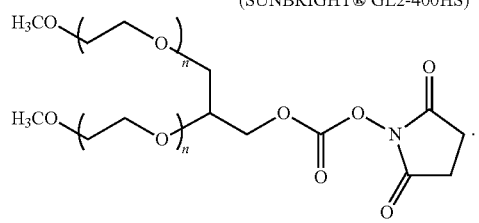

(SUNBRIGHT® GL2-400TS)

In another example, the reagents may include a non-branched mPEG Succinimidyl alpha-methylbutanoate (mPEG-SMB) having the general formula:

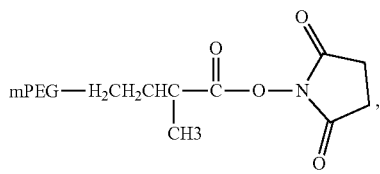

where mPEG is between 10 and 30 kD. In one example, the reactive ester may be —O—CH$_2$—CH$_2$—CH(CH$_3$)—CO$_2$—NHS.

In other instances, the PEG reagents may include nitrophenyl carbonate-linked PEGs, having the general formula:

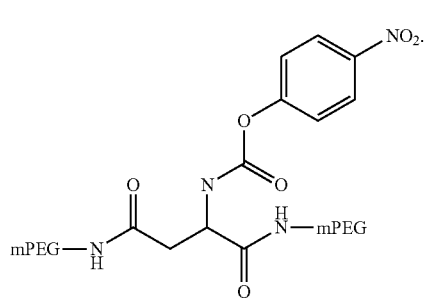

Compounds including nitrophenyl carbonate can be conjugated to primary amine containing linkers.

In some cases, the reagents used to generate PEGylated aptamers may include PEG with thiol-reactive groups that can be used with a thiol-modified linker. One non-limiting example may include reagents having the following general structure:

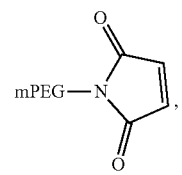

where mPEG is about 10 kD, about 20 kD or about 30 kD. Another non-limiting example may include reagents having the following general structure:

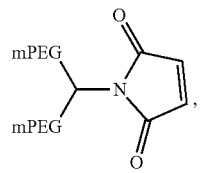

where each mPEG is about 10 kD, about 20 kD, or about 30 kD and the total molecular weight is about 20 kD, about 40 kD, or about 60 kD, respectively. Branched PEGs with thiol reactive groups that can be used with a thiol-modified linker, as described above, may include reagents in which the branched PEG has a total molecular weight of about 40 kD or about 60 kD (e.g., where each mPEG is about 20 kD or about 30 kD).

In some cases, the reagents used to generated PEGylated aptamers may include reagents having the following structure:

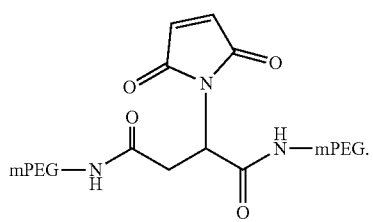

In some cases, the reaction is carried out between about pH 6 and about pH 10, or between about pH 7 and pH 9 or about pH 8.

In some cases, the aptamer is associated with a single PEG molecule. In other cases, the aptamer is associated with two or more PEG molecules.

In some cases, the aptamers described herein may be bound or conjugated to one or more molecules having desired biological properties. Any number of molecules can be bound or conjugated to aptamers, non-limiting examples including antibodies, peptides, proteins, carbohydrates, enzymes, polymers, drugs, small molecules, gold nanoparticles, radiolabels, fluorescent labels, dyes, haptens (e.g., biotin), other aptamers, or nucleic acids (e.g., siRNA). In some cases, aptamers may be conjugated to molecules that increase the stability, the solubility or the bioavailability of the aptamer. Non-limiting examples include polyethylene glycol (PEG) polymers, carbohydrates and fatty acids. In some cases, molecules that improve the transport or delivery of the aptamer may be used, such as cell penetration peptides. Non-limiting examples of cell penetration peptides can include peptides derived from Tat, penetratin, polyarginine peptide Args sequence (SEQ ID NO: 90), Transportan, VP22 protein from Herpes Simplex Virus (HSV), antimicrobial peptides such as Buforin I and SynB, polyproline sweet arrow peptide molecules, Pep-1 and MPG. In some embodiments, the aptamer is conjugated to a lipophilic compound such as cholesterol, dialkyl glycerol, diacyl glycerol, or a non-immunogenic, high molecular weight compound or polymer such as polyethylene glycol (PEG) or other water-soluble pharmaceutically acceptable polymers including, but not limited to, polyaminoamines (PAMAM) and polysaccharides such as dextran, or polyoxazolines (POZ).

The molecule to be conjugated can be covalently bonded or can be associated through non-covalent interactions with the aptamer of interest. In one example, the molecule to be conjugated is covalently attached to the aptamer. The covalent attachment may occur at a variety of positions on the aptamer, for example, to the exocyclic amino group on the base, the 5-position of a pyrimidine nucleotide, the 8-position of a purine nucleotide, the hydroxyl group of the phosphate, or a hydroxyl group or other group at the 5' or 3' terminus. In one example, the covalent attachment is to the 5' or 3' hydroxyl group of the aptamer.

In some cases, the aptamer can be attached to another molecule directly or with the use of a spacer or linker. For example, a lipophilic compound or a non-immunogenic, high molecular weight compound can be attached to the aptamer using a linker or a spacer. Various linkers and attachment chemistries are known in the art. In a non-limiting example, 6-(trifluoroacetamido)hexanol (2-cyanoethyl-N,N-diisopropyl)phosphoramidite can be used to add a hexylamino linker to the 5' end of the synthesized aptamer. This linker, as with the other amino linkers provided herein, once the group protecting the amine has been removed, can be reacted with PEG-NHS esters to produce covalently linked PEG-aptamers. Other non-limiting examples of linker phosphoramidites may include: TFA-amino C4 CED phosphoramidite having the structure:

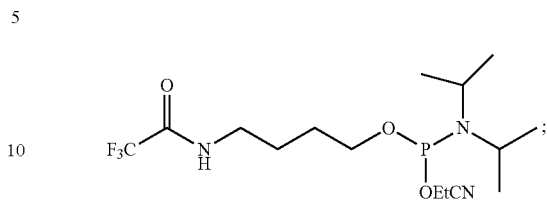

5'-amino modifier C3 TFA having the structure:

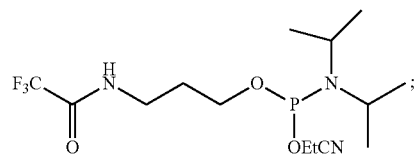

MT amino modifier C6 CED phosphoramidite having the structure:

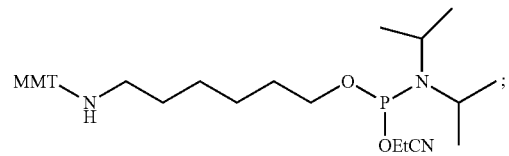

5'-amino modifier 5 having the structure:

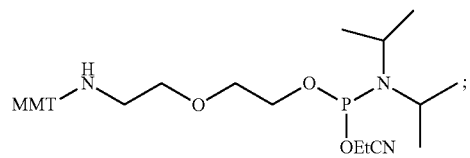

MMT: 4-Monoethoxytrityl

5'-amino modifier C12 having the structure:

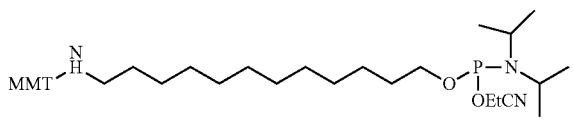

MMT: 4-Monoethoxytrityl and 5' thiol-modifier C6 having the structure:

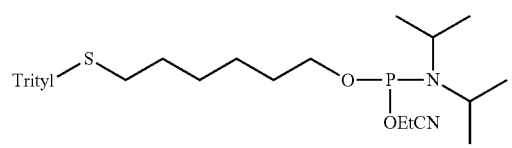

The 5'-thiol modified linker may be used, for example, with PEG-maleimides, PEG-vinylsulfone, PEG-iodoacetamide and PEG-orthopyridyl-disulfide. In one example, the aptamer may be bonded to the 5'-thiol through a maleimide or vinyl sulfone functionality.

In some cases, the aptamer formulated according to the present disclosure may also be modified by encapsulation within aliposome. In other cases, the aptamer formulated according to the present disclosure may also be modified by encapsulation within a micelle. Liposomes and micelles may be comprised of any lipids, and in some cases the lipids may be phospholipids, including phosphatidylcholine.

In some cases, the aptamers described herein are designed to inhibit a function associated with an alternative complement pathway enzyme. In one example, an anti-fD aptamer is used to inhibit a function associated with fD (e.g., inhibit the catalytic activity off fD). In other cases, the aptamers described herein are designed to prevent an interaction or binding of two or more proteins of the alternative complement pathway. In one example, an aptamer binds to fD and prevents binding of the complex C3bBb to fD. The aptamers described herein may bind to a region of fD that is recognized by an antibody or antibody fragment thereof that inhibits a function associated with fD. In some cases, the antibody or antibody fragment thereof that inhibits a function associated with fD has an amino acid sequence of heavy chain variable region of (SEQ ID NO: 71)
EVQLVQSGPELKKPGASVKVSCKASGYTFTNYGMNWVRQAPGQGLEWMGW

INTYTGETTYADDFKGRFVFSLDTSVSTAYLQISSLKAEDTAVYYCERGG

VNNWGQGTLVTVSSASTKGPSVFPLAPSSKSTSGGTAALGCLVKDYFPEP

VTVSWNSGALTSGVHTFPAVLQSSGLYSLSSVVTVPSSSLGTQTYICNVN

HKPSNTKVDKKVEPKSCDKTHT and an amino acid sequence of light chain variable region of:

(SEQ ID NO: 72)
DIQVTQSPSSLSASVGDRVTITCITSTDIDDDMNYQQKPGKVPKLLISG

GNTLRPGVPSRFSGSGSGTDFTLTISSLQPEDVATYYCLQSDSLPYTFGQ

GTKVEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC.

In some cases, the antibody or antibody fragment thereof that inhibits a function associated with fD has an amino acid sequence of heavy chain variable region of:

(SEQ ID NO: 85)
EVQLVQSGPELKKPGASVKVSCKASGYTFTNYGMNWVRQAPGQGLEWMGW

INTYTGETTYAEDFKGRFVFSLDTSVSTAYLQISSLKAEDTAVYYCEREG

GVSNWGQGTLVTVSS;
or (SEQ ID NO: 86)
EVQLVQSGPELKKPGASVKVSCKASGYTFTNYGMNWVRQAPGQGLEWMGW

INTYTGETTYAEDFKGRFVFSLDTSVSTAYLQISSLKAEDTAVYYCEREG

GVNNWGQGTLVTVSS, and an amino acid sequence of light chain variable region of:

(SEQ ID NO: 87)
DIQVTQSPSSLSASVGDRVTITCITSTDIESDMNAVYQQKPGKVPKLLIS

GGNTLRPGVPSRFSGSGSGTDFTLTISSLQPEDVATYYCLQSDSLPYTFG

QGTKVEIK;

(SEQ ID NO: 88)
DIQVTQSPSSLSASVGDRVTITCITSTDIESDMNWYQQKPGKVPKLLISG

GNTLRPGVPSRFSGSGSGTDFTLTISSLQPEDVATYYCLQSESLPYTFGQ

GTKVEIK;
or (SEQ ID NO: 89)
DIQVTQSPSSLSASVGDRVTITCITSTSIESDMNWYQQKPGKVPKLLISG

GNTLRPGVPSRFSGSGSGTDFTLTISSLQPEDVATYYCLQSDSLPYTFGQ

GTKVEIK.

The aptamers described herein may bind to a region of fD that is recognized by a small molecule inhibitor that inhibits a function associated with fD, non-limiting examples including dichloroisocoumarin or any one of the compounds depicted in FIGS. 13A-D. The aptamers described herein may bind to a region of fD that is recognized by a peptide inhibitor that inhibits a function associated with fD.

In some cases, an aptamer of the disclosure comprises one of the following sequences described in Table 1.

TABLE 1

| fD Aptamer Sequences | | | |
|---|---|---|---|
| SEQ NO. | ID Aptamer Number | Back-bone | Sequence 5' to 3' |
| SEQ ID NO: 1 | Aptamer 1 | RNA | GGGAGUGUGUACGAGGCAUUAGGCCGCCAC CCAAACUGCAGUCCUCGUAAGUCUGCCUGG CGGCUUUGAUACUUGAUCGCCCUAGAAGC |
| SEQ ID NO: 2 | Aptamer 2 | RNA | GGGAGUGUGUACGAGGCAUUAGUCCGCCGA AGUCUUUUGGCUCGGUUUUUUCAAGGUCGG CGGCUUUGAUACUUGAUCGCCCUAGAAGC |
| SEQ ID NO: 3 | Aptamer 3 | RNA | GGGAGUGUGUACGAGGCAUUAGGCCGCCAC CUCGUUUGAUUGCGGUUGUUCGGCCGCGGG CGGCUUUGAUACUUGAUCGCCCUAGAAGC |
| SEQ ID NO: 4 | Aptamer 4 | DNA | GTGACGACTGACATATCTGCTCCGAGGTTA TTGGGGTTGGGGCCTGGGCGATTGGGGCCT CGTAGTTGAGTCTGAGTGCT |
| SEQ ID NO: 5 | Aptamer 5 | DNA | GTGACGACTGACATATCTGCGTTTGGGGTT GGGGCCTGGGAGTTTGGGGAGCAGAAGGA CGTAGTTGAGTCTGAGTGCT |
| SEQ ID NO: 6 | Aptamer 6 | DNA | GTGACGACTGACATATCTGCTGTGGGTGTT GTGGGGTGGGTGGTGGGCCCTTCGCCATG CGTAGTTGAGTCTGAGTGCT |
| SEQ ID NO: 7 | Aptamer 7 | DNA | GTGACGACTGACATATCTGCGGCGGTTGGG GTCGAAGGGCGAGGGGTGGGAGGTCGCCGT AGTTGAGTCTGAGTGCT |
| SEQ ID NO: 8 | Aptamer 8 | DNA | GTGACGACTGACATATCTGCTATTTTGGGG CCTGGGTGTTGGGGATTGGGGACTATGTGT CGTAGTTGAGTCTGAGTGCT |
| SEQ ID NO: 9 | Aptamer 9 | DNA | GTGACGACTGACATATCTGCTGTGGATGGT GGGGGGTGGTGTGGGAGGGCTGGTCGGTCG CGTAGTTGAGTCTGAGTGCT |

TABLE 1-continued fD Aptamer Sequences

| SEQ ID NO. | Aptamer Number | Backbone | Sequence 5' to 3' |
|---|---|---|---|
| SEQ ID NO: 10 | Aptamer 10 | DNA | GTGACGACTGACATATCTGCCCTATAGGGG TGTGGGCGAGGGGTGGGTGGTAGGGCGGCT CGTAGTTGAGTCTGAGTGCT |
| SEQ ID NO: 11 | Aptamer 11 | DNA | GTGACGACTGACATATCTGCGGAGGTGGGT GGGTGGGTGCGTGCGAGGGCGGTGTAGGTC CGTAGTTGAGTCTGAGTGCT |
| SEQ ID NO: 12 | Aptamer 12 | DNA | GTGACGACTGACATATCTGCAAAAGTTAGA TTGACATGGTATGCACCGTCTGAGGTTGGT CGTAGTTGAGTCTGAGTGCT |
| SEQ ID NO: 13 | Aptamer 13 | DNA | GTGACGACTGACATATCTGCACCACGCTAG GGGTGAGGGCGAGGGGTGGGTAGCGCGTGG CGTAGTTGAGTCTGAGTGCT |
| SEQ ID NO: 14 | Aptamer 14 | DNA | GTGACGACTGACATATCTGCTGTGGGTGTT GTGGGGGCGGGTGGTGGGTGCGTCGGTGGT CGTAGTTGAGTCTGAGTGCT |
| SEQ ID NO: 15 | Aptamer 15 | DNA | GTGACGACTGACATATCTGCTGCTTCCAGC GGTCATGATATGCACTGTCTGAAGCTCGGT CGTAGTTGAGTCTGAGTGCT |
| SEQ ID NO: 16 | Aptamer 16 | DNA | GTGACGACTGACATATCTGCTGTGTTATGA TATGCACCGTCTGAGGGTAGTCGCGGGGTG CGTAGTTGAGTCTGAGTGCT |
| SEQ ID NO: 17 | Aptamer 17 | DNA | GTGACGACTGACATATCTGCTGCTTGTTTA GTGGGTGGGTGGGTGGTGTGGTGGTGATGC GTAGTTGAGTCTGAGTGCT |
| SEQ ID NO: 18 | Aptamer 18 | DNA | GTGACGACTGACATATCTGCCTTGGGGTTG GGGCCTGGGTGTTTGGGGTGGCCTAGAAGT CGTAGTTGAGTCTGAGTGCT |
| SEQ ID NO: 19 | Aptamer 19 | DNA | GTGACGACTGACATATCTGCGCTAGGGGTG GGTTGGGGTTGGTGGTGTGCGTGTGGGTTG CGTAGTTGAGTCTGAGTGCT |
| SEQ ID NO: 20 | Aptamer 20 | DNA | GTGACGACTGACATATCTGCTGTTGAGGTT GGTGGGGGGTGGGCGGTGGGATGGTTGTGC CGTAGTTGAGTCTGAGTGCT |
| SEQ ID NO: 21 | Aptamer 21 | DNA | GTGACGACTGACATATCTGCTTGACAGTCT GCTTTGCAGGGGCCGAGAGCGCCATTGCGT CGTAGTTGAGTCTGAGTGCT |
| SEQ ID NO: 22 | Aptamer 22 | DNA | GTGACGACTGACATATCTGCTGTGGTTGGT GGGGGGTGGAGGGTGGAGGCCGTGTGTCC CGTAGTTGAGTCTGAGTGCT |
| SEQ ID NO: 23 | Aptamer 23 | DNA | GTGACGACTGACATATCTGCTGTGGTGGTG GGGGAGGGTGGTGGGGTGGCCGGCGCTCGT CGTAGTTGAGTCTGAGTGCT |
| SEQ ID NO: 24 | Aptamer 24 | DNA | GTGACGACTGACATATCTGCTGGGTTACGT GGTTCGGGGCTAGGGGGGTGGGGTGTGTTT CGTAGTTGAGTCTGAGTGCT |
| SEQ ID NO: 25 | Aptamer 25 | DNA | GTGACGACTGACATATCTGCTGGTGGTGTG CGGTGGGTTCTTGGGTGGGATGGGTGGTAC CGTAGTTGAGTCTGAGTGCT |
| SEQ ID NO: 26 | Aptamer 26 | DNA | GTGACGACTGACATATCTGCTATTAGATCC TCGGTGGGTGGGTGGGTGTGTGGTGGTGTG CGTAGTTGAGTCTGAGTGCT |
| SEQ ID NO: 27 | Aptamer 27 | DNA | GTGACGACTGACATATCTGCGGGCGTCTGA GCGCATGGATGACCCACCGACAGATTGCGG CGTAGTTGAGTCTGAGTGCT |
| SEQ ID NO: 28 | Aptamer 28 | DNA | GTGACGACTGACATATCTGCGCTTTGGGTG GGCTCGGTGTGCGGTGTGCGGGTGGGTTTG CGTAGTTGAGTCTGAGTGCT |
| SEQ ID NO: 29 | Aptamer 29 | DNA | GTGACGACTGACATATCTGCGTTTGGGGTT GGGGCCTGGGAGTTTGGGGAGCAGAAAGGG CGTAGTTGAGTCTGAGTGCT |
| SEQ ID NO: 30 | Aptamer 30 | DNA | GTGACGACTGACATATCTGCGGGTGGGTTG GGTTGGGTTTGGTGGTGGTGCCTGTTAGTT CGTAGTTGAGTCTGAGTGCT |
| SEQ ID NO: 31 | Aptamer 31 | DNA | GTGACGACTGACATATCTGCAGGTGGGTGG GTGGGTGTGTGCGGTGGTGTGATTTGGC CGTAGTTGAGTCTGAGTGCT |
| SEQ ID NO: 32 | Aptamer 32 | DNA | GTGACGACTGACATATCTGCTGTGGTTGGT GGGGGCGGCGGGTGGGGAGCCTGGTGTTC CGTAGTTGAGTCTGAGTGCT |
| SEQ ID NO: 33 | Aptamer 33 | DNA | GTGACGACTGACATATCTGCTCCCGTTTGA GGGCTTGTCGGACAGATTGCTGGCACGTCA CGTAGTTGAGTCTGAGTGCT |
| SEQ ID NO: 34 | Aptamer 34 | DNA | GTGACGACTGACATATCTGCTCTTGGTGGT GGTGGTGGGTTGGGATGGGTCTTGGGCTGC CGTAGTTGAGTCTGAGTGCT |
| SEQ ID NO: 35 | Aptamer 35 | DNA | GTGACGACTGACATATCTGCCTGTGAGGGG AGGGAGGGTGGGTTTGGCGGTGGCGCAGGC CGTAGTTGAGTCTGAGTGCT |
| SEQ ID NO: 36 | Aptamer 36 | DNA | GTGACGACTGACATATCTGCGTGGTGGTGC GTGGGTGGTGGGGGGGGAGCTGGGTGCCC CGTAGTTGAGTCTGAGTGCT |
| SEQ ID NO: 37 | Aptamer 37 | DNA | GTGACGACTGACATATCTGCTGTGGGTGTT GTGGGGGTGGGTGGTGGGCCCTTCGCCGTG CGTAGTTGAGTCTGAGTGCT |
| SEQ ID NO: 38 | Aptamer 38 | DNA | GTGACGACTGACATATCTGCTTCCGGTATG TGTGGGTGGGTGGGTGGTGTGGTGGTGTTG CGTAGTTGAGTCTGAGTGCT |
| SEQ ID NO: 39 | Aptamer 39 | DNA | GTGACGACTGACATATCTGCTCTCTTCTGT TGTGGGTGGGTGGGTGGTGTGGTGCGTGTG CGTAGTTGAGTCTGAGTGCT |
| SEQ ID NO: 40 | Aptamer 40 | DNA | GTGACGACTGACATATCTGCGGCTGGGTGG GTTGGGTTAGGGTGGTGCCGGTGGGTTGC CGTAGTTGAGTCTGAGTGCT |
| SEQ ID NO: 41 | Aptamer 41 | DNA | GTGACGACTGACATATCTGCGTTTAGGTGG GCGGGTGGGTGTGCGGTGGGCGGTGTTGAA CGTAGTTGAGTCTGAGTGCT |
| SEQ ID NO: 42 | Aptamer 42 | DNA | GTGACGACTGACATATCTGCGGTGATTGGG GTTGGGGCCTGGGCGTTTGGGGACCGCATG CGTAGTTGAGTCTGAGTGCT |
| SEQ ID NO: 43 | Aptamer 43 | DNA | GTGACGACTGACATATCTGCGTTTGGGGTT GGGGCCTGGGAGTTTGGGGAGCAGAGAGGA CGTAGTTGAGTCTGAGTGCT |
| SEQ ID NO: 44 | Aptamer 44 | DNA | GTGACGACTGACATATCTGCTAACTTGTTG GGGTTTGGGGCCTGGGTGTTGGGGTTGTTT CGTAGTTGAGTCTGAGTGCT |
| SEQ ID NO: 45 | Aptamer 45 | DNA | GTGACGACTGACATATCTGCTGGGGTTGGT GGGGGAGGTGGGTGGGTTATGTGCGCTGGG CGTAGTTGAGTCTGAGTGCT |

TABLE 1-continued fD Aptamer Sequences

| SEQ ID NO. | Aptamer Number | Back-bone | Sequence 5' to 3' |
|---|---|---|---|
| SEQ ID NO: 46 | Aptamer 46 | DNA | GTGACGACTGACATATCTGCTGTGGGTGTTGTGGGGGTGGGTTGGTGGGCATTGCGTGTGCGTAGTTGAGTCTGAGTGCT |
| SEQ ID NO: 47 | Aptamer 47 | DNA | GTGACGACTGACATATCTGCGAGTGGGTTCGGTGGTGGTGTGTGGGAGGGTTGGGTACGTCGTAGTTGAGTCTGAGTGCT |
| SEQ ID NO: 48 | Aptamer 48 | DNA | GTGACGACTGACATATCTGCTGGACATGATTGCACCGTATGAGGTTTAGTCGTTAATGTGCGTAGTTGAGTCTGAGTGCT |
| SEQ ID NO: 49 | Aptamer 49 | DNA | GTGACGACTGACATATCTGCAGTGGGGCCTGGGCGTTGGGGTTTGGGGTGCCTCGTCAGTCGTAGTTGAGTCTGAGTGCT |
| SEQ ID NO: 50 | Aptamer 50 | DNA | GTGACGACTGACATATCTGCATGGATTTTCGGTGGGTGGGTGGGTTGGTGTGGTGGTGTGCGTAGTTGAGTCTGAGTGCT |
| SEQ ID NO: 51 | Aptamer 51 | DNA | GTGACGACTGACATATCTGCTGTGGTTGGTGGGGGGTGGGTGGTGGGAAGGTTCCGGTGCCGTAGTTGAGTCTGAGTGCT |
| SEQ ID NO: 52 | Aptamer 52 | DNA | GTGACGACTGACATATCTGCGGTTGGGGTTGGGGCCTGGGTGTTGGGGAGCAGGTAGCACCGTAGTTGAGTCTGAGTGCT |
| SEQ ID NO: 53 | Aptamer 53 | DNA | GTGACGACTGACATATCTGCGGCCTGGGAGGGTTCGGTGGTGGTGCGAGGGTGGGCAAGCCGTAGTTGAGTCTGAGTGCT |
| SEQ ID NO: 54 | Aptamer 54 | DNA | ACCTAGTTTGGCTTGCAXAAGTAACYAGCACGTGGGCTAG |
| SEQ ID NO: 55 | Aptamer 55 | DNA | ACGATCGCCCCYGTCTWTAAGAXCGAATACTATGGGCTAG |
| SEQ ID NO: 56 | Aptamer 56 | DNA | ACCTAGAAAGGCTTAGTGAAGTAAWGATCAGGGCGGGATC |
| SEQ ID NO: 57 | Aptamer 57 | DNA | ACCTAGTTCCCYGTCTAXYAGAXCCGAGXGTATGCCGATC |
| SEQ ID NO: 58 | Aptamer 58 | DNA | ACCTAGGCAGTCTTGCCGAATTTACGAGXGGGGAGGGATC |
| SEQ ID NO: 59 | Aptamer 59 | DNA | ACGATCACTGCYCAGCWTYATTAACYAGCYTCGACCCTAG |
| SEQ ID NO: 60 | Aptamer 60 | DNA | ACGATCTTCCGCCAGCTGYATTXCGAAGXGCGTGAGGATC |
| SEQ ID NO: 61 | Aptamer 61 | DNA | ACCTAGGCGGTCTTXCCGTCGTTACGTCCYCGGCCCCTAG |
| SEQ ID NO: 62 | Aptamer 62 | DNA | ACCTAGTTTGGCGTAGCGYATTAAWGGGXGCGGCAGCTAG |
| SEQ ID NO: 63 | Aptamer 63 | DNA | ACGATCGCTGACGTXCAXYAGTATGAGGCACGTGGGCTAG |

In some aspects, an aptamer of the disclosure comprises the nucleic acid sequence of any one of Aptamers 1-3 (SEQ ID NOS: 1-3). In some cases, any one of Aptamers 1-3 comprises one or more modified nucleotides. In a preferred example, an aptamer of the disclosure comprises one of Aptamers 1-3 where G is 2'F and A, C and U are 2'OMe modified RNA. In some aspects, an aptamer of the disclosure comprises the nucleic acid sequence of any one of Aptamers 54-63 (SEQ ID NOS: 54-63). In some cases, any one of Aptamers 54-63 comprises one or more modified nucleotides. In a preferred example, an aptamer of the disclosure comprises one of Aptamers 54-63, where W=5-(indole-3-acetamido-1-propenyl)-2'-deoxyuridine; X=5-(amino-1-propenyl)-2'-deoxyuridine; and Y=5-(4-pivaloyl-benzamido-1-propenyl)-2'-deoxyuridine.

In some cases, an aptamer of the disclosure may have at least 80%, 81%, 82%, 83%, 84%, 85%, 86%, 87%, 88%, 89%, 90%, 91%, 92%, 93%, 94%, 95%, 96%, 97%, 98%, or 99% sequence identity with any aptamer described herein. For example, an anti-fD aptamer of the disclosure may have at least 80%, 81%, 82%, 83%, 84%, 85%, 86%, 87%, 88%, 89%, 90%, 91%, 92%, 93%, 94%, 95%, 96%, 97%, 98%, or 99% sequence identity with any aptamer described in Table 1. In some cases, an aptamer of the disclosure may have at least 80%, 81%, 82%, 83%, 84%, 85%, 86%, 87%, 88%, 89%, 90%, 91%, 92%, 93%, 94%, 95%, 96%, 97%, 98%, or 99% sequence homology with any aptamer described herein. For example, an anti-fD aptamer of the disclosure may have at least 80%, 81%, 82%, 83%, 84%, 85%, 86%, 87%, 88%, 89%, 90%, 91%, 92%, 93%, 94%, 95%, 96%, 97%, 98%, or 99% sequence homology with any aptamer described in Table 1.

In such cases where specific nucleotide modifications have been recited, it should be understood that any number and type of nucleotide modifications may be substituted. For example, 2'OMeG may be substituted for 2'FG. Non-limiting examples of nucleotide modifications have been provided herein. In some instances, all of the nucleotides of an aptamer are modified. In some instances, at least 50%, 55%, 60%, 65%, 70%, 75%, 80%, 85%, 86%, 87%, 88%, 89%, 90%, 91%, 92%, 93%, 94%, 95%, 96%, 97%, 98%, 99%, or 100% of the nucleotides of an aptamer of the disclosure may be modified.

In some instances, the aptamer does not comprise any one of the following nucleic acid sequences (from 5' to 3'):

(SEQ ID NO: 73)
ACGGAGAAAGAGAGAGTGTAATTGCTAGCATAACCGCTGC, (SEQ ID NO: 74)
GTAACCACGTTGCCAGACCGAGTCTACCAGCGATCCTCAG, (SEQ ID NO: 75)
TATGCCCAAATCCCTCAAGTCGGCCAGGATACACCACCGT, (SEQ ID NO: 76)
AATCAAAAGGCTCACGCGCGGATTGGTCAACCTTACAACC, (SEQ ID NO: 77)
TCGGCCTTCCCAGACCACCGCAATCCCCAGGGAACAGGCA, (SEQ ID NO: 78)
CATCACACTGTCAACATACCCAGCCTGGGGAAAGACGAAC, (SEQ ID NO: 79)
AACCCGCATGCCGATCGATGTCGTGCCTCGCTCCACGCTC, or (SEQ ID NO: 80)
ACCAGGCACCCGACGGACTAACTCATCACTCAGGCGAGGG

Anti-fD Compositions fD is a component of the alternative complement pathway and is believed to be involved in the pathogenesis of AMD and other ocular disorders. fD is unique among serine proteases in that it does not require cleavage of a zymogen for expression of proteolytic activity. Rather, fD requires a conformational change that is believed to be induced by the complex C3bB resulting in a reversible reorientation of the catalytic center and substrate binding site of fD. fD is primarily produced by adipocytes and is systemically available in serum at low levels. fD contains a self-inhibitory loop that prevents catalytic activity of fD. Binding of the C3bB complex to fD displaces the self-inhibitory loop and fD cleaves C3bB to form the C3 convertase C3bBb. The catalytic activity of fD only occurs in the context of complexed fB; fD does not cleave uncomplexed fB. The complex of fD, fB, and C3b forms an amplification loop of the alternative complement pathway of which fD is the rate-limited enzyme.

In some aspects, the methods and compositions described herein involve inhibition of fD, resulting in inhibition of the amplification step of the alternative complement pathway. The anti-fD compositions herein may involve the use of one or more anti-fD aptamers for the treatment of ocular diseases. In some cases, the ocular disease is macular degeneration. In some cases, macular degeneration is age-related macular degeneration. In some cases, age-related macular degeneration is dry age-related macular degeneration. In some cases, dry age-related macular degeneration is advanced dry age-related macular degeneration (i.e., geographic atrophy). In some cases, age-related macular degeneration is wet age-related macular degeneration. In some cases, macular degeneration is Stargardt disease or Stargardt-like disease.

Anti-fD Inhibitors

The anti-fD compositions disclosed herein may be designed to bind to specific regions of fD with high specificity and affinity. The compositions may bind to fD in such a way as to inhibit, either directly or indirectly, the catalytic activity of the enzyme. In some cases, the anti-fD aptamers can bind to the active site (e.g., the catalytic cleft) of fD and directly inhibit the catalytic activity of fD. In this example, the aptamer may be designed to target the active site (e.g., the catalytic cleft) of fD. When the aptamer is bound to the active site of fD, it can prevent the substrate (e.g., C3bB) from accessing the active site. In some cases, the anti-fD aptamer can bind to an exosite of fD and indirectly inhibit the catalytic activity of fD by e.g., preventing the binding of C3bB. In some cases, the exosite may be remote from the catalytic site. In other cases, there may be some overlap with the catalytic site. In some cases the anti-fD aptamer can bind to the self-inhibitory loop of fD to prevent displacement of the self-inhibitory loop and thus, prevent activation of fD.

Amino acid residues of fD may be referenced according to the chymotrypsin numbering scheme and this numbering system is used throughout the disclosure to refer to specific amino acid residues of fD. Chymotrypsin numbering scheme for fD may be as depicted in FIG. 14 (SEQ ID NO: 94) (chymotrypsin numbering displayed above amino acid sequence and fD numbering scheme below amino acid sequence).

Anti-fD aptamers as described herein can modulate or inhibit the activity of fD or a fD variant thereof. A fD variant as used herein encompasses variants that perform essentially the same function as fD. A fD variant includes essentially the same structure as fD and in some cases includes at least 80%, 85%, 86%, 87%, 88%, 89%, 90%, 91%, 92%, 93%, 94%, 95%, 96%, 97%, 98%, 99%, 99.5%, or 99.9% sequence identity to the amino acid sequence (shown above) of the fD protein.

In certain embodiments of the disclosure, methods are provided for the identification of fD aptamers that specifically bind to epitopes of fD. These methods may be utilized, for example, to determine the binding site and/or the mechanism of action of the aptamer.

In one instance, methods are provided for testing a fD aptamer in alternative complement dependent hemolysis of red blood cells. Human serum that is rendered deficient in the classical complement pathway by depleting C1q may be dependent on alternative complement activity to lyse rabbit red blood cells, an activity that may be dependent on fD (Katschke, Wu, Ganesan, et al. (2012) Inhibiting alternative pathway complement activation by targeting the Factor D exosite. J. Biol. Chem. 287, 12886-12892). In some cases, the fD aptamers disclosed herein may inhibit alternative complement dependent hemolysis of red blood cells (see Example 4).

In another instance, methods are provided for testing a fD aptamer in fD esterase activity assays (see Example 5). Cleavage of a modified peptide substrate of fD, Z-lys-S-Bzl, may be monitored by the cleaved product reducing 5,5'-Dithiobis(2-nitrobenzoic acid). FD may have a lower catalytic rate than other complement proteases when using peptide thioester substrates, and one such substrate Z-lys-SBzl was found to be cleaved by fD and useful as a synthetic substrate (fD is called protein D in Kam, McRae et al. (1987) Human complement proteins D, C2, and B. J. Biol. Chem. 262, 3444-3451). In some cases, a molecule that binds fD may block catalytic activity by binding in the catalytic cleft to sterically prevent access of the peptide substrate to the catalytic residues of fD (Katschke, Wu, Ganesan, et al. (2012) Inhibiting alternative pathway complement activation by targeting the Factor D exosite. J. Biol. Chem. 287, 12886-12892). In other cases, a molecule that binds fD may block catalytic activity by an allosteric mechanism that induces structural changes in the enzyme. In yet other cases, a molecule that binds fD may bind to the fD exosite region to sterically inhibit binding of the physiologic substrate protein C3bB, but not of the synthetic modified peptide substrate Z-Lys-SBzl (Katschke, Wu, Ganesan, et al. (2012) Inhibiting alternative pathway complement activation by targeting the Factor D exosite. J. Biol. Chem. 287, 12886-12892). In some instances, where a molecule inhibits fD binding and proteolytic cleavage of FB but not Z-Lys-SBzl, the binding may be similar to how anti-factor D FAb antibody fragment binds to the exosite and induces a subtle conformational change that increases fD cleaving Z-Lys-S-Bzl (Katschke, Wu, Ganesan, et al. (2012) Inhibiting alternative pathway complement activation by targeting the Factor D exosite. J. Biol. Chem. 287, 12886-12892).

In another instance, methods are provided for testing a fD aptamer in a reconstituted biochemical fD activity assay which is composed of purified proteins fD, FB, and C3b (see Example 6). When fD binds to the complex of FB and C3b (C3bB), FB is cleaved by fD into fragments Ba and Bb (Katschke, Wu, Ganesan, et al. (2012) Inhibiting alternative pathway complement activation by targeting the Factor D exosite. J. Biol. Chem. 287, 12886-12892). The activity of fD can be monitored by the rate of FB cleavage and Ba fragment production using an ELISA that uses an antibody that specifically binds Ba (Quidel, A033), or by other means known in the art to measure Ba levels. In some cases, the concentrations of FB and C3b are equal so they form a 1:1 complex which can then bind fD and allow enzymatically active fD to cleave FB to fragments Ba and Bb. In some cases, the FB:C3b complex is present in 4-fold excess of fD. In other cases, the concentrations of fD and/or C3bB are varied in such a manner as to measure enzymatic constants, including, but not limited to $k_{cat}$, $K_m$ and $k_{cat}/K_m$.

In yet another instance, methods are provided for the identification of fD binding to C3bB in complex (see Example 7). FD is the rate-limiting enzyme in the alternative complement pathway, and converts the proconvertases C3bB and C3b2B to form the active C3 convertase C3bBb or the active C5 convertase C3bBb (Katschke et al 2012). For surface plasmon resonance (SPR) to detect fD in a stable complex with FB, catalytically inactive fD (S195A) may be used so that it does not cleave the FB upon binding to the FB:C3b complex (Katschke, Wu, Ganesan, et al. (2012) Inhibiting alternative pathway complement activation by targeting the Factor D exosite. J. Biol. Chem. 287, 12886-12892). When C3b is amine-coupled to a CM5 chip, SPR may detect binding of FB as increased mass, and binding of fD to the C3b:FB complex as a further increase in mass. In one aspect, the fD binding compounds are aptamers that bind fD and prevent fD binding to FB:C3b as determined by a reduced mass detected by SPR.

In some cases, a cell model of Stargardt disease may be used to detect activity of anti-fD aptamers (see Example 8). Retinal pigment epithelial (RPE) cells may undergo cell death early during the progress of Stargardt disease, and evidence points toward the involvement of the alternative complement pathway (AP) in RPE cell death (Berchuck, Yang, et al (2013) All-trans-retinal (atRal) sensitizes human RPE cells to alternative complement pathway-induced cell death. Invest Ophthalmol Vis Sci 54, 2669-2677). ARPE-19 cells are a spontaneously arising RPE cell line derived from the normal eyes of a 19-year-old male. The ARPE-19 cell line, established using the cuboidal basal cell layer cultured in specific culture media, expresses the RPE-specific markers cellular retinaldehyde binding protein and RPE-65. Stargardt disease is a hereditary juvenile macular degeneration that occurs in patients with homozygous mutations in the ABCA4 genes, which encode a protein that processes all-trans retinal (Molday (2007) ATP-binding cassette transporter ABCA4: molecular properties and role in vision and macular degeneration. J. Bioenerg Biomembr 39, 507-517). An ABCA4 and RDH8 mouse model of Stargardt disease presents with retinal pathology caused by accumulated atRal, and ABCA4 mutations are present in 16% of AMD patients, suggesting that elevated atRal may contribute to Stargardt disease and AMD disease progression (Berchuck et al 2013). Mechanistically, atRal decreased expression of CD46 and CD59 on RPE cells in vitro, which increased susceptibility to cell lysis mediated by alternative complement in response to anti-RPE antibody binding to the RPE cell membranes (Berchuck et al 2013). In some cases, the disclosure provides for the identification of fD inhibitors that inhibit alternative complement-mediated lysis of human retinal pigmented epithelial cells.

The anti-fD aptamers as disclosed herein, in some cases, may bind to the region of fD that includes the active site cleft. Upon activation by binding to C3bB, fD exhibits serine protease activity towards fB. Activation of fD by substrate binding is a two-step process: first, fD binds to fB in the open C3bB configuration at the Von Willebrand factor type-A (VWA)-serine protease (SP) interface of fB, interacting mainly via its exosite residues within loops 145-149, 169-173, 185-188 and 220-224. Binding of fD to C3bB causes the self-inhibitory loop of fD to be displaced from the active site cleft. The global architecture of fD is comprised of two anti-parallel beta barrel domains, each composed of six or seven beta strands that have the same topology in both domains. The beta-strands are connected by 14 turns/loops and three short alpha helices. The active site cleft is located within the loop formed between the two beta barrels, and encompasses structural elements including helix 1, loop 7 and beta-strand 7, loop 11 and beta-strand 11, beta-strand 12, loop 13 and beta-strand 13 (Jing et. al. 1998). Aptamers which bind the active site cleft could recognize any portion of the alpha helices, loops and beta strands which comprise the portion of fD within which the active site cleft resides, and by binding to this region, may prevent access to the active site cleft. Such residues include the catalytic triad, His57, Asp102 and Ser195, the oxyanion hole including the backbone amine of residue 193 and Ser195, the residues linking the catalytic triad to the oxyanion hole via a salt bridge including residue 16, 194 and Ser195, the S pocket, including residues 189-192, 214-216, and 224-228, as well as other elements of the specificity pocket including those residues comprising the S2, S3, S4 and Sn pockets. In particular, such aptamers would prevent interaction of P2-Pn residues of fB with specificity pockets S2-Sn of fD. In some cases, the aptamers as described herein specifically bind to the active site cleft or a region comprising the active site cleft of fD. Aptamers that are said to bind to the active site cleft or a region comprising the active site cleft may include any aptamers that bind to one or more of the regions including the catalytic triad (His57, Asp102 and Ser195); the oxyanion hole including the backbone amine of residue 193 and Ser195; the residues linking the catalytic triad to the oxyanion hole via a salt bridge including residue 16, 194 and Ser195; the S pocket, including residues 189-192, 214-216, and 224-228; as well as other elements of the specificity pocket including those residues comprising the S2, S3, S4 and Sn pockets.

Such fD inhibitors may inhibit alternative complement dependent hemolysis of red blood cells, may inhibit esterase activity of fD against thioester substrates of fD such as Z-Lys-S-Bzl, and may inhibit fB cleavage in the C3bB complex by fD. In esterase assays, such inhibitors may reduce $k_{cat}$ and increase $K_m$ of fD, with the primary effect decreasing $k_{cat}$ and decreasing $k_{cat}/K_m$ (Hedstrom). In complete biochemical assays, such inhibitors may decrease $k_{cat}$ and increase $K_m$, with a primary effect decreasing $k_{cat}$ and decreasing $k_{cat}/K_m$. Such inhibitors may not prevent formation of the enzyme-substrate complex (fD-C3bB complex) as assessed in enzymatic assays or enzyme-substrate assembly assays, such as surface plasmon resonance (SPR) assays described in Forneris et. al. or Katschke et. al., or similar E-S assembly assays assessed by ELISA or similar assays.

The anti-fD aptamers as disclosed herein, in some cases, may bind to the region of fD that includes the self-inhibitory loop (residues 212-218) and regions adjacent to the self-inhibitory loop, so as to stabilize the self-inhibited state of fD. Mature fD maintains a self-inhibited state through a set of conformations in the free fD state including the conformation of residues 212-218, which may be referred to as the self-inhibitory loop of fD. These residues may comprise portions of the polypeptide binding site as well as the S1 specificity pocket of fD. In the inactive state of fD, this loop is in an elevated conformation and forms specific bonds with key components of the catalytic triad and S1 specificity pocket, rendering fD inactive. In some cases, the anti-fD compounds of the disclosure are designed to target the self-inhibitory loop of fD to prevent the activation of fD. For example, the anti-fD compounds may bind to the self-inhibitory loop or to regions around the self-inhibitory loop to prevent displacement of the self-inhibitory loop from the active site cleft. In some cases, the anti-fD compounds may be designed to target residues 212-218 of fD. In cases where anti-fD aptamers bind to a region comprising one or more of amino acid residues 212-218 of fD, it may be said that such anti-fD aptamers bind to the self-inhibitory loop or a portion thereof of fD.

Such fD inhibitors may inhibit alternative complement dependent hemolysis of red blood cells, may inhibit esterase activity of fD against thioester substrates of fD such as Z-Lys-S-Bzl, and may inhibit fB cleavage in the C3bB complex by fD. In esterase assays, such inhibitors may reduce $k_{cat}$ and increase $K_m$ of fD, with the primary effect decreasing k and decreasing $k_{cat}/K_m$. In complete biochemical assays, such inhibitors may decrease $k_{cat}$ and increase $K_m$, with a primary effect decreasing $k_{cat}$ and decreasing $k_{cat}/K_m$. Such inhibitors may not prevent formation of the enzyme-substrate complex (fD-C3bB complex) as assessed in enzymatic assays or enzyme-substrate assembly assays, such as surface plasmon resonance (SPR) assays described in Forneris et. al. or Katschke et. al., or similar E-S assembly assays assessed by ELISA or similar assays.

The anti-fD aptamers as disclosed herein, in some cases, may bind to the exosite of fD so as to prevent formation of the ES complex. Without wishing to be bound by theory, the high specificity of fD for fB may be due to protein-protein interactions between the exosites of fD and fB. The exosite of fD is approximately 25 Å from the catalytic center and consists of 4 loops comprised by residues 145-149, 169-173, 185-188 and 220-224. In some cases, the anti-fD compounds of the disclosure may target the exosite of fD and prevent the interaction of fD with fB. Anti-fD compounds of this nature may target one or more of the 4 loops of the fD exosite, for example, the anti-fD compounds may be designed to target one or more of amino acid residues 145-149, 169-173, 185-188 and 220-224 of fD. In cases where an anti-fD aptamer binds to one or more of amino acid residues 145-149, 169-173, 185-188, and 220-224, it may be said that such aptamers bind to the exosite of fD.

Aptamer inhibitors that block binding of the C3bB substrate to fD may inhibit alternative complement dependent hemolysis of red blood cells. Such inhibitors may enhance the esterase activity of fD against thioester substrates of fD such as Z-Lys-S-Bzl, as observed for the anti-fD Fab's when bound to human fD (Katschke et. al.). Alternatively, aptamers which bind to the exosite of fD may not impact the esterase activity of fD, as for example, when the anti-fD Fab in Katschke et. al. binds fD from cynomolgus monkeys, it neither inhibits nor enhances fD esterase activity. Exosite binding aptamers would inhibit fB cleavage in the C3bB complex by fD. In esterase assays, such inhibitors may increase $k_{cat}$ and have no or minimal impact on $K_m$ of fD, with the primary effect increasing $k_{cat}$ and increasing $k_{cat}/K_m$, or such inhibitors would neither impact $k_{cat}$ or $K_m$ or $k_{cat}/K_m$. In complete biochemical assays, such inhibitors would primarily increase $K_m$ and decrease $k_{cat}/K_m$. Such inhibitors may prevent formation of the enzyme-substrate complex (fD-C3bB complex) as assessed in enzymatic assays or enzyme-substrate assembly assays, such as surface plasmon resonance (SPR) assays described in Forneris et. al. or Katschke et. al., or similar ES assembly assays assessed by ELISA or similar assays.

Catalytic turn-over of fD activation of fB requires dissociation of the ES complex if bound in a non-productive state or the EP (fD-C3bBb) complex upon fB cleavage. The anti-fD aptamers as disclosed herein, in some cases, may bind to fD in such a way as to prevent dissociation of fD from C3bB or C3bBb. As envisioned, such aptamers may bind near the exosite of fD and bind to fD in such a manner as to increase the affinity of fD for C3bB or C3bBb by decreasing the off-rate of this interaction. Such aptamers could be generated by selection against the fD-C3bB complex, by for example using a catalytically inactivated form of fD such as a mutant form in which Ser195 is mutated to Ala195 (Forneris et. al.), to provide a stable, non-reactive ES complex as a target for selection. Aptamers possessing such a mechanism of action would inhibit alternative complement dependent hemolysis of red blood cells. Such inhibitors may inhibit the esterase activity of fD against thioester substrates of fD such as Z-Lys-S-Bzl, or may not impact the esterase activity of fD. Such binding aptamers would inhibit the turn-over of fB cleavage in the C3bB complex by fD. In esterase assays, such inhibitors may decrease the $k_{cat}$ and have no or minimal impact on $K_m$ of fD, with the primary effect decreasing $k_{cat}$ and decreasing $k_{cat}/K_m$, or such inhibitors would neither impact $k_{cat}$ or $K_m$ or $k_{cat}/K_m$. In complete biochemical assays, such inhibitors would primarily decrease $K_{cat}$ and decrease $k_{cat}/K_m$. Such inhibitors would enhance formation of the enzyme-substrate complex (fD-C3bB complex) as assessed in enzymatic assays or enzyme-substrate assembly assays, such as surface plasmon resonance (SPR) assays described in Forneris et. al., and may increase the apparent affinity of fD for C3bB or C3bBb.

In some cases, an aptamer as described herein may bind the same epitope as an anti-fD antibody or antibody fragment thereof. In some cases, an aptamer as described herein may bind to the same epitope as an anti-fD therapeutic antibody. For example, the anti-fD aptamer may bind to the same or similar region of fD to that which an anti-fD therapeutic antibody such as an anti-fD Fab with an amino acid sequence of heavy chain variable region according to SEQ ID NO: 71 and an amino acid sequence of light chain variable region according to SEQ ID NO: 72; or an anti-fD Fab with an amino acid sequence of heavy chain variable region according to any one of SEQ ID NOS: 85 or 86 and an amino acid sequence of light chain variable region according to SEQ ID NOS: 87-89; or Mab 166-3 or LS-C135735 bind. For example, an anti-fD Fab with an amino acid sequence of heavy chain variable region according to SEQ ID NO: 71 and light chain variable region according to SEQ ID NO: 72 may bind residues 129-132, residues 164-178, Arg223 and Lys224, with the bulk of the interaction involving the loop encompassing amino acid 170 (the "170 loop"). In some cases, an aptamer that binds to the same or similar region of fD to that which an anti-fD Fab with an amino acid sequence of heavy chain variable region according to SEQ ID NO: 71 and light chain variable region according to SEQ ID NO: 72 binds (e.g., a region comprising one or more of amino acid residues 129-132, 164-178, Arg223 and Lys224) may be said to be binding to the exosite of fD.

In some cases, an anti-fD aptamer for the modulation of fD is provided. In some cases, an anti-fD aptamer for the inhibition of a function associated with fD is provided. In some cases, the anti-fD aptamer inhibits the catalytic activity of fD. In some cases, an anti-fD aptamer for the treatment of dry AMD or geographic atrophy is provided. In some cases, an anti-fD aptamer for the treatment of wet AMD is provided. In some cases, an anti-fD aptamer for the treatment of Stargardt disease is provided.

The dissociation constant ($K_d$) can be used to describe the affinity of an aptamer for a target (or to describe how tightly the aptamer binds to the target) or to describe the affinity of an aptamer for a specific epitope of a target (e.g., exosite, catalytic cleft, etc.). The dissociation constant is defined as the molar concentration at which half of the binding sites of a target are occupied by the aptamer. Thus, the smaller the $K_d$, the tighter the binding of the aptamer to its target. In some cases, an anti-fD aptamer has a dissociation constant ($K_d$) for fD protein of less than 1 mM, less than 100 μM, less than 10 μM, less than 1 μM, less than 100 nM, less than 10 nM, less than 1 nM, less than 500 pM, or less than 100 pM. In some cases, an anti-fD aptamer has a dissociation constant ($K_d$) for fD protein of less than 50 nM. In some cases, an anti-fD aptamer has a dissociation constant ($K_d$) for fD protein of less than 25 nM. In some cases, an anti-fD aptamer has a dissociation constant ($K_d$) for fD protein of less than 10 nM. In some cases, an anti-fD aptamer has a dissociation constant ($K_d$) for fD protein of less than 5 nM. In some cases, an anti-fD aptamer has a dissociation constant ($K_d$) for fD protein of less than 500 pM. In some cases, an anti-fD aptamer has a dissociation constant ($K_d$) for fD protein of less than 50 pM. In some cases, an anti-fD aptamer has a dissociation constant ($K_d$) for fD protein of less than 5 pM. In some cases, the aptamer binds to the catalytic cleft, the active site, the exosite, and/or the self-inhibitory loop of fD with a $K_d$ of less than about 1 mM, 100 µM, 10 µM, 1 µM, 100 nM, 50 nM, 25 nM, 10 nM, 5 nM, 500 pM, 50 pM, or 5 pM. In some cases, the $K_d$ is determined by a flow cytometry assay as described herein.

The aptamers disclosed herein may bind to the catalytic cleft of fD with a $K_d$ of less than about 50 nM and have an $IC_{50}$ of less than about 50 nM as measured by a C3 hemolysis assay. The aptamers disclosed herein may bind to the catalytic cleft of fD with a $K_d$ of less than about 50 nM and have an $IC_{50}$ of less than about 10 nM as measured by a C3 hemolysis assay. The aptamers disclosed herein may bind to the catalytic cleft of fD with a $K_d$ of less than about 50 nM and have an $IC_{50}$ of less than about 5 nM as measured by a C3 hemolysis assay. The aptamers disclosed herein may bind to the catalytic cleft of fD with a $K_d$ of less than about 10 nM and have an $IC_{50}$ of less than about 50 nM as measured by a C3 hemolysis assay. The aptamers disclosed herein may bind to the catalytic cleft of fD with a $K_d$ of less than about 10 nM and have an $IC_{50}$ of less than about 10 nM as measured by a C3 hemolysis assay. The aptamers disclosed herein may bind to the catalytic cleft of fD with a $K_d$ of less than about 10 nM and have an $IC_{50}$ of less than about 5 nM as measured by a C3 hemolysis assay. The aptamers disclosed herein may bind to the catalytic cleft of fD with a $K_d$ of less than about 5 nM and have an $IC_{50}$ of less than about 50 nM as measured by a C3 hemolysis assay. The aptamers disclosed herein may bind to the catalytic cleft of fD with a $K_d$ of less than about 5 nM and have an $IC_{50}$ of less than about 10 nM as measured by a C3 hemolysis assay. The aptamers disclosed herein may bind to the catalytic cleft of fD with a $K_d$ of less than about 5 nM and have an $IC_{50}$ of less than about 5 nM as measured by a C3 hemolysis assay.

The aptamers disclosed herein may bind to the active site of fD with a $K_d$ of less than about 50 nM and have an $IC_{50}$ of less than about 50 nM as measured by a C3 hemolysis assay. The aptamers disclosed herein may bind to the active site of fD with a $K_d$ of less than about 50 nM and have an $IC_{50}$ of less than about 10 nM as measured by a C3 hemolysis assay. The aptamers disclosed herein may bind to the active site of fD with a $K_d$ of less than about 50 nM and have an $IC_{50}$ of less than about 5 nM as measured by a C3 hemolysis assay. The aptamers disclosed herein may bind to the active site of fD with a $K_d$ of less than about 10 nM and have an $IC_{50}$ of less than about 50 nM as measured by a C3 hemolysis assay. The aptamers disclosed herein may bind to the active site of fD with a $K_d$ of less than about 10 nM and have an $IC_{50}$ of less than about 10 nM as measured by a C3 hemolysis assay. The aptamers disclosed herein may bind to the active site of fD with a $K_d$ of less than about 10 nM and have an $IC_{50}$ of less than about 5 nM as measured by a C3 hemolysis assay. The aptamers disclosed herein may bind to the active site of fD with a $K_d$ of less than about 5 nM and have an $IC_{50}$ of less than about 50 nM as measured by a C3 hemolysis assay. The aptamers disclosed herein may bind to the active site of fD with a $K_d$ of less than about 5 nM and have an $IC_{50}$ of less than about 10 nM as measured by a C3 hemolysis assay. The aptamers disclosed herein may bind to the active site of fD with a $K_d$ of less than about 5 nM and have an $IC_{50}$ of less than about 5 nM as measured by a C3 hemolysis assay.

The aptamers disclosed herein may bind to the exosite of fD with a $K_d$ of less than about 50 nM and have an $IC_{50}$ of less than about 50 nM as measured by a C3 hemolysis assay. The aptamers disclosed herein may bind to the exosite of fD with a $K_d$ of less than about 50 nM and have an $IC_{50}$ of less than about 10 nM as measured by a C3 hemolysis assay. The aptamers disclosed herein may bind to the exosite of fD with a $K_d$ of less than about 50 nM and have an $IC_{50}$ of less than about 5 nM as measured by a C3 hemolysis assay. The aptamers disclosed herein may bind to the exosite of fD with a $K_d$ of less than about 10 nM and have an $IC_{50}$ of less than about 50 nM as measured by a C3 hemolysis assay. The aptamers disclosed herein may bind to the exosite of fD with a $K_d$ of less than about 10 nM and have an $IC_{50}$ of less than about 10 nM as measured by a C3 hemolysis assay. The aptamers disclosed herein may bind to the exosite of fD with a $K_d$ of less than about 10 nM and have an $IC_{50}$ of less than about 5 nM as measured by a C3 hemolysis assay. The aptamers disclosed herein may bind to the exosite of fD with a $K_d$ of less than about 5 nM and have an $IC_{50}$ of less than about 50 nM as measured by a C3 hemolysis assay. The aptamers disclosed herein may bind to the exosite of fD with a $K_d$ of less than about 5 nM and have an $IC_{50}$ of less than about 10 nM as measured by a C3 hemolysis assay. The aptamers disclosed herein may bind to the exosite of fD with a $K_d$ of less than about 5 nM and have an $IC_{50}$ of less than about 5 nM as measured by a C3 hemolysis assay.

The aptamers disclosed herein may bind to the self-inhibitory loop of fD with a $K_d$ of less than about 50 nM and have an $IC_{50}$ of less than about 50 nM as measured by a C3 hemolysis assay. The aptamers disclosed herein may bind to the self-inhibitory loop of fD with a $K_d$ of less than about 50 nM and have an $IC_{50}$ of less than about 10 nM as measured by a C3 hemolysis assay. The aptamers disclosed herein may bind to the self-inhibitory loop of fD with a $K_d$ of less than about 50 nM and have an $IC_{50}$ of less than about 5 nM as measured by a C3 hemolysis assay. The aptamers disclosed herein may bind to the self-inhibitory loop of fD with a $K_d$ of less than about 10 nM and have an $IC_{50}$ of less than about 50 nM as measured by a C3 hemolysis assay. The aptamers disclosed herein may bind to the self-inhibitory loop of fD with a $K_d$ of less than about 10 nM and have an $IC_{50}$ of less than about 10 nM as measured by a C3 hemolysis assay. The aptamers disclosed herein may bind to the self-inhibitory loop of fD with a $K_d$ of less than about 10 nM and have an $IC_{50}$ of less than about 5 nM as measured by a C3 hemolysis assay. The aptamers disclosed herein may bind to the self-inhibitory loop of fD with a $K_d$ of less than about 5 nM and have an $IC_{50}$ of less than about 50 nM as measured by a C3 hemolysis assay. The aptamers disclosed herein may bind to the self-inhibitory loop of fD with a $K_d$ of less than about 5 nM and have an $IC_{50}$ of less than about 10 nM as measured by a C3 hemolysis assay. The aptamers disclosed herein may bind to the self-inhibitory loop of fD with a $K_d$ of less than about 5 nM and have an $IC_{50}$ of less than about 5 nM as measured by a C3 hemolysis assay.

In some aspects, the aptamers disclosed herein have an improved half-life as compared to other therapeutics, including antibodies. In some cases, the aptamers have an improved half-life in a biological fluid or solution as compared to an antibody. In some cases, the aptamers have an improved half-life in vivo as compared to an antibody. In one example, the aptamers have an improved half-life when injected into the eye (intraocular half-life) as compared to an antibody. In some cases, the aptamers may have an improved intraocular half-life when injected into the eye of a human. In some cases, the aptamers may demonstrate improved stability over antibodies under physiological conditions.

In some cases, the aptamers described herein have an intraocular half-life of at least 7 days in a human. In some cases, the aptamers described herein have an intraocular half-life of at least 8 days, at least 9 days, at least 10 days, at least 11 days, at least 12 days, at least 13 days, at least 14 days, at least 15 days, at least 20 days or greater in a human.

In some cases, the aptamers described herein have an intraocular half-life of at least 1 day in a non-human animal (e.g., rodent/rabbit/monkey). In some cases, the aptamers described herein have an intraocular half-life of at least 1 day, at least 2 days, at least 3 days, at least 4 days, at least 5 days, at least 6 days, at least 7 days, at least 8 days, at least 9 days, at least 10 days or greater in a non-human animal such as a rodent, rabbit or monkey.

In some aspects, the aptamers described herein may have a shorter half-life as compared to other therapeutics. For example, an unmodified or unconjugated aptamer may have a lower half-life as compared to a modified or conjugated aptamer, however, the low molecular weight of the unmodified or unconjugated forms may allow for orders of magnitude greater initial concentrations, thereby achieving greater duration/efficacy. In some examples, the aptamer may have an intraocular half-life of less than about 7 days in a human. In some examples, the aptamers described herein have an intraocular half-life of less than about 6 days, less than about 5 days or even less than about 4 days in a human.

The aptamers disclosed herein may demonstrate high specificity for fD versus other complement pathway components. Generally, the aptamer may be selected such that the aptamer has high affinity for fD, but with little to no affinity for other complement pathway components or serine proteases. In some cases, the aptamers bind to fD with a specificity of at least 5-fold, at least 10-fold, at least 15-fold, at least 20-fold, or greater than 20-fold greater than the aptamers bind to any of C3, C5, Factor B, Factor H or Factor I (or any of their related dimeric, trimeric, or multimeric complexes, units or subunits) at relative serum concentrations. For example, in some cases the aptamers bind to fD with a specificity of at least 50-fold greater than the aptamers bind to any of C3, C5, Factor B, Factor H or Factor I (or any of their related dimeric, trimeric, or multimeric complexes, units or subunits) at relative serum concentrations. For example, in some cases the aptamers bind to FD with a specificity of at least 100-fold greater than the aptamers bind to any of C3, C5, Factor B, Factor H or Factor I (or any of their related dimeric, trimeric, or multimeric complexes, units or subunits) at relative serum concentrations.

The activity of a therapeutic agent can be characterized by the half maximal inhibitory concentration ($IC_{50}$). The $IC_{50}$ is calculated as the concentration of therapeutic agent in nM at which half of the maximum inhibitory effect of the therapeutic agent is achieved. The $IC_{50}$ is dependent upon the assay utilized to calculate the value. In some examples, the $IC_{50}$ of an aptamer described herein is less than 100 nM, less than 50 nM, less than 25 nM, less than 10 nM, less than 5 nM, less than M, less than 0.5 nM, less than 0.1 nM or less than 0.01 nM as measured by a C3 hemolysis assay (Pangburn, 1988, Methods in Enzymology; and Katschke, 2009, Journal of Biological Chemistry).

In some examples, the aptamers described herein increase the activity of fD as measured by a fD esterase activity assay as compared to a control, and inhibit activity of fD as measured by a hemolysis assay. In other examples, the aptamers described herein inhibit activity of fD as compared to a control, and inhibit activity of fD as measured by a hemolysis assay. In yet other cases, the aptamer does not inhibit activity of complement Factor D as measured by a Factor D esterase activity assay as compared to a control, and does inhibit activity of complement Factor D as measured by a hemolysis assay.

Aptamers generally have high stability at ambient temperatures for extended periods of time. The aptamers described herein demonstrate greater than 70%, greater than 75%, greater than 80%, greater than 85%, greater 90%, greater than 91%, greater than 92%, greater than 93%, greater than 94%, greater than 95%, greater than 96%, greater than 97%, greater than 98%, greater than 99%, greater than 99.5%, or greater than 99.9% activity in solution under physiological conditions at 30 days or later.

Indications

In some aspects, the methods and compositions provided herein are used for the treatment of ocular diseases or disorders. Ocular diseases or disorders can include, without limitation, any complement-mediated ocular disorders such as inflammatory conjunctivitis, including allergic and giant papillary conjunctivitis, macular edema, uveitis, endophthalmitis, scleritis, corneal ulcers, dry eye syndrome, glaucoma, ischemic retinal disease, corneal transplant rejection, complications related to intraocular surgery such intraocular lens implantation and inflammation associated with cataract surgery, Behcets disease, Stargardt disease, immune complex vasculitis, Fuch's disease, Vogt-Koyanagi-Harada disease, subretinal fibrosis, keratitis, vitreo-retinal inflammation, ocular parasitic infestation/migration, retinitis pigmentosa, cytomeglavirus retinitis and choroidal inflammation.

Other examples of ocular diseases or disorders that may be amendable to treatment by the methods and compositions provided herein may include, without limitation, ectropion, lagophthalmos, blepharochalasis, ptosis, xanthelasma of the eyelid, parasitic infestation of the eyelid, dermatitis of the eyelid, dacryoadenitis, epiphora, dysthyroid exophthalmos, conjunctivitis, scleritis, keratitis, corneal ulcer, corneal abrasion, snow blindness, arc eye, Thygeson's superficial punctate keratopathy, corneal neovascularization, Fuchs' dystrophy, keratoconus, keratoconjunctivitis sicca, iritis, uveitis, sympathetic ophthalmia, cataracts, chorioretinal inflammation, focal chorioretinal inflammation, focal chorioretinitis, focal choroiditis, focal retinitis, focal retinochoroiditis, disseminated chorioretinal inflammation, disseminated chorioretinitis, disseminated choroiditis, disseminated retinitis, disseminated retinochoroiditis, exudative retinopathy, posterior cyclitis, pars planitis, Harada's disease, chorioretinal scars, macula scars of posterior pole, solar retinopathy, choroidal degeneration, choroidal atrophy, choroidal sclerosis, angioid streaks, hereditary choroidal dystrophy, choroideremia, choroidal dystrophy (central arealor), gyrate atrophy (choroid), ornithinaemia, choroidal haemorrhage and rupture, choroidal haemorrhage (not otherwise specified), choroidal haemorrhage (expulsive), choroidal detachment, retinoschisis, retinal artery occlusion, retinal vein occlusion, hypertensive retinopathy, diabetic retinopathy, retinopathy, retinopathy of prematurity, macular degeneration, Bull's Eye maculopathy, epiretinal membrane, peripheral retinal degeneration, hereditary retinal dystrophy, retinitis pigmentosa, retinal haemorrhage, separation of retinal layers, central serous retinopathy, retinal detachment, macular edema, glaucoma-optic neuropathy, glaucoma suspect-ocular hypertension, primary open-angle glaucoma, primary angle-closure glaucoma, floaters, Leber's hereditary optic neuropathy, optic disc drusen, strabismus, ophthalmoparesis, progressive external ophthaloplegia, esotropia, exotropia, disorders of refraction and accommodation, hypermetropia, myopia, astigmastism, anisometropia, presbyopia, internal ophthalmoplegia, amblyopia, Leber's congenital amaurosis, scotoma, anopsia, color blindness, achromatopsia, maskun, nyctalopia, blindness, River blindness, micropthalmia, coloboma, red eye, Argyll Robertson pupil, keratomycosis, xerophthalmia, aniridia, sickle cell retinopathy, ocular neovascularization, retinal neovascularization, subretinal neovascularization; rubeosis iritis inflammatory diseases, chronic posterior and pan uveitis, neoplasms, retinoblastoma, pseudoglioma, neovascular glaucoma; neovascularization resulting following a combined vitrectomy-2 and lensectomy, vascular diseases, retinal ischemia, choroidal vascular insufficiency, choroidal thrombosis, neovascularization of the optic nerve, diabetic macular edema, cystoid macular edema, proliferative vitreoretinopathy, and neovascularization due to penetration of the eye or ocular injury.

In some aspects, the methods and compositions provided herein are suitable for the treatment of macular degeneration. In some cases, macular degeneration is age-related macular degeneration. In some cases, the methods and compositions can be utilized to treat neovascular or exudative ("wet") age-related macular degeneration. In other cases, the methods and compositions can be utilized to treat non-exudative ("dry") age-related macular degeneration. In some cases, advanced forms of dry age-related macular degeneration can be treated, including geographic atrophy. In some cases, the methods and compositions herein can be utilized to prevent age-related macular degeneration and associated diseases thereof. In other cases, the methods and compositions herein can be utilized to slow or halt the progression of age-related macular degeneration and associated diseases thereof.

In some aspects, the methods and compositions provided herein are suitable for the treatment of Stargardt disease. In some cases, the methods and compositions herein can be utilized to prevent age-related Stargardt disease. In other cases, the methods and compositions herein can be utilized to slow or halt the progression of Stargardt disease.

In some aspects, the methods and compositions provided herein are suitable for the treatment of diseases causing ocular symptoms. Examples of symptoms which may be amenable to treatment with the methods disclosed herein include: increased drusen volume, reduced reading speed, reduced color vision, retinal thickening, increase in central retinal volume and/or, macular sensitivity, loss of retinal cells, increase in area of retinal atrophy, reduced best corrected visual acuity such as measured by Snellen or ETDRS scales, Best Corrected Visual Acuity under low luminance conditions, impaired night vision, impaired light sensitivity, impaired dark adaptation, contrast sensitivity, and patient reported outcomes.

In some cases, the methods and compositions provided herein may alleviate or reduce a symptom of a disease. In some cases, treatment with an aptamer provided herein may result in a reduction in the severity of any of the symptoms described herein. In some cases, treatment with an aptamer described herein may slow, halt or reverse the progression of any of the symptoms described herein. In some cases, treatment with an aptamer described herein may prevent the development of any of the symptoms described herein. In some cases, treatment with an aptamer described herein may slow, halt or reverse the progression of a disease, as measured by the number and severity of symptoms experienced. Examples of symptoms and relevant endpoints where the aptamer may have a therapeutic effect include increased drusen volume, reduced reading speed, reduced color vision, retinal thickening, increase in central retinal volume and/or, macular sensitivity, loss of retinal cells, increase in area of retinal atrophy, reduced best corrected visual acuity such as measured by Snellen or ETDRS scales, Best Corrected Visual Acuity under low luminance conditions, impaired night vision, impaired light sensitivity, impaired dark adaptation, contrast sensitivity, and patient reported outcomes. In some instances, treatment with an aptamer described herein may have beneficial effects as measured by clinical endpoints including drusen volume, reading speed, retinal thickness as measured by Optical Coherence Tomography or other techniques, central retinal volume, number and density of retinal cells, area of retinal atrophy as measured by Fundus Photography or Fundus Autofluoresence or other techniques, best corrected visual acuity such as measured by Snellen or ETDRS scales, Best Corrected Visual Acuity under low luminance conditions, light sensitivity, dark adaptation, contrast sensitivity, and patient reported outcomes as measured by such tools as the National Eye Institute Visual Function Questionnaire and Health Related Quality of Life Questionnaires.

Subjects

In some aspects, the methods and compositions provided herein are utilized to treat a subject in need thereof. In some cases, the subject suffers from an ocular disease or disorder. The subject can be a non-human animal, for example, a non-human primate, a livestock animal, a domestic pet, or a laboratory animal. For example, a non-human animal can be an ape (e.g., a chimpanzee, a baboon, a gorilla, or an orangutan), an old world monkey (e.g., a rhesus monkey), a new world monkey, a dog, a cat, a bison, a camel, a cow, a deer, a pig, a donkey, a horse, a mule, a lama, a sheep, a goat, a buffalo, a reindeer, a yak, a mouse, a rat, a rabbit, or any other non-human animal. In some cases, the subject is a human. In some cases, the human is a patient at a hospital or a clinic.

In cases where the subject is a human, the subject may be of any age. In some cases, the subject has an age-related ocular disease or disorder (e.g., age-related macular degeneration, Stargardt disease). In some cases, the subject is about 50 years or older. In some cases, the subject is about 55 years or older. In some cases, the subject is about 60 years or older. In some cases, the subject is about 65 years or older. In some cases, the subject is about 70 years or older. In some cases, the subject is about 75 years or older. In some cases, the subject is about 80 years or older. In some cases, the subject is about 85 years or older. In some cases, the subject is about 90 years or older. In some cases, the subject is about 95 years or older. In some cases, the subject is about 100 years or older. In some cases, the subject is about 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or greater than 100 years old. In some cases, the subject is about 1, 2, 3, 4, 5, 6, 7, 8, 9, 10, 11, 12, 13, 14, 15, 16, 17, 18, 19, 20 or greater than 20 years old.

In cases where the subject is a human, the subject may have any genetic profile. In some cases, the subject may have mutations in complement Factor H (CFH), complement component 3(C3), complement component 2 (C2), complement Factor B, complement Factor I (CFI), ABC4A, ELOVL4, or any combination thereof.

In some aspects, the methods and compositions provided herein are utilized to treat a subject suffering from ocular symptoms as described herein. In some aspects, the methods and compositions provided herein are utilized to treat a subject suffering from an ocular disease as provided herein. In some cases, the methods and compositions provided herein are utilized to treat a subject suffering from wet AMD. In some cases, the methods and compositions provided herein are utilized to treat a subject suffering from dry AMD or geographic atrophy. In some cases, the methods and compositions provided herein are utilized to treat a subject suffering from Stargardt disease.

In some aspects, the methods and compositions provided herein may be utilized to treat a subject with a highly active immune system. In some cases, the methods and compositions provided herein may be used to treat a subject with an autoimmune disease. In some cases, the methods and compositions provided herein may be used to treat a subject with an inflammatory disease. In some cases, the methods and compositions provided herein may be used to treat a subject undergoing an inflammatory reaction to a disease such as an infectious disease. For example, the aptamers described herein may be used to treat a subject with a fever. In some cases, the aptamers described herein may be used to treat a subject with an allergy. In some cases, the aptamers described herein may be used to treat a subject suffering from an allergic response. In some cases, the aptamers described herein may be particularly useful for treating a subject who has experienced an allergic reaction to an antibody treatment, and/or who has developed neutralizing antibodies against an antibody treatment.

Pharmaceutical Compositions

Disclosed herein are pharmaceutical compositions for the treatment of ocular diseases. In some cases, the pharmaceutical compositions can be used to treat AMD. In some cases, the pharmaceutical compositions can be used to treat non-exudative (dry) AMD. In some cases, the pharmaceutical compositions can be used to treat geographic atrophy (advanced dry AMD). In some cases, the pharmaceutical compositions can be used to treat wet AMD. In some cases, the pharmaceutical compositions can be used to treat Stargardt disease. Pharmaceutical compositions described herein may include one or more aptamers for the treatment of dry AMD. Pharmaceutical compositions described herein may include one or more aptamers for the treatment of wet AMD. Pharmaceutical compositions described herein may include one or more aptamers for the treatment of Stargardt disease. In some cases, the one or more aptamers bind to and inhibit a component of the alternative complement pathway. In some cases, the one or more aptamers bind to one or more targets of fD as described herein. In some cases, the one or more aptamers inhibit fD as described herein. In some cases, the compositions include, e.g., an effective amount of the aptamer, alone or in combination, with one or more vehicles (e.g., pharmaceutically acceptable compositions or e.g., pharmaceutically acceptable carriers). In some cases, the compositions described herein are administered with one or more additional pharmaceutical treatments (e.g., co-administered, sequentially administered or co-formulated). In some examples, the compositions described herein are co-administered with one or more of an anti-vascular endothelial growth factor (VEGF) therapy, an anti-Factor P therapy, an anti-complement component 5 (C5) therapy, an anti-complement component 3 (C3) therapy, an anti-platelet-derived growth factor (PDGF) therapy, an anti-hypoxia-inducible factor 1-alpha (HIF1α) therapy, an anti-FAS therapy, an anti-integrin therapy or an anti-angiopoietin-2 (Ang2) therapy.

Formulations

Compositions as described herein may comprise a liquid formulation, a solid formulation or a combination thereof. Non-limiting examples of formulations may include a tablet, a capsule, a gel, a paste, a liquid solution and a cream. The compositions of the present disclosure may further comprise any number of excipients. Excipients may include any and all solvents, coatings, flavorings, colorings, lubricants, disintegrants, preservatives, sweeteners, binders, diluents, and vehicles (or carriers). Generally, the excipient is compatible with the therapeutic compositions of the present disclosure. The pharmaceutical composition may also contain minor amounts of non-toxic auxiliary substances such as wetting or emulsifying agents, pH buffering agents, and other substances such as, for example, sodium acetate, and triethanolamine oleate.

Dosage and Routes of Administration

Therapeutic doses of formulations of the disclosure can be administered to a subject in need thereof. In some cases, a formulation is administered to the eye of a subject to treat, for example, dry AMD, geographic atrophy, wet AMD or Stargardt disease. Administration to the eye can be a) topical; b) local ocular delivery; or c) systemic. A topical formulation can be applied directly to the eye (e.g., eye drops, contact lens loaded with the formulation) or to the eyelid (e.g., cream, lotion, gel). In some cases, topical administration can be to a site remote from the eye, for example, to the skin of an extremity. This form of administration may be suitable for targets that are not produced directly by the eye. In one non-limiting example, fD is thought to be produced primarily by adipose cells, and thus an anti-fD aptamer may be administered topically to a non-ocular region of the body. In some cases, a formulation of the disclosure is administered by local ocular delivery. Non-limiting examples of local ocular delivery include intravitreal (IVT), intracamarel, subconjunctival, subtenon, retrobulbar, posterior juxtascleral, and peribulbar. In some cases, a formulation of the disclosure is delivered by intravitreal administration (IVT). Local ocular delivery may generally involve injection of a liquid formulation. In other cases, a formulation of the disclosure is administered systemically. Systemic administration can involve oral administration. In some cases, systemic administration can be intravenous administration, subcutaneous administration, infusion, implantation, and the like.

Other formulations suitable for delivery of the pharmaceutical compositions described herein may include a sustained release gel or polymer formulations by surgical implantation of a biodegradable microsize polymer system, e.g., microdevice, microparticle, or sponge, or other slow release transscleral devices, implanted during the treatment of an ophthalmic disease, or by an ocular delivery device, e.g. polymer contact lens sustained delivery device. In some cases, the formulation is a polymer gel, a self-assembling gel, a durable implant, an eluting implant, a biodegradable matrix or biodegradable polymers. In some cases, the formulation may be administered by iontophoresis using electric current to drive the composition from the surface to the posterior of the eye. In some cases, the formulation may be administered by a surgically implanted port with an intravitreal reservoir, an extra-vitreal reservoir or a combination thereof. Examples of implantable ocular devices can include, without limitation, the Durasert™ technology developed by Bausch & Lomb, the ODTx device developed by On Demand Therapeutics, the Port Delivery System developed by ForSight VISION4 and the Replenish Micro-Pump™ System developed by Replenish, Inc.

In some cases, nanotechnologies can be used to deliver the pharmaceutical compositions including nanospheres, nanoparticles, nanocapsules, liposomes, nanomicelles and dendrimers.

A composition of the disclosure can be administered once or more than once each day. In some cases, the composition is administered as a single dose (i.e., one-time use). In this example, the single dose may be curative. In other cases, the composition may be administered serially (e.g., taken every day without a break for the duration of the treatment regimen). In some cases, the treatment regime can be less than a week, a week, two weeks, three weeks, a month, or greater than a month. In some cases, the composition is administered over a period of at least 12 weeks. In other cases, the composition is administered for a day, at least two consecutive days, at least three consecutive days, at least four consecutive days, at least five consecutive days, at least six consecutive days, at least seven consecutive days, at least eight consecutive days, at least nine consecutive days, at least ten consecutive days, or at least greater than ten consecutive days. In some cases, a therapeutically effective amount can be administered one time per week, two times per week, three times per week, four times per week, five times per week, six times per week, seven times per week, eight times per week, nine times per week, 10 times per week, 11 times per week, 12 times per week, 13 times per week, 14 times per week, 15 times per week, 16 times per week, 17 times per week, 18 times per week, 19 times per week, 20 times per week, 25 times per week, 30 times per week, 35 times per week, 40 times per week, or greater than 40 times per week. In some cases, a therapeutically effective amount can be administered one time per day, two times per day, three times per day, four times per day, five times per day, six times per day, seven times per day, eight times per day, nine times per day, 10 times per day, or greater than 10 times per day. In some cases, the composition is administered at least twice a day. In further cases, the composition is administered at least every hour, at least every two hours, at least every three hours, at least every four hours, at least every five hours, at least every six hours, at least every seven hours, at least every eight hours, at least every nine hours, at least every 10 hours, at least every 11 hours, at least every 12 hours, at least every 13 hours, at least every 14 hours, at least every 15 hours, at least every 16 hours, at least every 17 hours, at least every 18 hours, at least every 19 hours, at least every 20 hours, at least every 21 hours, at least every 22 hours, at least every 23 hours, or at least every day.

Aptamers as described herein may be particularly advantageous over antibodies as they may sustain therapeutic intravitreal concentrations of drug for longer periods of time, thus requiring less frequent administration. For example, an anti-fD Fab having an amino acid sequence of heavy chain variable region according to SEQ ID NO: 71 and a light chain variable region according to SEQ ID NO: 72, may show clinical efficacy for the treatment of geographic atrophy at 10 mg when dosed every 4 weeks (q4w) but not every 8 weeks (q8w). The aptamers described herein have a longer intraocular half-life, and/or sustain therapeutic intravitreal concentrations of drug for longer periods of time, than an anti-fD Fab with an amino acid sequence of heavy chain variable region according to SEQ ID NO: 71 and light chain variable region according to SEQ ID NO: 72 and other antibody therapies and thus, can be dosed less frequently. In some cases, the aptamers are dosed at least every 4 weeks (q4w), every 5 weeks (q5w), every 6 weeks (q6w), every 7 weeks (q7w), every 8 weeks (q8w), every 9 weeks (q9w), every 10 weeks (q10w), every 12 weeks (q12w) or greater than q12w.

In some aspects, a therapeutically effective amount of the aptamer is administered. A "therapeutically effective amount" or "therapeutically effective dose" are used interchangeably herein and refer to an amount of a therapeutic agent (e.g., an aptamer) that provokes a therapeutic or desired response in a subject. The therapeutically effective amount of the composition may be dependent on the route of administration. In the case of systemic administration, a therapeutically effective amount may be about 10 mg/kg to about 100 mg/kg. In some cases, a therapeutically effective amount may be about 10 µg/kg to about 1000 µg/kg for systemic administration. For intravitreal administration, a therapeutically effective amount can be about 0.01 mg to about 150 mg in about 25 µl to about 100 µl volume per eye.

Methods

Disclosed herein are methods for the treatment of ocular diseases. In some cases, the ocular disease is dry age-related macular degeneration or geographic atrophy. In some cases, the method involves administering a therapeutically effective amount of a composition to a subject to treat the disease. In some cases, the composition includes one or more aptamers as described herein. The aptamers may inhibit a function associated with fD as described herein. The methods can be performed at a hospital or a clinic, for example, the pharmaceutical compositions can be administered by a healthcare professional. In other cases, the pharmaceutical compositions can be self-administered by the subject. Treatment may commence with the diagnosis of a subject with an ocular disease (e.g., AMD). In the event that further treatments are necessary, follow-up appointments may be scheduled for the administration of subsequence doses of the composition, for example, administration every 8 weeks.

Methods of GeneratinE Antamers

The SELEX™ Method

The aptamers described herein can be generated by any method suitable for generating aptamers. In some cases, the aptamers described herein are generated by a process known as Systematic Evolution of Ligands by Exponential Enrichment" ("SELEX™"). The SELEX™ process is described in, e.g., U.S. patent application Ser. No. 07/536,428, filed Jun. 11, 1990, now abandoned, U.S. Pat. No. 5,475,096 entitled "Nucleic Acid Ligands", and U.S. Pat. No. 5,270,163 (see also WO 91/19813) entitled "Nucleic Acid Ligands", each of which are herein incorporated by reference. By performing iterative cycles of selection and amplification, SELEX™ may be used to obtain aptamers with any desired level of target binding affinity.

The SELEX™ method relies as a starting point upon a large library or pool of single stranded oligonucleotides comprising randomized sequences. The oligonucleotides can be modified or unmodified DNA, RNA, or DNA/RNA hybrids. In some examples, the pool comprises 100% random or partially random oligonucleotides. In other examples, the pool comprises random or partially random oligonucleotides containing at least one fixed sequence and/or conserved sequence incorporated within randomized sequence. In other examples, the pool comprises random or partially random oligonucleotides containing at least one fixed sequence and/or conserved sequence at its 5' and/or 3' end which may comprise a sequence shared by all the molecules of the oligonucleotide pool. Fixed sequences are sequences common to oligonucleotides in the pool which are incorporated for a preselected purpose such as, CpG motifs, hybridization sites for PCR primers, promoter sequences for RNA polymerases (e.g., T3, T4, T7, and SP6), sequences to form stems to present the randomized region of the library within a defined terminal stem structure, restriction sites, or homopolymeric sequences, such as poly A or poly T tracts, catalytic cores, sites for selective binding to affinity columns, and other sequences to facilitate cloning and/or sequencing of an oligonucleotide of interest. Conserved sequences are sequences, other than the previously described fixed sequences, shared by a number of aptamers that bind to the same target.

The oligonucleotides of the pool can include a randomized sequence portion as well as fixed sequences necessary for efficient amplification. Typically the oligonucleotides of the starting pool contain fixed 5' and 3' terminal sequences which flank an internal region of 30-50 random nucleotides. The randomized nucleotides can be produced in a number of ways including chemical synthesis and size selection from randomly cleaved cellular nucleic acids. Sequence variation in test nucleic acids can also be introduced or increased by mutagenesis before or during the selection/amplification iterations.

The random sequence portion of the oligonucleotide can be of any length and can comprise ribonucleotides and/or deoxyribonucleotides and can include modified or non-natural nucleotides or nucleotide analogs. Typical syntheses carried out on automated DNA synthesis equipment yield $10^{14}$-$10^{16}$ individual molecules, a number sufficient for most SELEX™ experiments. Sufficiently large regions of random sequence in the sequence design increases the likelihood that each synthesized molecule is likely to represent a unique sequence.

The starting library of oligonucleotides may be generated by automated chemical synthesis on a DNA synthesizer. To synthesize randomized sequences, mixtures of all four nucleotides are added at each nucleotide addition step during the synthesis process, allowing for random incorporation of nucleotides. As stated above, in some cases, random oligonucleotides comprise entirely random sequences; however, in other cases, random oligonucleotides can comprise stretches of nonrandom or partially random sequences. Partially random sequences can be created by adding the four nucleotides in different molar ratios at each addition step.

The starting library of oligonucleotides may be RNA, DNA, substituted RNA or DNA or combinations thereof. In those instances where an RNA library is to be used as the starting library it is typically generated by synthesizing a DNA library, optionally PCR amplifying, then transcribing the DNA library in vitro using T7 RNA polymerase or modified T7 RNA polymerases (e.g., T7 RNA polymerase bearing the mutations Y639L and H784A), and purifying the transcribed library. The nucleic acid library is then mixed with the target under conditions favorable for binding and subjected to step-wise iterations of binding, partitioning and amplification, using the same general selection scheme, to achieve virtually any desired criterion of binding affinity and selectivity. More specifically, starting with a mixture containing the starting pool of nucleic acids, the SELEX™ method includes steps of: (a) contacting the mixture with the target under conditions favorable for binding; (b) partitioning unbound nucleic acids from those nucleic acids which have bound specifically to target molecules; (c) dissociating the nucleic acid-target complexes; (d) amplifying the nucleic acids dissociated from the nucleic acid-target complexes to yield a ligand-enriched mixture of nucleic acids; and (e) reiterating the steps of binding, partitioning, dissociating and amplifying through as many cycles as desired to yield highly specific, high affinity nucleic acid ligands to the target molecule. In those instances where RNA aptamers are being selected, the SELEX™ method further comprises the steps of: (i) reverse transcribing the nucleic acids dissociated from the nucleic acid-target complexes before amplification in step (d); and (ii) transcribing the amplified nucleic acids from step (d) before restarting the process.

Within a nucleic acid mixture containing a large number of possible sequences and structures, there is a wide range of binding affinities for a given target. Those which have the higher affinity (lower dissociation constants) for the target are most likely to bind to the target. After partitioning, dissociation and amplification, a second nucleic acid mixture is generated, enriched for the higher binding affinity candidates. Additional rounds of selection progressively favor the best ligands until the resulting nucleic acid mixture is predominantly composed of only one or a few sequences. These can then be cloned, sequenced and individually tested as ligands or aptamers for 1) target binding affinity; and 2) ability to effect target function.

Cycles of selection and amplification are repeated until a desired goal is achieved. In the most general case, selection/amplification is continued until no significant improvement in binding strength is achieved on repetition of the cycle. The method is typically used to sample approximately $10^{14}$ different nucleic acid species but may be used to sample as many as about $10^{18}$ different nucleic acid species. Generally, nucleic acid aptamer molecules are selected in a 5 to 20 cycle procedure.

In some cases, the aptamers of the disclosure are generated using the SELEX™ method as described above. In other cases, the aptamers of the disclosure are generated using any modification or variant of the SELEX™ method.

In some cases, the aptamers described herein have been generated using methodologies to select for specific sites related to activity or function of a target protein. In some cases, the aptamers described herein may be selected using methods that improve the chances of selecting an aptamer with a desired function or desired binding site. In some cases, the aptamers described herein are generated using methods that increase the chances of selecting an aptamer that binds to a region of fD that serves as an epitope for an anti-fD therapeutic antibody, which anti-fD therapeutic antibody inhibits a function associated with fD.

EXAMPLES

The following examples are given for the purpose of illustrating various embodiments of the invention and are not meant to limit the present invention in any fashion. The present examples, along with the methods described herein are presently representative of preferred embodiments, are exemplary, and are not intended as limitations on the scope of the invention. Changes therein and other uses which are encompassed within the spirit of the invention as defined by the scope of the claims will occur to those skilled in the art.

Example 1. Identification of Modified RNA Aptamers to fD

A. Selection of Anti-Factor D Aptamers

Figures 3A, 3B:
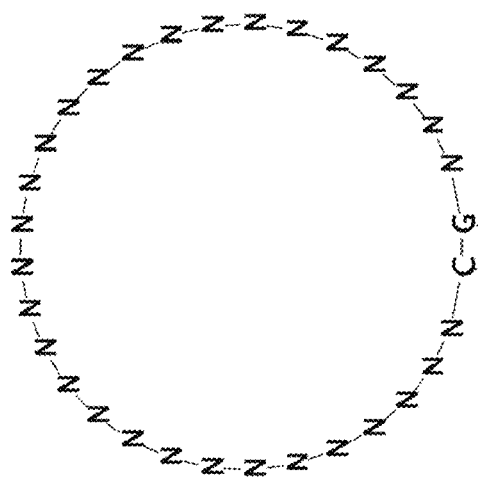
FIG. 3A, FIG. 3B, and FIG. 3C depict a non-limiting example of an aptamer library sequence that may be utilized to generate anti-Factor D aptamers according to an embodiment of the disclosure.
Figure 3C:
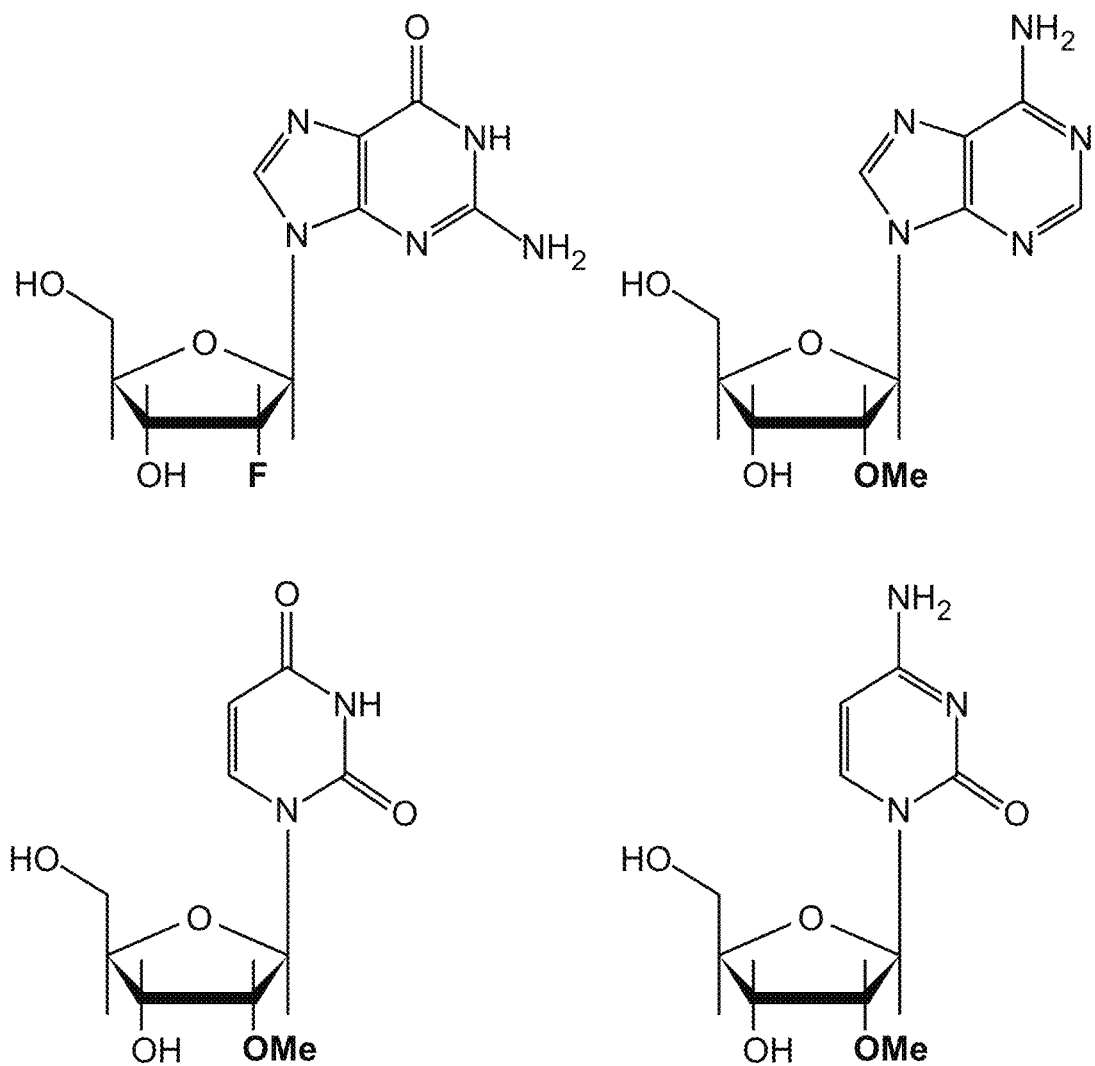

Anti-factor D (fD) aptamers were identified using an N30 library (N30S) comprised of a 30-nucleotide random region flanked by constant regions containing a built-in stem region as depicted in FIG. 3A. The sequence in italics represents the forward and reverse primer binding sites. The built-in stem region is shown in bold. FIG. 3B depicts a representation of the N30S library with the reverse oligo hybridized. For nuclease stability, the library was composed of 2'F G and 2'-O-methyl A/C/U. FIG. 3C depicts structures of modified nucleotides used to generate the N30S library for selection against target fD. For simplicity, the nucleosides, and not the nucleotide triphosphates are shown.

The library sequence (underlined sequences represent the built-in stem) and the sequence of oligos used to amplify the library are described in Table 2.

TABLE 2

Library sequence and sequence of oligos used to amplify the library

| SEQ ID NO. | | Sequence (5' to 3') |
|---|---|---|
| SEQ ID NO: 93 | Library sequence (Total library length: 89 bases) | GGGAGTGTGTACGAGGCATT<u>AGGCCGCC</u>-N30-<u>GGCGGCTT</u>TGATACTTGATCGCCCT AGAAGC |
| SEQ ID NO: 64 | N30S.F | TCTTAATACGACTCACTATAGGGAGTGTG TACGAGGCATTA |
| SEQ ID NO: 65 | N30S.R | GCTTCTAGGGCGATCAAGTATCA |

The starting library was transcribed from a pool of ~$10^{14}$ double-stranded DNA (dsDNA) molecules. The dsDNA library was generated by primer extension using Klenow exo (−) DNA polymerase, the pool forward primer (N30S.F) and synthetic single-stranded DNA (ssDNA) molecule encoding the library. The dsDNA was subsequently converted to 100% backbone modified RNA via transcription using a mixture of 2'F GTP, 2'-O-methyl ATP/CTP/UTP and a variant of T7 RNA polymerase bearing the mutations Y639L and H784A in buffer optimized to facilitate efficient transcription. Following transcription, RNAs were treated with DNAse to remove the template dsDNA and purified.

The selection targeting fD was facilitated by the use of a His-tagged recombinant human complement Factor D protein and magnetic His capture beads. Briefly, beads (the amount varied with the amount of target protein coupled) were washed three times with immobilization buffer (50 mM sodium phosphate, pH 8.0, 300 mM NaCl, 0.01% Tween-20) and were resuspended in 50 µL of immobilization buffer. His-tagged recombinant fD, in immobilization buffer, was then added to the beads and incubated at room temperature for 30 mins. The amount of target protein varied with the rounds (Table 3). The beads were washed three times with binding buffer SB1T (40 mM HEPES, pH 7.5, 125 mM NaCl, 5 mM KCl, 1 mM $MgCl_2$, 1 mM $CaCl_2$), 0.05% Tween-20) to remove any unbound protein and then re-suspended in 50 µL SB1T buffer containing 1 µg/µl ssDNA and 0.1% BSA.

For the first round of selection, ~3 nanomoles of the Round 0 RNA pool, ~$10^{14}$ sequences, was used. Prior to each round, the library was thermally equilibrated by heating at 80° C. for 5 mins and cooled at room temperature for 15 mins in the presence of a 1.5-fold molar excess of reverse primer (N30S.R) to allow the library to refold and simultaneously block the 3' end of the pool. Following renaturation, the final volume of the reaction was adjusted to 50 µL in SB1T supplemented with 1 µg/ml ssDNA and 0.1% BSA.

For the first round, the library was added to the fD immobilized on beads and incubated at 37° C. for 1 hour with intermittent mixing. After one hour, the beads were washed using 3×1 ml SB1T buffer to remove unbound aptamers. For round 0, each wash step was incubated for 5 minutes. After washing, fD-bound aptamers were eluted using 200 µL elution buffer (2M Guanidine-HCl in SB1T buffer) two times (total volume 400 µL). The eluted aptamers, in 400 µL of elution buffer, were precipitated by adding 40 µL 3M NaOAc, pH 5.2, 1 ml ethanol and 2 µl glycogen and incubating at −80° C. for 15 mins. The recovered library was converted to DNA by reverse transcription using Super Script IV reverse transcriptase, and the ssDNA was subsequently amplified by PCR. The resulting dsDNA library was subsequently converted back into modified RNA via transcription as described above. DNased, purified RNA was used for subsequent rounds.

For subsequent rounds, the washing time and number of washes was varied as the selection progressed, the input RNA was kept fixed at 25 picomole, and the protein input varied (Table 3). After the first round, a negative selection step was included in all the subsequent rounds. For the negative selection, the pool was prepared as described before and first incubated with non-labelled beads for 1 hour at 37° C. in SB1T buffer. The beads were then spun down and the supernatant containing molecules that did not bind to the unlabeled beads was incubated with fD-labeled beads for an additional 1 hour at 37° C.

B. Assessing the Progress of Selection

Figure 4:
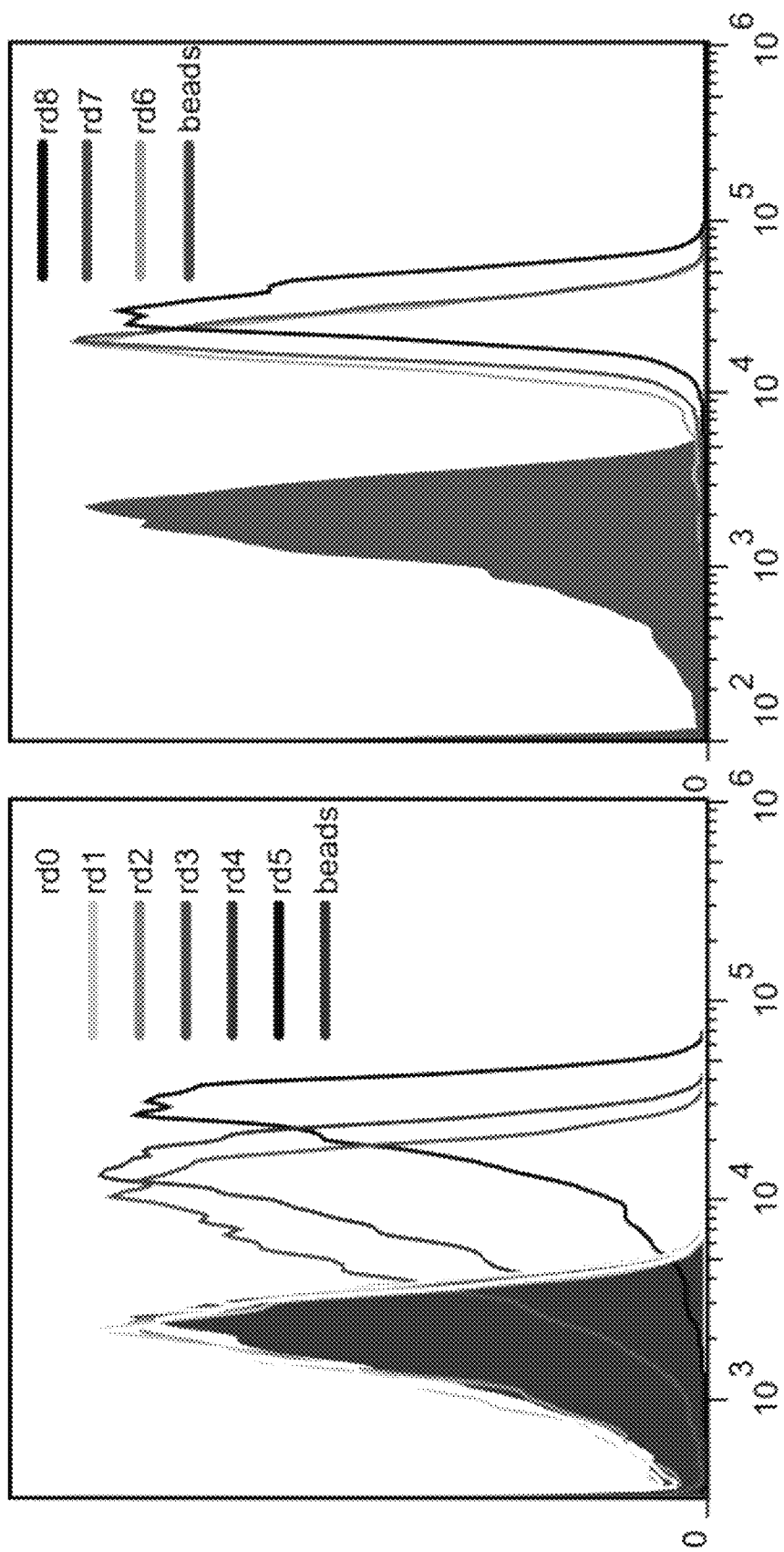
FIG. 4 depicts a non-limiting example of a method for selecting anti-Factor D aptamers according to an embodiment of the disclosure.
Figure 6B:
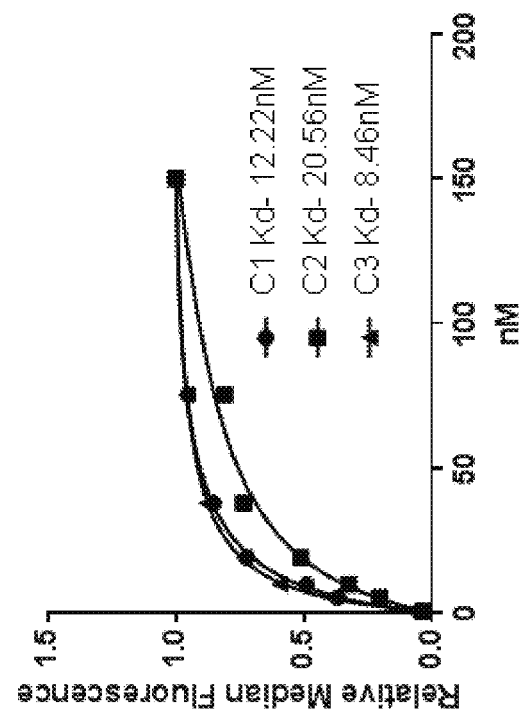
FIG. 6A and FIG. 6B depict measurement of $K_d$ values of anti-Factor D aptamers according to an embodiment of the disclosure.
Figure 6A:
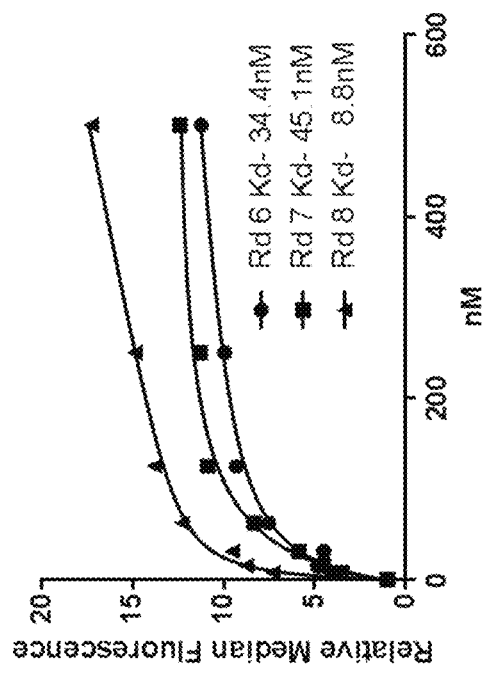

Flow cytometry was used to assess the progress of the selection. For these assays, RNA from each round was first hybridized with reverse complement oligonucleotide composed of 2'OMe RNA labeled with Dylight® 650 (Dy650-N30S.R.OMe). Briefly, the library was combined with 1.5-fold molar excess of Dy650-N30S.R.OMe, heated at 80° C. for 6 mins and allowed to cool at room temperature for 15 min. after which it was incubated with beads labelled with fD, in SB1T buffer containing 0.1% BSA and 1 µg/µl ssDNA. Following incubation for 1 hour at 37° C., the beads were washed 3 times with SB1T, re-suspended in SB1T buffer and analyzed by flow cytometry. As shown in FIG. 4, an improvement in fluorescent signal with the progressing rounds was seen as early as Round 3. After Round 6, there was little change in the binding signal through Round 8. "Beads" refers to the signal of fD-labelled beads in the absence of labeled RNA. The apparent affinity of rounds 6, 7, and 8 for fD was also measured using flow cytometry-based assays and revealed $K_d$s in the range of 8-45 nM (FIG. 6A, Table 5).

C. Selection, Purification and Characterization of Clones

The enriched aptamer populations recovered from rounds 6, 7 and 8 of the selection were sequenced to identify individual functional clones. The sequences were grouped in families based on sequence similarity. From an analysis of Rounds 6, 7 and 8, 7 individual clones were selected for testing. Individual bacterial colonies corresponding to these clones were picked up and plasmid isolated using QIAGEN Mini Prep Kit. The sequences for each clone was PCR amplified using the F and R oligo of the library. Each full length clone was transcribed from the PCR product using the protocol described before. The clones were gel purified and used for further analysis.

A summary of the clones tested is shown in Table 4. For simplicity, the constant regions have been omitted from sequences C1 though C3.

D. Assaying Individual Clones for Binding

Individual clones were assayed by flow cytometry in a manner similar to that described above for individual rounds of selection. In the case of clones C1 through C3, fluorescent labeling of each aptamer was achieved via hybridization to Dy650-N30S.R.OMe as described above.

Figure 5:
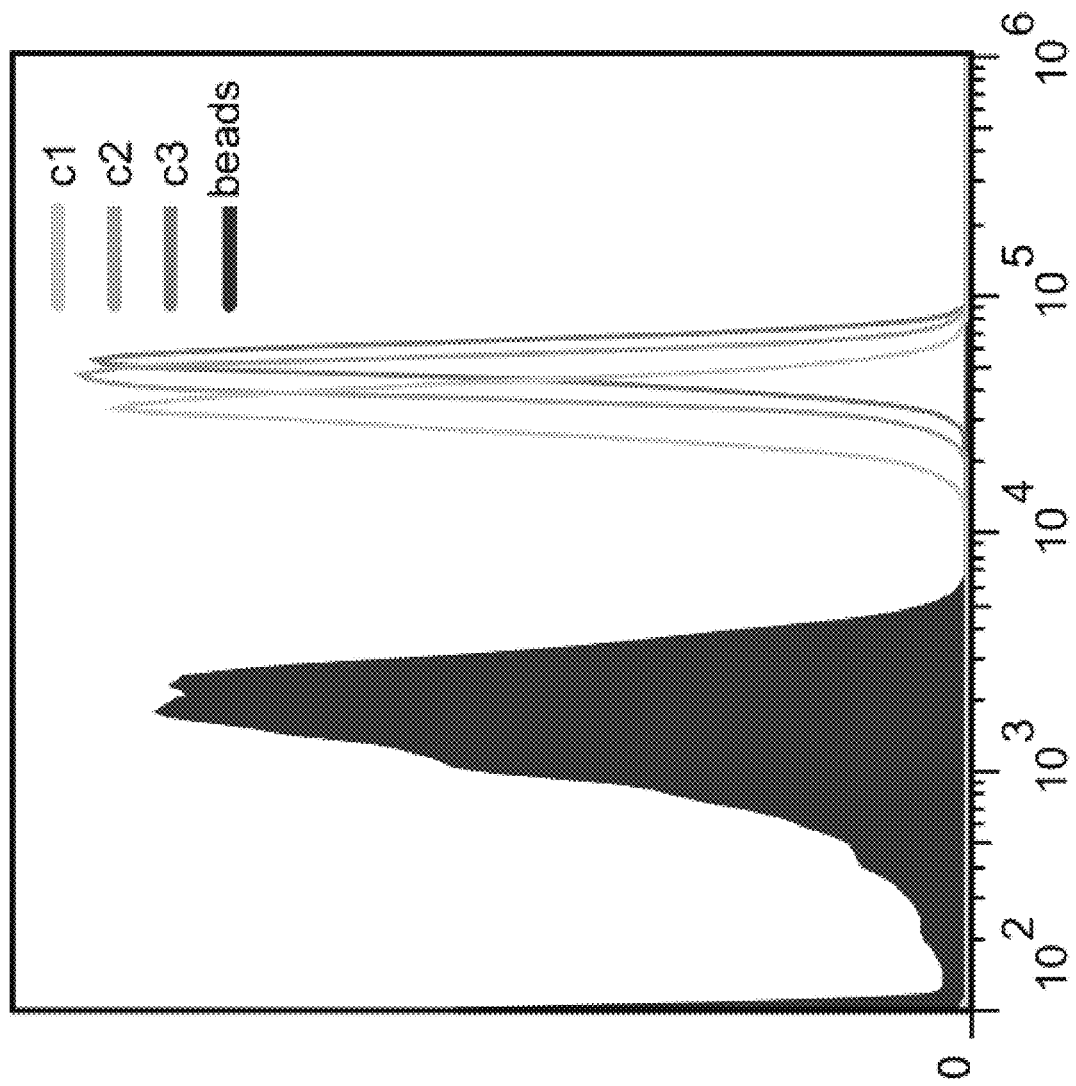
FIG. 5 depicts binding analysis of anti-Factor D aptamers by flow cytometry according to an embodiment of the disclosure.

As an initial assay, the binding of each aptamer to fD was assessed using bead-immobilized fD when incubated at 100 nM for 1 hour at 37° C. As shown in FIG. 5, all aptamers displayed significant levels of binding to fD beads. No binding was observed when similar experiments were performed using beads bearing no target or a non-specific target, human growth factor.

E. Measurement of Apparent $K_d$ on Beads

Flow cytometry was used to measure the binding affinity of each individual aptamer to fD. Assays were again performed as described before but using serially diluted solutions of each aptamer. Following incubation for 1 hour at 37° C., the beads were washed and fluorescence was measured using flow cytometry and a plot of median fluorescent intensity versus aptamer concentration (FIG. 6B) was used to determine the apparent binding constant for each clone. Apparent $K_d$ values were obtained using the equation Y=Bmax® X/(KD+X). The apparent binding constant for each clone is also reported in Table 5. The apparent affinity of aptamers to fD ranged from approximately 3 to 20 nM.

F. Competition Assays with Rounds or Individual Clones

Figure 7:
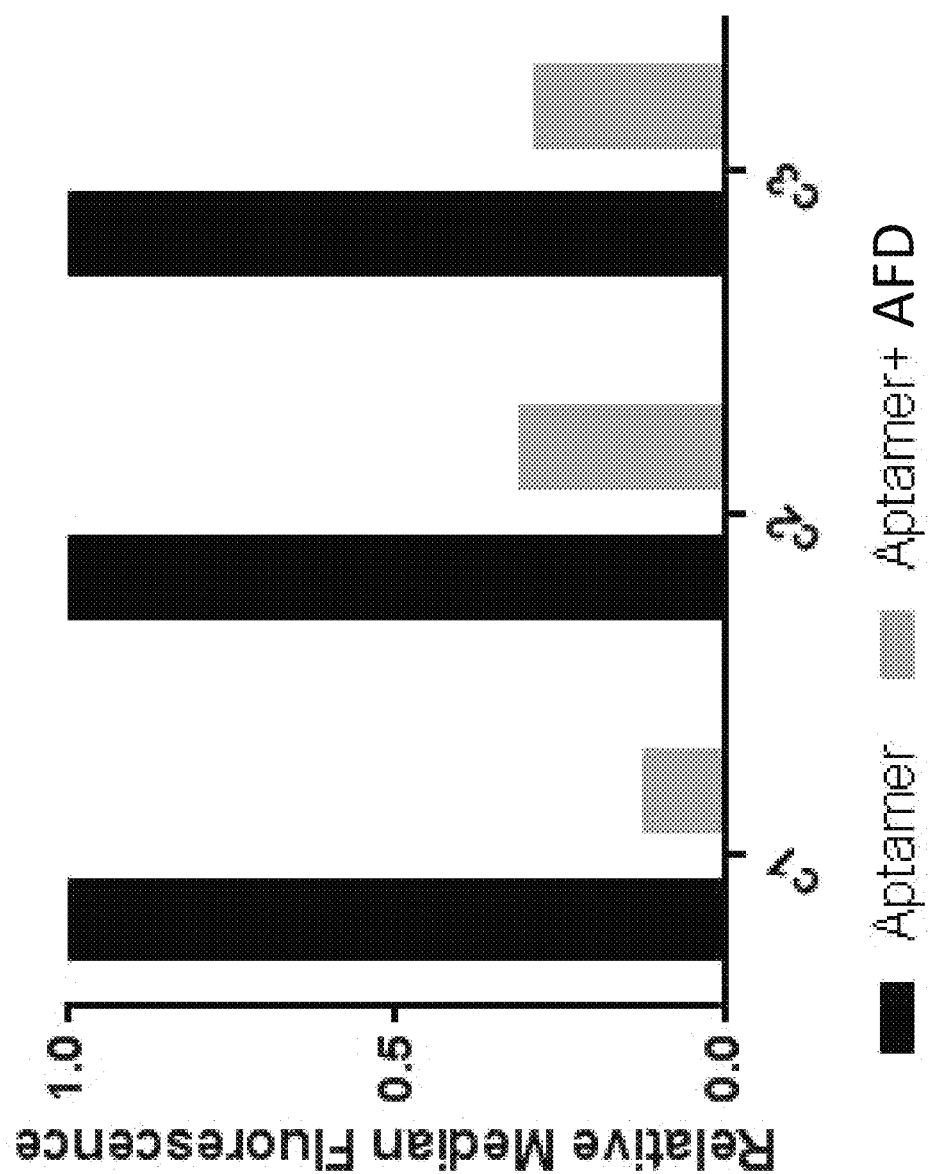
FIG. 7 depicts a competition assay according to an embodiment of the disclosure.

Competition binding assays were performed using a clone of an anti-fD Fab with an amino acid sequence of heavy chain variable region according to SEQ ID NO: 71 and light chain variable region according to SEQ ID NO: 72 (hereinafter, "AFD") to further assess binding. For the competition assays, beads labelled with fD were first incubated with 50 nM round or individual aptamer, in 50 μl SB1T (with ssDNA and BSA), for 30 mins at 37° C. The beads were then washed with SB1T to remove unbound aptamers and incubated with or without 100 nM AFD for 30 mins at 37° C. Following incubation, the beads were washed three times with SB1T, and assayed by flow cytometry (FIG. 7). These assays revealed that binding of AFD reduced the aptamer signal by ~75%-~90%, for both the Round 7 and 8 populations as well all selected aptamers. In cases where aptamers are sufficiently outcompeted by AFD as described above, such aptamers were presumed to be binding to the exosite or the self-inhibitory loop of fD.

TABLE 4

Sequences of random region-derived sequences of select ID aptamers

| SEQ ID NO. | Compound Name | Sequence (5' to 3') |
|---|---|---|
| SEQ ID NO: 1 with | C1 | GGGAGUGUGUACGAGGCAUUAGGCCGCCA CCCAAACUGCAGUCCUCGUAAGUCUGCCU |

TABLE 4-continued

Sequences of random region-derived sequences of select ID aptamers

| SEQ ID NO. | Compound Name | Sequence (5' to 3') |
|---|---|---|
| modifications | | GGCGGCUUUGAUACUUGAUCGCCCUAGAA GC where G is 2'F and A, C and U are 2'OMe modified RNA |
| SEQ ID NO: 2 with modifications | C2 | GGGAGUGUGUACGAGGCAUUAGUCCGCCG AAGUCUTJTJUGGCUCGGUTJTJTJUUCA AGGUCGGCGGCUUUGAUACUUGAUCGCCC UAGAAGC where G is 2'F and A, C and U are 2'OMe modified RNA |
| SEQ ID NO: 3 with modifications | C3 | GGGAGUGUGUACGAGGCAUUAGGCCGCCA CCUCGUUUGAUUGCGGUUGUUCGGCCGCG GGCGGCUUUGAUACUUGAUCGCCCUAGAA GC where G is 2'F and A, C and U are 2'OMe modified RNA |

TABLE 5

Affinity constant of selected rounds and aptamers generated in selection to fD

| Round/Clone | $K_d$ (nM) |
|---|---|
| Rd 6 | 34.4 |
| Rd 7 | 45.1 |
| Rd 8 | 8.8 |
| C1 | 12.2 |
| C2 | 20.6 |
| C3 | 8.5 |

TABLE 3

Selection details

| Round | Input library pmoles/conc | Target protein pmoles/conc | Binding buffer | Washing buffer | washes | #cycles | NGS |
|---|---|---|---|---|---|---|---|
| 0 | 1000 pm/40 μM | 40 pm/0.4 μM | SB1T | SB1T | 3 × 5 min | 22 | yes |
| 1 | 25 pm/1 μM | 40 pm/0.4 μM | SB1T | SB1T | 3 × 5 min | 22 | yes |
| 2 | 25 pm/1 μM | 40 pm/0.4 μM | SB1T | SB1T | 3 × 5 min | 20 | yes |
| 3 | 25 pm/1 μM | 4 pm/0.04 μM | SB1T | SB1T | 3 × 5 min | 18 | yes |
| 4 | 25 pm/1 μM | 8 pm/0.08 μM | SB1T | SB1T | 3 × 10 min | 18 | yes |
| 5 | 25 pm/1 μM | 8 pm/0.08 μM | SB1T | SB1T | 3 × 10 min | 16 | yes |
| 6 | 25 pm/1 μM | 4 pm/0.04 μM | HBSS | SB1T | 4 × 15 min | 14 | yes |
| 7 | 25 pm/1 μM | 4 pm/0.04 μM | HBSS | HBSS + SB1T | 4 × 15 min | 14 | yes |
| 8 | 25 pm/1 μM | 4 pm/0.04 μM | SB1T | SB1T | 4 × 15 min | 12 | yes |

Example 2. Selection of DNA Aptamers to Human Complement Factor D

Aptamers against human complement factor D (fD) were isolated by selection using an aptamer library composed of a 40-nucleotide random region flanked by defined fixed sequences (see Table 6). The library was comprised of unmodified DNA. The selection library was produced by solid phase DNA synthesis and gel purified prior to use.

TABLE 6

Oligonucleotides used to construct and replicate aptamer library

| SEQ ID NO. | Compound | Sequence (5' to 3') |
|---|---|---|
| SEQ ID NO: 67 | Selection library* | GTGACGACTGACATATCTGC-NNNNNNNNNNNNNNNNNNNNNNNNNNNNNNNNNNNNNNNNNNNN-CGTAGTTGAGTCTGAGTGCT |
| SEQ ID NO: 68 | Forward primer | GTGACGACTGACATATCTGC |
| SEQ ID NO: 69 | Reverse primer 1 | AGCACTCAGACTCAACTACG |
| SEQ ID NOS: 70 and 91 | Reverse primer 2** | AAAAAAAAAAAAAAAAAAAA-S9-AGCACTCAGACTCAACTACG |

*"N" indicates the nucleotide at this position is randomized and could be A, G, C or T in the starting library, with an ~25% chance of each base at each randomized position.
**"S9" represents a hexaethylene glycol spacer Prior to each round of selection, recombinant 6×His-tagged (SEQ ID NO: 92) human factor D was immobilized on Ni-NTA magnetic beads by adding 3 μg protein to 10 μl of beads in a reaction volume of 200 μl in a buffer consisting of phosphate buffered saline and 0.01% Tween-20, and incubating for 1 hour at 4° C. with rotation. Following this incubation, beads were captured using a magnetic stand, and washed 3 times with selection buffer consisting of 50 mM HEPES, pH 7.4, 150 mM NaCl, 6 mM KCl, 2.5 mM $MgCl_2$, 2.5 mM $CaCl_2$, 0.01% Tween-20 and 10 mM imidazole, and the selection buffer was then removed. Selection of DNA aptamers to complement fD was conducted as outlined in Table 7. For each round of selection, the DNA library was radiolabeled on the 5' terminus of the library with $^{32}P$ to facilitate tracking of the library during the selection cycle. Typically, >20,000 CPM of library was used as tracer in each round, with the remaining input DNA unlabeled. For each round of selection, the DNA library was heated to 90° C. for 5 minutes, then cooled on ice for 5 minutes, and at room temperature for an additional 20 minutes. Following this library renaturation step, the selection rounds were initiated by resuspending the bead-immobilized fD in the library mixture. The library and fD were then incubated for 30 minutes at 37° C. with rotation. Following this binding reaction, the beads containing immobilized fD were washed, and then fD bound aptamers eluted as described in Table 7. In the first round of the selection, the library was composed of approximately $1-2 \times 10^{15}$ unique sequences.

TABLE 7

Selection conditions

| | Selection Library Input | | Target protein | | | |
|---|---|---|---|---|---|---|
| Round | Picomoles | Conc. (μM) | Picomoles | Conc. (μM) | Wash Conditions | Elution Conditions |
| 1 | 3000 | 15 | 1000 | 5 | 200 μl, 37° C., 3x at 1 minute per | E1: 200 μl, 90° C., 10 min; E2: 200 μl, 90° C., 10 min |
| 2 | 600 | 15 | 200 | 5 | 40 μl, 37° C., 3x at 1 minute per | E1: 40 μl, 90° C., 10 min; E2: 40 μl, 90° C., 10 min; E3: 40 μl, 90° C., 10 min |
| 3 | 600 | 15 | 200 | 5 | 40 μl, 37° C., 3x at 1 minute per | E1: 40 μl, room temperature, 10 min; E2: 40 μl, 90° C., 10 min; E3: 40 μl, 90° C., 10 min |
| 4 | 600 | 15 | 200 | 5 | 40 μl, 37° C., 3x at 1 minute per | E1: 40 μl, room temperature, 10 min; E2: 40 μl, 90° C., 10 min; E3: 40 μl, 90° C., 10 min |
| 4-repeat | 600 | 15 | 200 | 5 | 40 μl, 37° C., 3x at 1 minute per | E1: 40 μl, room temperature, 10 min; E2: 40 μl, 90° C., 10 min; E3: 40 μl, 90° C., 10 min |
| 5 | 600 | 15 | 200 | 5 | 40 μl, 37° C., 3x at 1 minute per | E1: 40 μl, room temperature, 10 min; E2: 40 μl, 90° C., 10 min; E3: 40 μl, 90° C., 10 min |
| 6 | 600 | 15 | 200 | 5 | 40 μl, 37° C., 3x at 1 minute per | E1: 40 μl, room temperature, 10 min; E2: 40 μl, 90° C., 10 min; E3: 40 μl, 90° C., 10 min |
| 7 | 600 | 15 | 200 | 5 | 40 μl, 37° C., 3x at 1 minute per | E1: 40 μl, room temperature, 10 min; E2: 40 μl, 90° C., 10 min; E3: 40 μl, 90° C., 10 min |
| 8 | 600 | 15 | 200 | 5 | 40 μl, 37° C., 3x at 1 minute per | E1: 40 μl, room temperature, 10 min; E2: 40 μl, 90° C., 10 min; E3: 40 μl, 90° C., 10 min |
| 9 | 600 | 15 | 200 | 5 | 40 μl, 37° C., 3x at 1 minute per | E1: 40 μl, room temperature, 10 min; E2: 40 μl, 90° C., 10 min; E3: 40 μl, 90° C., 10 min |

TABLE 7-continued

Selection conditions

| Round | Selection Library Input Picomoles | Conc. (µM) | Target protein Picomoles | Conc. (µM) | Wash Conditions | Elution Conditions |
|---|---|---|---|---|---|---|
| 10 | 600 | 15 | 200 | 5 | 40 µl, 37° C., 3x at 1 minute per | E1: 40 µl, room temperature, 10 min; E2: 40 µl, 90° C., 10 min; E3: 40 µl, 90° C., 10 min |
| 11 | 600 | 15 | 200 | 5 | 40 µl, 37° C., 3x at 1 minute per | E1: 40 µl, room temperature, 10 min; E2: 40 µl, 90° C., 10 min; E3: 40 µl, 90° C., 10 min |
| 12 | 600 | 15 | 200 | 5 | 40 µl, 37° C., 3x at 1 minute per | E1: 40 µl, room temperature, 10 min; E2: 40 µl, 90° C., 10 min; E3: 40 µl, 90° C., 10 min |

DNA recovered in elution 1 was used as template for PCR 1 to generate an archival pool for each selection round. The product from PCR 1 was subsequently used as template material for bulk PCR 2 amplification to regenerate the library for further rounds of selection, binding assays and sequencing pools. PCR reactions were setup in 50 µL volumes containing 5 µL Elution 1 eluent, 500 nM forward primer, 500 nM reverse primer 1, 200 µM dNTP, 1×PCR buffer, and 2.5u Taq DNA Polymerase. Reactions were cycled at 95° C. for 1 minute, followed by repeating cycles of 95° C. for 30 seconds, 55° C. for 45 seconds and 72° C. for 55 seconds. The optimal number of amplification cycles for each round was determined by analyzing aliquots from even PCR cycles to check for appropriate product size and yield. In early selection rounds (1-4) the entire elution 1 eluent volume was used for PCR 1 amplification by performing multiple reactions followed by pooling. In later rounds, ~10% of the elution 1 eluent was used for PCR 1. The pooled reactions from the amplification cycle determined by agarose gel to be optimal were diluted 1:50 in water and archived at −20° C.

To generate the library for the next round of selection, diluted PCR 1 product was used as template in place of selection eluent, and PCR was conducted under cycle conditions as PCR 1, using the forward primer with the blocked reverse primer 2. After cycling, PCR reactions were pooled and concentrated by ethanol precipitation. Concentrated PCR reactions were then gel purified prior to use, with the sense strand (80 nucleotide product) being eluted and carried forward to the next round of selection.

The progress of the selection was monitored by double-filter nitrocellulose filter binding by measuring the fraction of the library bound with 100 nM input DNA and 5 µM human fD. As shown in Table 8, the fraction of the library bound increased over the course of the selection, indicating an enrichment of fD aptamers in the library as the selection progressed from round 0

TABLE 8

Progress of DNA selection of human fD

| Round | % of Library Bound |
|---|---|
| 0 | 0.88 |
| 1 | 1.13 |
| 2 | 1.22 |

TABLE 8-continued

Progress of DNA selection of human fD

| Round | % of Library Bound |
|---|---|
| 3 | 1.68 |
| 4 | 2.55 |
| 5 | 3.03 |
| 6 | 11.26 |
| 7 | 9.56 |
| 8 | 10.99 |
| 9 | 14.64 |

Selected DNA pools from rounds 2 to 8 were analyzed by deep sequencing. In round 8, both elution 1 and elution 2 were sequenced as separate pools, R8E and R8E2 respectively. Sequencing libraries for individual selection rounds were prepared using the archived primary PCR product as template and amplified in a PCR reaction using forward and reverse library primers modified to include binding and barcoding sequences for multiplexed Illumina DNA sequencing. Sequencing reactions were run on an Illumina MiSeq sequencer using a 150 bp paired end read kit. Raw sequencing data consists of paired-end sequence and read quality data in two FASTQ format files, one for each DNA strand.

Forward and reverse library primer sequences were trimmed from the forward and reverse reads respectively using the Cutadapt software package. The trimmed forward and reverse reads were then merged into a consensus sense overlap sequence using the USEARCH software package. Only sequences which possessed perfect complementarity in the overlap region were passed on to yield a FASTA file containing sense reads of only the random library domain. This random domain sequence file was then dereplicated using USEARCH to produce a FASTA file containing only unique sequences with sequence identifiers noting the copy number of each unique sequence. The sequence diversity of each round of the selection was determined by comparing the total number of sequences after read merging to the number of unique sequences after dereplication. This data is summarized in Table 9.

Analysis of the base frequency was calculated by importing unique sequence reads into Excel and determining the base composition of each sequence with copy >1 using custom VBA scripts. The overall base composition for enriched rounds was then expressed as a mean and standard deviation of unique sequence base compositions in the round of interest.

Cross-round sequence analysis was performed by importing unique sequence reads into Excel for all rounds of interest. One sequence round was chosen as the query round, typically the latest selection round, to be used as the reference for sequence data ranking. Using built-in Excel functions, query sequences were cross referenced across other sequencing rounds to build a table showing the fractional representation of a given sequence across rounds.

Multiple sequence alignments (MSA) were performed using the 50 most abundant unique sequences processed through the MUSCLE software package. The resulting alignment file in FASTA format was converted to a sequence logo using the WebLogo software package.

TABLE 9

Summary of sequence data from rounds 2-8.

| | R2 | R3 | R4 | R5 | R6 | R7 | R8E1 | R8E2 |
|---|---|---|---|---|---|---|---|---|
| Reads | 463925 | 439335 | 478898 | 427651 | 344841 | 391016 | 369265 | 411913 |
| Unique | 456717 | 432321 | 471277 | 421294 | 297829 | 283716 | 230414 | 324189 |
| % Unique | 98% | 98% | 98% | 99% | 86% | 73% | 62% | 79% |

Figure 8:
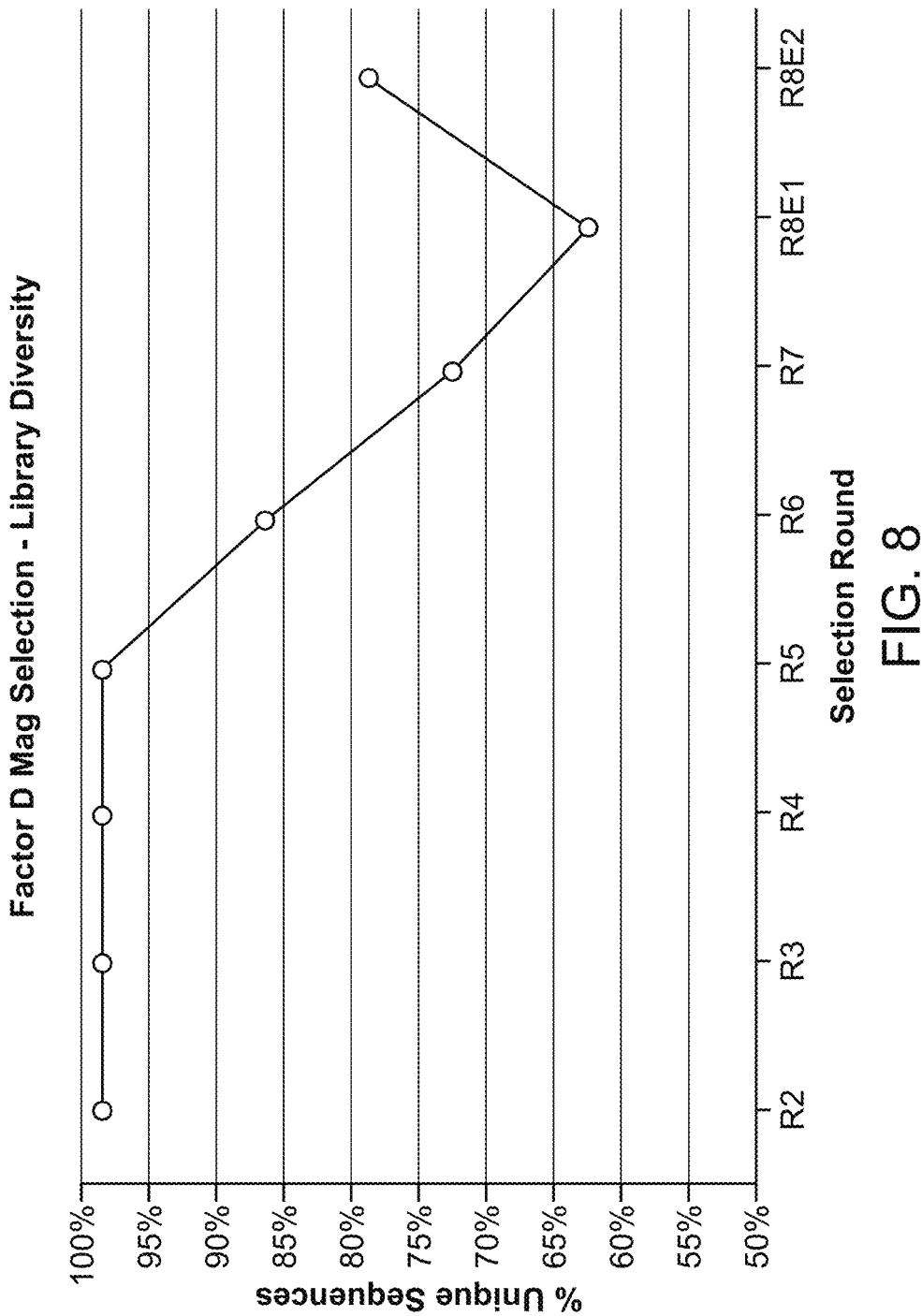
FIG. 8 depicts a plot of the percentage of unique sequences identified during generation of DNA aptamers to human complement fD.

Sequence diversity decreased rapidly after round 5 until round 8, decreasing approximately 12% per round (FIG. 8). The harsher R8E2 elution condition yielded a population with greater diversity compared to the relatively mild elution condition in R8E1.

Figure 9:
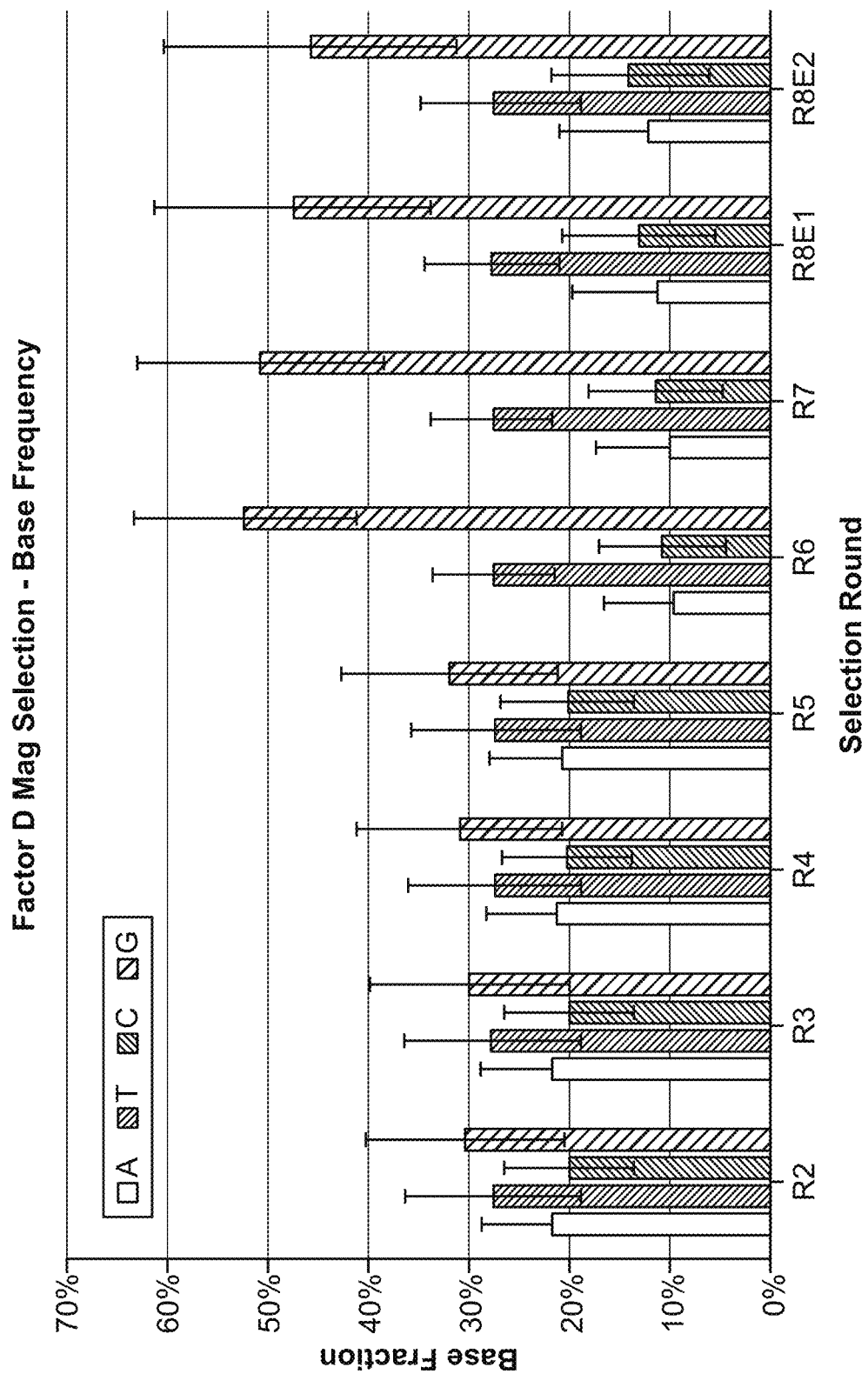
FIG. 9 depicts a plot of the average base frequency across rounds of selection for DNA aptamers to human complement fD.

Coinciding with the diversity trend in FIG. 8, the distribution of base composition changed dramatically between rounds 5 and 6 (FIG. 9), with guanine-rich sequences dominating in rounds 6 through 8.

TABLE 10

Sequences of DNA Aptamers to fD.

| SEQ ID NO. | Sequence Rank | Sequence (5' to 3') |
|---|---|---|
| SEQ ID NO: 4 | 1 | GTGACGACTGACATATCTGCTCCGAGGTTATTGGGGTTGGGGCCTGGGCGATTGGGGCCTCGTAGTTGAGTCTGAGTGCT |
| SEQ ID NO: 5 | 2 | GTGACGACTGACATATCTGCGTTTGGGGTTGGGGCCTGGGAGTTTGGGGAGCAGAAAGGACGTAGTTGAGTCTGAGTGCT |
| SEQ ID NO: 6 | 3 | GTGACGACTGACATATCTGCTGTGGGTGTTGTGGGGGTGGGTGGTGGGCCCTTCGCCATGCGTAGTTGAGTCTGAGTGCT |
| SEQ ID NO: 7 | 4 | GTGACGACTGACATATCTGCGGCGGTTGGGGTCGAAGGGCGAGGGGTGGGAGGTCGCCGTAGTTGAGTCTGAGTGCT |
| SEQ ID NO: 8 | 5 | GTGACGACTGACATATCTGCTATTTTGGGGCCTGGGTGTTGGGGATTGGGGACTATGTGTCGTAGTTGAGTCTGAGTGCT |
| SEQ ID NO: 9 | 6 | GTGACGACTGACATATCTGCTGTGGATGGTGGGGGGTGGTGTGGGAGGGCTGGTCGTCGCGTAGTTGAGTCTGAGTGCT |
| SEQ ID NO: 10 | 7 | GTGACGACTGACATATCTGCCCTATAGGGGTGTGGGCGAGGGGTGGGTGGTAGGGCGGCTCGTAGTTGAGTCTGAGTGCT |
| SEQ ID NO: 11 | 8 | GTGACGACTGACATATCTGCGGAGGTGGGTGGGTGGGTGCGTGCGAGGGCGGTAGGTCCGTAGTTGAGTCTGAGTGCT |
| SEQ ID NO: 12 | 9 | GTGACGACTGACATATCTGCAAAAGTTAGATTGACATGGTATGCACCGTCTGAGGTTGGTCGTAGTTGAGTCTGAGTGCT |
| SEQ ID NO: 13 | 10 | GTGACGACTGACATATCTGCACCACGCTAGGGGTGAGGGCGAGGGGTGGGTAGCGCGTGGCGTAGTTGAGTCTGAGTGCT |
| SEQ ID NO: 14 | 11 | GTGACGACTGACATATCTGCTGTGGGTGTTGTGGGGCGGGTGGTGGGTGCGTCGGTGGTCGTAGTTGAGTCTGAGTGCT |
| SEQ ID NO: 15 | 12 | GTGACGACTGACATATCTGCTGCTTCCAGCGGTCATGATATGCACTGTCTGAAGCTCGGTCGTAGTTGAGTCTGAGTGCT |
| SEQ ID NO: 16 | 13 | GTGACGACTGACATATCTGCTGTGTTATGATATGCACCGTCTGAGGGTAGTCGCGGGGTGCGTAGTTGAGTCTGAGTGCT |
| SEQ ID NO: 17 | 14 | GTGACGACTGACATATCTGCTGCTTGTTTAGTGGGTGGGTGGGTGGTGTGGTGGTGATGCGTAGTTGAGTCTGAGTGCT |
| SEQ ID NO: 18 | 15 | GTGACGACTGACATATCTGCCTTGGGGTTGGGGCCTGGGTGTTTGGGGTGGCCTAGAAGTCGTAGTTGAGTCTGAGTGCT |
| SEQ ID NO: 19 | 16 | GTGACGACTGACATATCTGCGCTAGGGGTGGGTTGGGGTTGGTGGTGTGCGTGTGGGTTGCGTAGTTGAGTCTGAGTGCT |
| SEQ ID NO: 20 | 17 | GTGACGACTGACATATCTGCTGTTGAGGTTGGTGGGGGGTGGGCGGTGGGATGGTTGTGCCGTAGTTGAGTCTGAGTGCT |
| SEQ ID NO: 21 | 18 | GTGACGACTGACATATCTGCTTGACAGTCTGCTTTGCAGGGGCCGAGAGCGCCATTGCGTCGTAGTTGAGTCTGAGTGCT |
| SEQ ID NO: 22 | 19 | GTGACGACTGACATATCTGCTGTGGTTGGTGGGGGTGGAGGGTGGGAGGCCGTGTGTCCCGTAGTTGAGTCTGAGTGCT |
| SEQ ID NO: 23 | 20 | GTGACGACTGACATATCTGCTGTGGTGGTGGGGGAGGGTGGTGGGGTGGCCGGCGCTCGTCGTAGTTGAGTCTGAGTGCT |
| SEQ ID NO: 24 | 21 | GTGACGACTGACATATCTGCTGGGTTACGTGGTTCGGGGCTAGGGGGGTGGGGTGTGTTTCGTAGTTGAGTCTGAGTGCT |
| SEQ ID NO: 25 | 22 | GTGACGACTGACATATCTGCTGGTGGTGTGCGGTGGGTTCTTTGGGTGGGATGGGTGGTACCGTAGTTGAGTCTGAGTGCT |

TABLE 10-continued

Sequences of DNA Aptamers to fD.

| SEQ ID NO. | Sequence Rank | Sequence (5' to 3') |
|---|---|---|
| SEQ ID NO: 26 | 23 | GTGACGACTGACATATCTGCTATTAGATCCTCGGTGGGTGGGTGGGTGTGTGGTGGTGTGCGTAGTTGAGTCTGAGTGCT |
| SEQ ID NO: 27 | 24 | GTGACGACTGACATATCTGCGGGCGTCTGAGCGCATGGATGACCCACCGACAGATTGCGGCGTAGTTGAGTCTGAGTGCT |
| SEQ ID NO: 28 | 25 | GTGACGACTGACATATCTGCGCTTTGGGTGGGCTCGGTGTGCGGTGTGCGGGTGGGTTTGCGTAGTTGAGTCTGAGTGCT |
| SEQ ID NO: 29 | 26 | GTGACGACTGACATATCTGCGTTTGGGGTTGGGGCCTGGGAGTTTGGGGAGCAGAAAGGGCGTAGTTGAGTCTGAGTGCT |
| SEQ ID NO: 30 | 27 | GTGACGACTGACATATCTGCGGGTGGGTTGGGTTGGGTTTGGTGGTGGTGCCTGTTAGTTCGTAGTTGAGTCTGAGTGCT |
| SEQ ID NO: 31 | 28 | GTGACGACTGACATATCTGCAGGTGGGTGGGTGGGTGTGTGTGCGGTGGTGTGATTTGGCCGTAGTTGAGTCTGAGTGCT |
| SEQ ID NO: 32 | 29 | GTGACGACTGACATATCTGCTGTGGTTGGTGGGGGGCGGCGGGTGGGGAGCCTGGTGTTCCGTAGTTGAGTCTGAGTGCT |
| SEQ ID NO: 33 | 30 | GTGACGACTGACATATCTGCTCCCGTTTGAGGGCTTGTCGGACAGATTGCTGGCACGTCACGTAGTTGAGTCTGAGTGCT |
| SEQ ID NO: 34 | 31 | GTGACGACTGACATATCTGCTCTTGGTGGTGGTGGGTTGGGATGGGTCTTGGGCTGCCGTAGTTGAGTCTGAGTGCT |
| SEQ ID NO: 35 | 32 | GTGACGACTGACATATCTGCCTGTGAGGGGAGGGAGGGTGGGTTTGGCGGTGGCGCAGGCCGTAGTTGAGTCTGAGTGCT |
| SEQ ID NO: 36 | 33 | GTGACGACTGACATATCTGCGTGGTGGTGCGTGGGTGGTGGGGGGGGGAGCTGGGTGCCCCGTAGTTGAGTCTGAGTGCT |
| SEQ ID NO: 37 | 34 | GTGACGACTGACATATCTGCTGTGGGTGTTGTGGGGTGGGTGGTGGGCCCTTCGCCGTGCGTAGTTGAGTCTGAGTGCT |
| SEQ ID NO: 38 | 35 | GTGACGACTGACATATCTGCTTCCGGTATGTGTGGGTGGGTGGGTGGTGTGGTGGTGTTGCGTAGTTGAGTCTGAGTGCT |
| SEQ ID NO: 39 | 36 | GTGACGACTGACATATCTGCTCTCTTCTGTTGTGGGTGGGTGGGTGGTGTGGTGCGTGTGCGTAGTTGAGTCTGAGTGCT |
| SEQ ID NO: 40 | 37 | GTGACGACTGACATATCTGCGGCTGGGTGGGTTGGGTTAGGGTGGTGTGCGGTGGGTTGCCGTAGTTGAGTCTGAGTGCT |
| SEQ ID NO: 41 | 38 | GTGACGACTGACATATCTGCGTTTAGGTGGGCGGGTGGGTGTGCGGTGGGCGGTGTTGAACGTAGTTGAGTCTGAGTGCT |
| SEQ ID NO: 42 | 39 | GTGACGACTGACATATCTGCGGTGATTGGGGTTGGGGCCTGGGCGTTTGGGGACCGCATGCGTAGTTGAGTCTGAGTGCT |
| SEQ ID NO: 43 | 40 | GTGACGACTGACATATCTGCGTTTGGGGTTGGGGCCTGGGAGTTTGGGGAGCAGAGAGGACGTAGTTGAGTCTGAGTGCT |
| SEQ ID NO: 44 | 41 | GTGACGACTGACATATCTGCTAACTTGTTGGGGTTTGGGGCCTGGGTGTTGGGGTTGTTTCGTAGTTGAGTCTGAGTGCT |
| SEQ ID NO: 45 | 42 | GTGACGACTGACATATCTGCTGGGGTTGGTGGGGGGAGGTGGGTGGGTTATGTGCGCTGGCGTAGTTGAGTCTGAGTGCT |
| SEQ ID NO: 46 | 43 | GTGACGACTGACATATCTGCTGTGGGTGTTGTGGGGGTGGGTTGGTGGGCATTGCGTGTGCGTAGTTGAGTCTGAGTGCT |
| SEQ ID NO: 47 | 44 | GTGACGACTGACATATCTGCGAGTGGGTTCGGTGGTGGTGTGTGGGAGGGTTGGGTACGTCGTAGTTGAGTCTGAGTGCT |
| SEQ ID NO: 48 | 45 | GTGACGACTGACATATCTGCTGGACATGATTGCACCGTATGAGGTTTAGTCGTTAATGTGCGTAGTTGAGTCTGAGTGCT |
| SEQ ID NO: 49 | 46 | GTGACGACTGACATATCTGCAGTGGGGCCTGGGCGTTGGGGTTTGGGGTGCCTCGTCAGTCGTAGTTGAGTCTGAGTGCT |
| SEQ ID NO: 50 | 47 | GTGACGACTGACATATCTGCATGGATTTTCGGTGGGTGGGTGGGTTGGTGTGGTGGTGTGCGTAGTTGAGTCTGAGTGCT |
| SEQ ID NO: 51 | 48 | GTGACGACTGACATATCTGCTGTGGTTGGTGGGGGGTGGGTGGTGGGAAGGTTCCGGTGCCGTAGTTGAGTCTGAGTGCT |
| SEQ ID NO: 52 | 49 | GTGACGACTGACATATCTGCGGTTGGGGTTGGGGCCTGGGTGTTGGGGAGCAGGTAGCACCGTAGTTGAGTCTGAGTGCT |
| SEQ ID NO: 53 | 50 | GTGACGACTGACATATCTGCGGCCTGGGAGGGTTCGGTGGTGGTGCGAGGGTGGGCAAGCCGTAGTTGAGTCTGAGTGCT |

Figure 10:
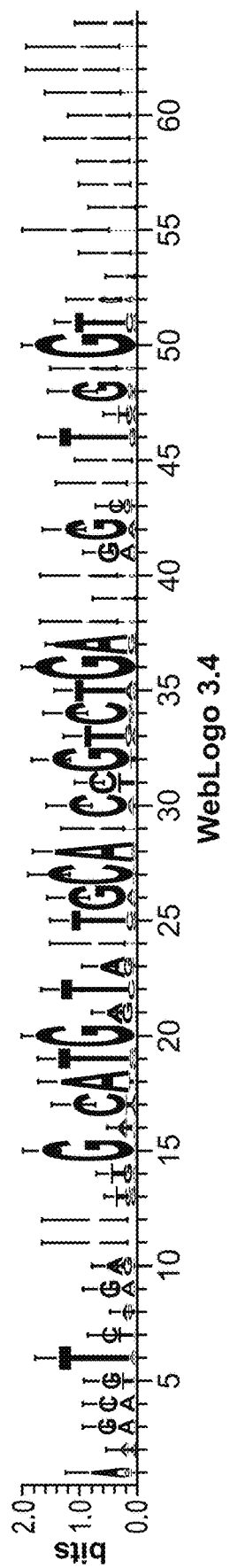
FIG. 10 depicts a sequence logo generated based on multiple sequence alignment of DNA aptamers to human complement fD.

The individual sequence results up to round 8 are shown in Table 10, presented based on the 50 most abundant sequences obtained from the R8E1 sequencing results. These results indicated the dominant DNA aptamer family to human fD is composed of aptamers with the potential to form G-quadruplex structures. Only 6 of the top 50 sequences have compositions containing less than 40% guanine. Comparing enrichment between R8E1 and R8E2 pools, 18% of R8E1 sequences with copy number 210 and possessing >40% G showed enrichment in the second elution, compared to 57% of sequences with <40% G composition. Filtering the sequence data base to remove sequences with 10 copies and >40% G present at >10 copies yielded the sequence logo shown in FIG. 10. This analysis indicated several (3 to 5) minor non-G-quadruplex aptamer families were also identified in this selection.

Potential G-quadruplex and non-G-quadruplex sequences were chosen for analysis of affinity to factor D. Specifically, potential G-quadruplex sequences ranked 1, 2, 4, 5 and 7, and non-G-quadruplex sequences ranked 9, 12 and 24 in Table 11 were synthesized by solid phase DNA synthesis, gel purified, and end labeled to assess binding to fD in the double-filter nitrocellulose filter binding assay. Specificity of binding was assessed by measuring binding to casein. In all binding reactions, the oligonucleotide concentration was 100 nM, the fD concentration 5 µM and the casein concentration 20 µM. As shown in Table 11, several selected sequences showed specific binding to fD, indicating the selection successfully generated DNA aptamers to human complement fD, with members of the G-quadruplex family exhibiting the highest affinity and specificity for human complement fD.

TABLE 11

Analysis of binding of selected oligonucleotides to fD.

| SEQ ID NO. | Sequence Rank | Sequence (5' to 3') | % Bound fD | % Bound Casein |
|---|---|---|---|---|
| SEQ ID NO: 67 | Naïve library | GTGACGACTGACATATCTGC-NNNNNNNNNNNNNNNNNNNN NNNNNNNNNNNNNNNNNNNN-CGTAGTTGAGTCTGAGTGCT | 3.6 | 0.5 |
| SEQ ID NO: 4 | 1 | GTGACGACTGACATATCTGC TCCGAGGTTATTGGGGTTGG GGCCTGGGCGATTGGGGCCT CGTAGTTGAGTCTGAGTGCT | 58.3 | 0.5 |
| SEQ ID NO: 5 | 2 | GTGACGACTGACATATCTGC GTTTGGGGTTGGGGCCTGGG AGTTTGGGGAGCAGAAAGGA CGTAGTTGAGTCTGAGTGCT | 63.0 | 0.5 |
| SEQ ID NO: 7 | 4 | GTGACGACTGACATATCTGC GGCGGTTGGGGTCGAAGGGC GAGGGGTGGGAGGTCGCCGT AGTTGAGTCTGAGTGCT | 3.2 | 0.1 |
| SEQ ID NO: 8 | 5 | GTGACGACTGACATATCTGC TATTTTGGGGCCTGGGTGTT GGGGATTGGGGACTATGTGT CGTAGTTGAGTCTGAGTGCT | 60.3 | 0.3 |
| SEQ ID NO: 10 | 7 | GTGACGACTGACATATCTGC CCTATAGGGGTGTGGGCGAG GGGTGGGTGGTAGGGCGGCT CGTAGTTGAGTCTGAGTGCT | 1.9 | 0.2 |
| SEQ ID NO: 12 | 9 | GTGACGACTGACATATCTGC AAAAGTTAGATTGACATGGT ATGCACCGTCTGAGGTTGGT CGTAGTTGAGTCTGAGTGCT | 1.6 | 0.6 |
| SEQ ID NO: 15 | 12 | GTGACGACTGACATATCTGC TGCTTCCAGCGGTCATGATA TGCACTGTCTGAAGCTCGT CGTAGTTGAGTCTGAGTGCT | 0.4 | 0.2 |
| SEQ ID NO: 27 | 24 | GTGACGACTGACATATCTGC GGGCGTCTGAGCGCATGGAT GACCCACCGACAGATTGCGG CGTAGTTGAGTCTGAGTGCT | 0.7 | 0.6 |

Example 3. Selection of Base Modified Antamers to fD

A. Preparation of Bead-Immobilized, Base-Modified Aptamer Libraries

Bead-immobilized, base-modified libraries for selection of aptamers to fD were constructed as follows. Briefly, polystyrene beads were used to synthesize bead-based library designs. Representative random regions are shown in Table 12. For each library, synthesis was performed on four separate columns with a pool and split step after every second base to create a random region of fifteen two-base blocks based on a software-generated design. The two-base block library design enables a means to identify sites of incorporation of base-modified residues during analysis of the resultant aptamer sequence data. 5-Position-modified deoxyuridine residues (in bold) were randomly scattered in the random region. This allows for library sequences that have from zero to twelve modifications. The three modifications used in this example (indoles, phenols and primary amines) were introduced with modified nucleoside phosphoramidites during library synthesis.

TABLE 12

Design of Base-Modified, Bead-Immobilized Libraries for Aptamer Selection

| SEQ ID NO. | Column Position | Random Region (5' to 3', 30 nt) |
|---|---|---|
| SEQ ID NO: 81 | 1 | WC*AT*GC*CA*TT*AC*TC*WC*GA* CT*GY*GC*CW*GA*AT |
| SEQ ID NO: 82 | 2 | CC*TG*WG*AG*CC*TG*AT*CG*AG* AC*AT*GT*CG*GA*AG |
| SEQ ID NO: 83 | 3 | GT*CT*AC*CT*TC*TA*XA*AA*GG* GT*CC*TC*TT*TA*CW |
| SEQ ID NO: 84 | 4 | CA*GG*TT*TG*GY*CT*YG*TA*TT* GC*CG*AW*YG*CC*CA | where
W = 5-(indole-3-acetamido-1-propenyl)-2'-deoxyuridine;
X = 5-(amino-1-propenyl)-2'-deoxyuridine;
Y = 5-(4-pivaloylbenzamido-1-propenyl)-2'-deoxyuridine A. Preparation of Bead Immobilized Human Complement fD.

Human complement fD was resuspended at 5 μM final concentration in PBS, pH 7.2, and 100 μL of fD was combined with 1 μL of 20 mM EZ-Link™ NHS-PEG4 Biotin and incubated 2 hours on ice. Following this incubation, unreacted biotin was removed by dialysis into selection buffer B (PBS pH 7.4 (10 mM phosphate buffer, 137.5 mM NaCl), 5.7 mM KCl, 1 mM $MgCl_2$, 1 mM $CaCl_2$), and 0.05% Tween), the biotin incorporation determined and then the biotinylated fD was diluted to 500 nM in selection buffer B.

Prior to the selection of X-Aptamers (XA), biotinylated fD was coupled to Dynabeads® M-280 Streptavidin Beads. M-280 beads were washed 3× in 250 μL buffer B and resuspended in 100 μL buffer B, and then 100 μL of 500 nM biotinylated fD was added, and the solution was incubated at room temperature with rotation for 30 minutes. The fD-coupled beads were then captured using a magnetic stand, washed 3× by gentle inversion with 200 μl buffer B, and resuspended in 100 μl of selection buffer A (PBS pH 7.4 (10 mM phosphate buffer, 137.5 mM NaCl), 5.7 mM KCl, 1 mM $MgCl_2$, 1 mM $CaCl_2$, 0.2% BSA and 0.05% Tween).

B. XA Library Preparation and Negative Selection Against M-280 Beads.

The bead-coupled XA Library was resuspended in 10 mL of buffer B, and washed by centrifugation at 3,000 rcf for 10 minutes, and the supernatant removed. The XA library was then resuspended in 3 mL of buffer B, heated at 95° C. for 5 minutes, and then cooled for 30 minutes at room temperature to renature the bead-immobilized XA library. The renatured XA library was then washed by adding 7 mL of buffer B, followed by centrifugation as before and resuspended in 1.8 mL buffer A. A 250 μL aliquot of non-fD coupled M-280 beads was washed 3× with 500 μL buffer A, resuspended in final volume of 50 μL buffer A, and transferred to the tube containing the XA library. The XA library and non-fD coupled beads were incubated for 1 hour at 37° C. with rotation to allow any XA aptamers with affinity to the M-280 beads to bind to the M-280 beads. Following this incubation, the M-280 beads and any associated bead-immobilized XA library were collected on the magnetic stand, and the supernatant containing unbound XA library was removed and transferred to a fresh tube. The M-280 beads were gently washed 4× with 500 µL of buffer A, and the supernatants from each wash combined with the prior supernatant to generate a pool of XA library beads, pre-cleared of those with affinity to the M-280 streptavidin beads. The pre-cleared XA library was subsequently washed 3× with 10 mL buffer A, and resuspended in 1.8 mL buffer A prior to use in selection of aptamers to fD.

C. Isolation of X-Aptamers to fD.

To identify X-aptamers to fD, the 100 µL of M-280 immobilized fD was added to the pre-cleared XA library, and incubated for 90 minutes at 37° C. with rotation to enable binding of X-aptamers with affinity for fD to the M-280 bead coupled fD. Following the incubation, X-aptamers bound to fD were isolated by collection of the X-aptamer/fD-coupled M-280 beads complex using the magnetic stand, and the supernatant discarded. The X-aptamer/fD-coupled M-280 beads were then washed 8× with 1 mL of buffer A, followed by 2× with 1 mL buffer B, with all wash buffers having been pre-warmed to 37° C. The X-aptamer/fD-coupled M-280 beads, now enriched for aptamers to fD, were then resuspended in 50 µL of buffer B.

Aptamers enriched to fD were then cleaved from beads by addition of an equal volume of 1 N NaOH and incubation at 65° C. for 30 minutes, followed by neutralization of the solution with 2 M Tris-Cl at a volume equivalent to 80% of the cleavage reaction. The aptamers to fD cleaved from the XA library beads were then desalted into selection buffer B.

To further enrich the isolated X-aptamers for those with affinity to fD, 15 µL of the cleaved XA pool was incubated with 100 nM biotinylated fD in selection buffer B in a total volume of 150 µL, and incubated at 37° C. for 1 hour with rotation. X-aptamers were isolated by addition of 5 µL of M-280 beads, followed by incubation for 30 minutes at 37° C., and subsequently captured with a magnetic stand and washed 3× with 150 µL of buffer B pre-warmed to 37° C., and resuspended in 100 µL buffer B to generate an X-aptamer pool enriched for aptamers to fD. To generate controls for sequence comparison, separate reactions containing 15 µL of cleaved pool in a final volume of 150 µL selection B was prepared and incubated without (start control) or with (negative control) 5 µL of M-280 beads and processed per the cleaved pool incubated with fD.

D. Preparation of Isolated X-Aptamer Pools for Sequencing.

A PCR reaction was prepared for the fD enriched X-aptamer pool as well as the start and negative control reactions by combining 5 µL of the isolated X-aptamers or control pools as template for each of 5×20 µL PCR reactions containing 1×PCR buffer, 2.5 mM MgCl$_2$, 0.2 mM dNTPs, 0.4 µM forward primer and 0.4 µM of reverse primer, with each set of PCR reactions containing a unique reverse primer containing a 6-nucleotide index for next generation sequencing, and 1 unit Taq polymerase. PCR reactions were cycles were run using an initial denaturation 94° C. for 1 minute, followed by cycles of 94° C. for 30 seconds; 50° C. for 30 seconds; 72° C. for 1 minute, with a final extension of 72° C. for 3 minutes. The appropriate number of PCR cycles for each condition was determined in initial pilot PCR reactions. PCR products were subsequently purified using a Qiagen MinElute PCR Purification Kit, and subjected to next generation sequencing.

Sequences obtained from the selection strategy were analyzed as follows. Briefly, sites of base-modifications were restored to the individual sequences based on the two-base block synthetic codes and the design of the library. Frequencies for each sequence for each condition were determined, and normalized across each condition, and those sequences with approximately 2× or greater enrichment over the control fractions were identified as potential fD aptamers.

As shown in Table 13, this approach led to the identification of a number of base-modified X-aptamers enriched against human complement fD.

TABLE 13

Sequences of Base-Modified DNA Aptamers to fD.

| SEQ ID NO | Sequence (5' to 3')* | Occurrence in fD pool | Occurrence in Start pool | Occurrence in negative control pool |
|---|---|---|---|---|
| SEQ ID NO: 54 with modifications | ACCTAGTTTGGCTTGCAXAAGTAACYA GCACGTGGGCTAG where X = 5-(amino-1-propenyl)-2'-deoxyuridine; Y = 5-(4-pivaloylbenzamido-1-propenyl)-2'-deoxyuridine | 8632 | 2703 | 1695 |
| SEQ ID NO 55 with modifications | ACGATCGCCCCYGTCTWTAAGAXCGAA TACTATGGGCTAG where W = 5-(indole-3-acetamido-1-propenyl)-2'-deoxyuridine; X = 5-(amino-1-propenyl)-2'-deoxyuridine; Y = 5-(4-pivaloylbenzamido-1-propenyl)-2'-deoxyuridine | 6029 | 3131 | 1669 |
| SEQ ID NO 56 with modifications | ACCTAGAAAGGCTTAGTGAAGTAAWGA TCAGGGCGGGATC where W = 5-(indole-3-acetamido-1-propenyl)-2'-deoxyuridine | 5966 | 4311 | 2961 |
| SEQ ID NO: 57 with modifications | ACCTAGTTCCCYGTCTAXYAGAXCCGA GXGTATGCCGATC where X = 5-(amino-1- | 4379 | 2487 | 2114 |

TABLE 13-continued

Sequences of Base-Modified DNA Aptamers to fD.

| SEQ ID NO | Sequence (5' to 3')* | Occurrence in fD pool | Occurrence in Start pool | Occurrence in negative control pool |
|---|---|---|---|---|
| | propenyl)-2'-deoxyuridine; Y = 5-(4-pivaloylbenzamido-1-propenyl)-2'-deoxyuridine | | | |
| SEQ ID NO: 58 with modifications | ACCTAGGCAGTCTTGCCGAATTTACGA GXGGGGAGGGATC where X = 5-(amino-1-propenyl)-2'-deoxyuridine | 4062 | 269 | 55 |
| SEQ ID NO: 59 with modifications | ACGATCACTGCYCAGCWTYATTAACYA GCYTCGACCCTAG where W = 5-(indole-3-acetamido-1-propenyl)-2'-deoxyuridine; Y = 5-(4-pivaloylbenzamido-1-propenyl)-2'-deoxyuridine | 3300 | 1793 | 1554 |
| SEQ ID NO: 60 with modifications | ACGATCTTCCGCCAGCTGYATTXCGAA GXGCGTGAGGATC where X = 5-(amino-1-propenyl)-2'-deoxyuridine; Y = 5-(4-pivaloylbenzamido-1-propenyl)-2'-deoxyuridine | 3110 | 1589 | 1592 |
| SEQ ID NO 61 with modifications | ACCTAGGCGGTCTTXCCGTCGTTACGT CCYCGGCCCCTAG where X = 5-(amino-1-propenyl)-2'-deoxyuridine; Y = 5-(4-pivaloylbenzamido-1-propenyl)-2'-deoxyuridine | 2539 | 1273 | 1116 |
| SEQ ID NO: 62 with modifications | ACCTAGTTTGGCGTAGCGYATTAAWGG GXGCGGCAGCTAG where W = 5-(indole-3-acetamido-1-propenyl)-2'-deoxyuridine; X = 5-(amino-1-propenyl)-2'-deoxyuridine; Y = 5-(4-pivaloylbenzamido-1-propenyl)-2'-deoxvuridine | 1650 | 715 | 487 |
| SEQ ID NO 63 with modifications | ACGATCGCTGACGTXCAXYAGTATGAG GCACGTGGGCTAG where X = 5-(amino-1-propenyl)-2'-deoxyuridine; Y = 5-(4-pivaloylbenzamido-1-propenyl)-2'-deoxyuridine | 1650 | 594 | 426 |

Sequences listed represent only that portion of the X-aptamer derived from the random region of the X-aptamer library Example 4. Identification of Aptamers that Bind to the Exosite of M with High Affinity In some cases, the disclosure provides for the identification of aptamers that inhibit a function associated with fD. In some cases, the identification of aptamers that that inhibit a function associated with fD may involve performing an alternative complement-dependent hemolysis assay. Human serum that is rendered deficient in the classical complement pathway by depleting C1q may be dependent on alternative complement activity to lyse rabbit red blood cells, an activity that may be dependent on fD. (Katschke, Wu, Ganesan, et al. (2012) Inhibiting alternative pathway complement activation by targeting the Factor D exosite. J. Biol. Chem. 287, 12886-12892).

Briefly, citrated rabbit blood was centrifuged at 500×g for 5 minutes at room temperature. The top plasma fraction was removed and the volume was replaced with 1× Veronal buffer containing 0.1% gelatin (prepared from 5× Veronal buffer, Lonza #12-624E and 2% gelatin solution, Sigma-Aldrich, G1393). The red blood cells were washed two more times. The washed rabbit red blood cells were diluted in 1× Veronal buffer to a concentration of $2 \times 10^9$ cells/mL (RBCs).

In V-bottom 96-well plates the following reagents were added to a final volume of 250 μL: appropriate volume of 1× Veronal buffer with 0.1% gelatin, 100 μL aptamer, 30 μL of C1q-depleted human serum and 20 μL RBCs. This mixture was incubated for 25 minutes at room temperature, then the reaction was stopped by the addition of 5 μL of 500 mM EDTA. The plate was centrifuged for 5 minutes at 500×g at room temperature, then 100 μL of supernatant was removed and the extent of RBC lysis was determined by measuring absorbance at 405 nm. Controls for the assay were provided by complete RBC lysis with water in the absence of C1q- depleted serum, and by inhibition of lysis caused by C1q-depleted serum by 100 µM small molecule fD inhibitor 3,4-dichloroisocoumarin.

Figure 11:
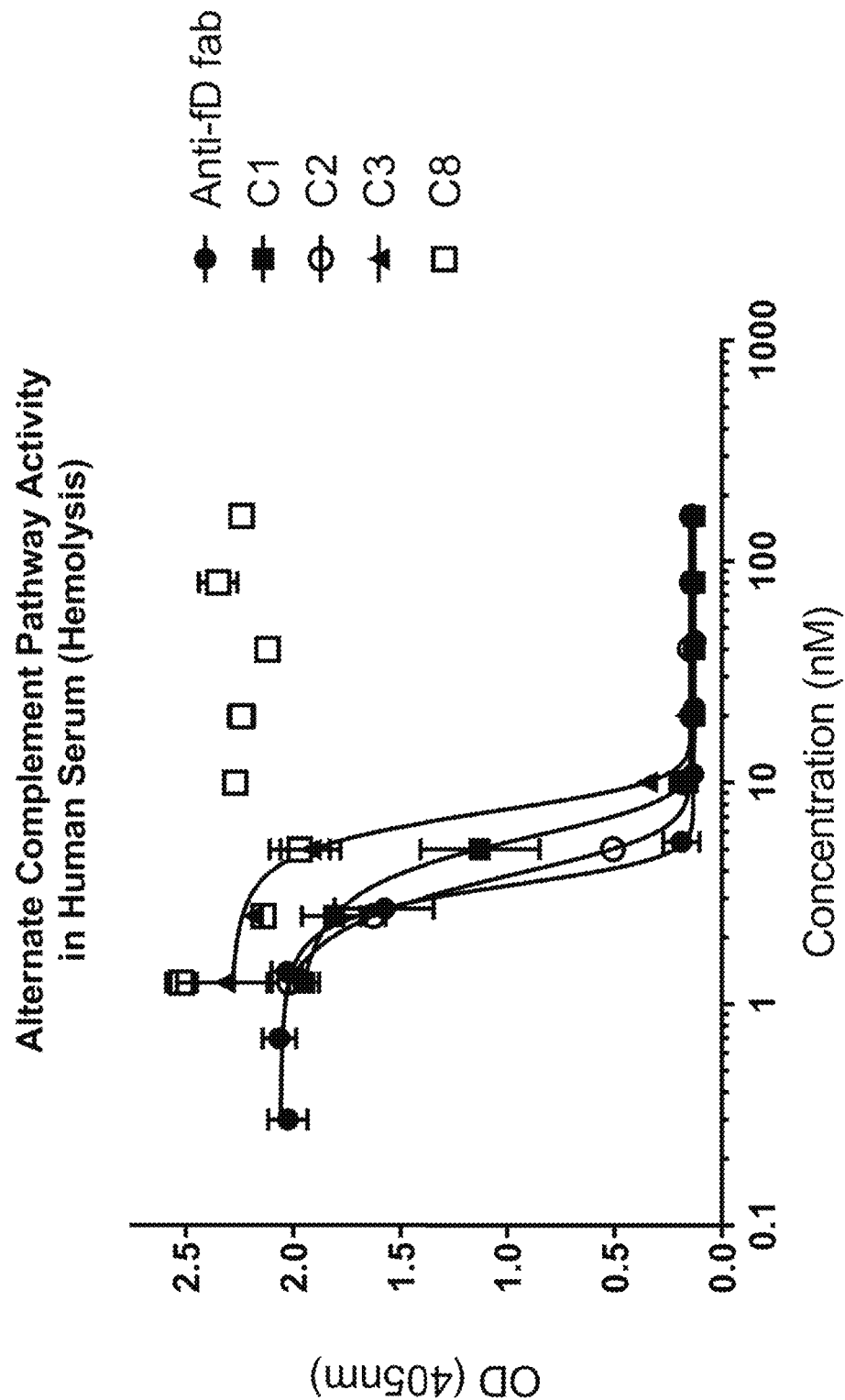
FIG. 11 depicts examples of data obtained from a hemolysis assay according to an embodiment of the disclosure.

C1-C3 identified in Example 1, a non-specific control oligo (C8), and one anti-fD Fab antibody fragment as described in Example 1 (AFD) were incubated with C1q-depleted human serum to allow binding to fD present in the serum, then assayed for the ability to inhibit fD-dependent lysis of rabbit red blood cells (FIG. 11). The endogenous concentration of fD was expected to be about 9.6 nM in 10% C1q-depleted human serum (Loyet, Good, Davancaze et al. (2014) Complement inhibition in cynomolgus monkeys by anti-factor D antigen-binding fragment for the treatment of an advanced form of dry age-related macular degeneration. J. Pharm. Exp. Ther. 351, 527-537), so compounds that bound fD with significantly better affinity, such as less than 1 nM, were expected to bind nearly stoichiometrically to the fD present in the assay. This appeared to be the case for AFD (FIG. 11; Table 14), which was reported to have a low pM affinity for fD (20 nM, Loyet et al. 2014). $IC_{50}$ values for C1-C3, C8 and AFD are depicted in Table 14.

TABLE 14

$IC_{50}$ values for C1-C3, C8 and AFD inhibiting alternative complement in human serum

| Aptamer | AFD | C1 | C2 | C3 | C8 |
|---|---|---|---|---|---|
| $IC_{50}$ (nM) | 3.3 | 5.1 | 3.3 | 7.0 | >160 |

Example 5. Factor D Esterase Activity Assay

In some cases, a fD esterase activity assay may be used to test the activity of putative anti-fD aptamers. In some cases, inhibition of esterase activity may suggest that the anti-fD aptamer is binding to the catalytic cleft and associated substrate binding specificity pockets. In some cases, an enhancement of esterase activity may suggest that the anti-fD aptamer is binding to the exosite in a manner which causes allosteric activation, such as observed for an anti-fD Fab having an amino acid sequence of heavy chain variable region according to SEQ ID NO: 71 and a light chain variable region according to SEQ ID NO: 72. In yet other cases, no effect on esterase activity in combination with inhibition of hemolysis may suggest that the anti-fD aptamer is binding the exosite in manner that does not cause allosteric activation, or is binding to neither the exosite or catalytic cleft. Cleavage of a modified peptide substrate of fD, such as Z-lys-S-Bzl, may be monitored by measuring the amount of reduced 5,5'-Dithiobis(2-nitrobenzoic acid) (DTNB). FD may have a lower catalytic rate than other complement proteases when using peptide thioester substrates, and one such substrate Z-lys-SBzl was found to be cleaved by fD and useful as a synthetic substrate (fD is called protein D in Kam, McRae et al. (1987) Human complement proteins D, C2, and B. J. Biol. Chem. 262, 3444-3451).

In one aspect a molecule that binds fD could block catalytic activity by binding in the catalytic cleft to sterically prevent access of the peptide substrate to the catalytic residues of fD (Katschke, Wu, Ganesan, et al. (2012) Inhibiting alternative pathway complement activation by targeting the Factor D exosite. J. Biol. Chem. 287, 12886-12892). In another aspect a molecule that binds fD could block catalytic activity by an allosteric mechanism that induces structural changes in the enzyme. In a further aspect, a molecule that binds fD could bind to the fD exosite region to sterically inhibit binding of the physiologic substrate protein FB, but not of the synthetic modified peptide substrate Z-Lys-SBzl (Katschke, Wu, Ganesan, et al. (2012) Inhibiting alternative pathway complement activation by targeting the Factor D exosite. J. Biol. Chem. 287, 12886-12892).

In a further aspect where a molecule inhibits fD binding and proteolytic cleavage of FB but not Z-Lys-SBzl, the binding could be similar to how anti-factor D FAb antibody fragment binds to the exosite and induces a subtle conformational change that increases fD cleaving Z-Lys-S-Bzl (Katschke, Wu, Ganesan, et al. (2012) Inhibiting alternative pathway complement activation by targeting the Factor D exosite. J. Biol. Chem. 287, 12886-12892).

Briefly, in flat bottom 96-well plates, the following reagents were added to a final volume of 200 µL: 1× Veronal buffer with 0.1% gelatin and 10 mM $MgCl_2$; anti-fD antibody (AFD), aptamers (C1-C3, see Example 1) or a non-specific oligo control (C8); and a final concentration of fD at or within 5% of 10 nM, 20 nM, 40 nM, 80 nM, or 160 nM. After incubating for 10 min. at room temperature, Z-Lys-SBzl was added at or within 5% of 94 µM, 188 µM, 375 µM, or 750 µM and DTNB at or within 5% of 5 µM, 20 µM, or 40 µM. In some cases, fD was added at 41.7 nM, Z-Lys-SBzl at 375 µM, and DTNB at 20.0 uM. The absorbance was immediately read in a plate reader at 405 nm for 1.5 hours with a read every 30 seconds and a 3 second plate shaking before each read.

Figure 12:
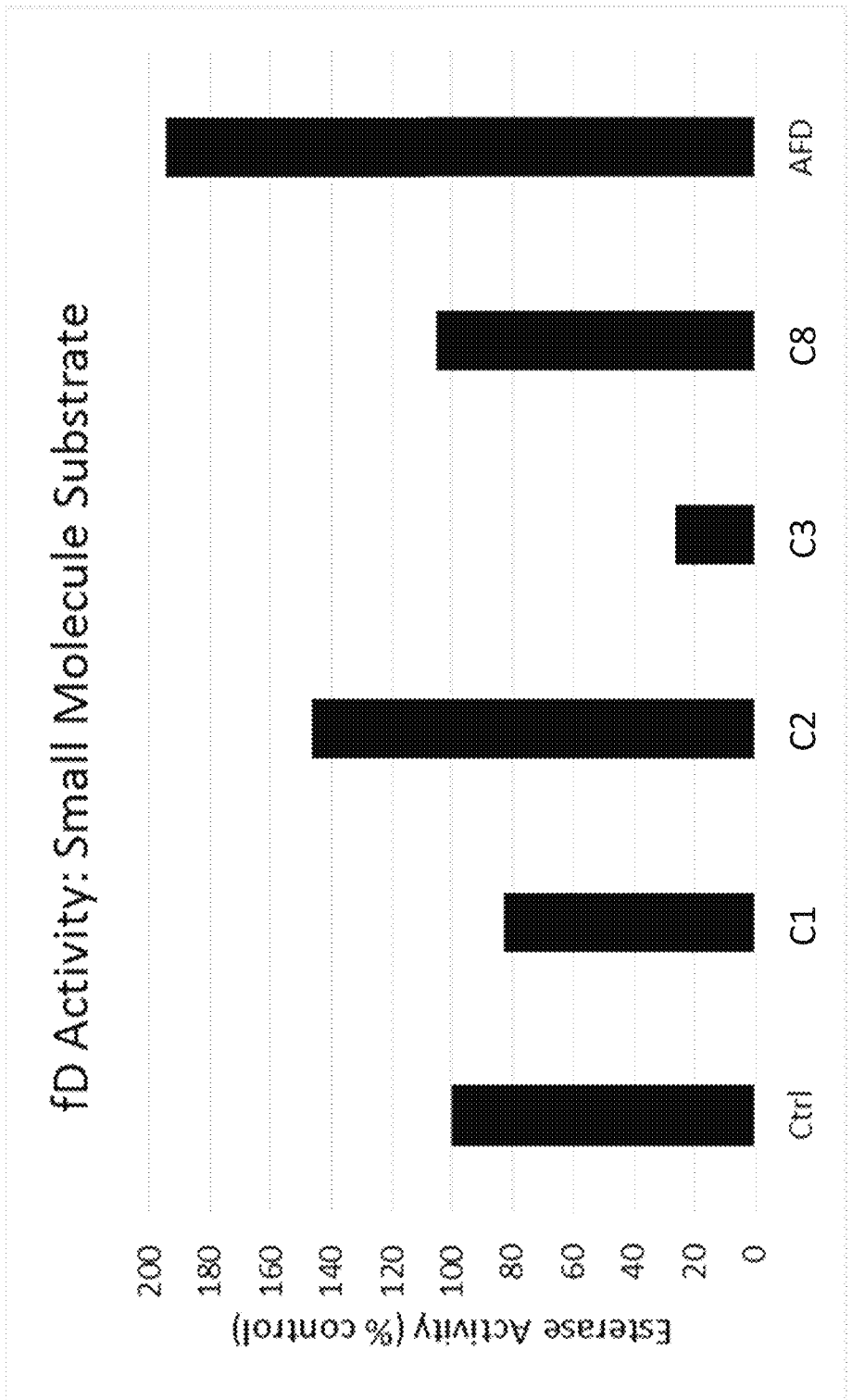
FIG. 12 depicts examples of data obtained from a fD esterase activity assay according to an embodiment of the disclosure.
Figure 13B:
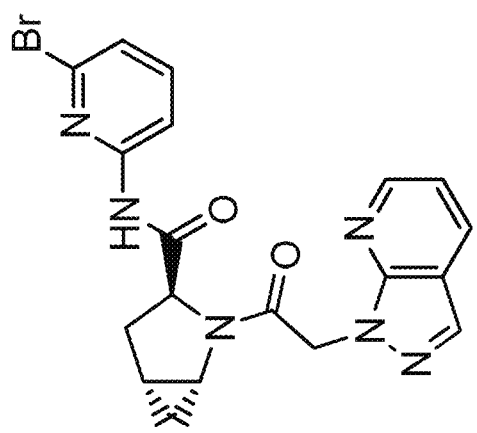
FIG. 13A, FIG. 13B, FIG. 13C, and FIG. 13D depict non-limiting examples of small molecule inhibitors of fD.
Figure 13D:
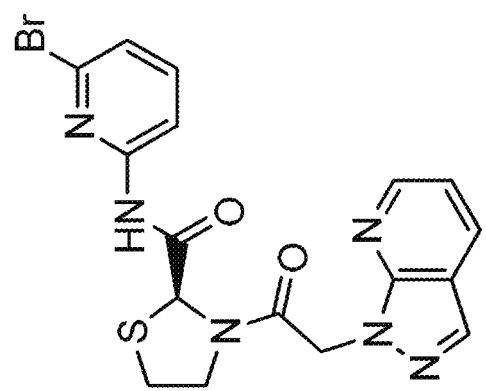
Figure 13A:
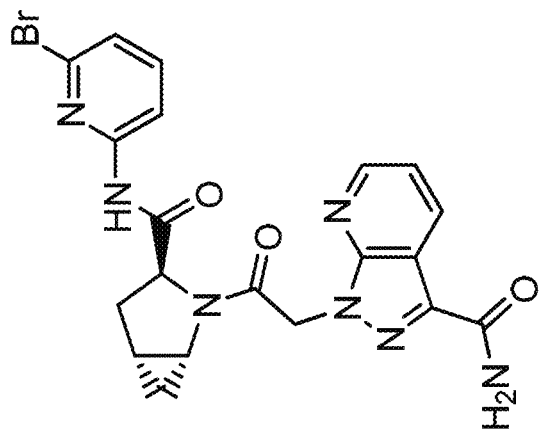
Figure 13C:
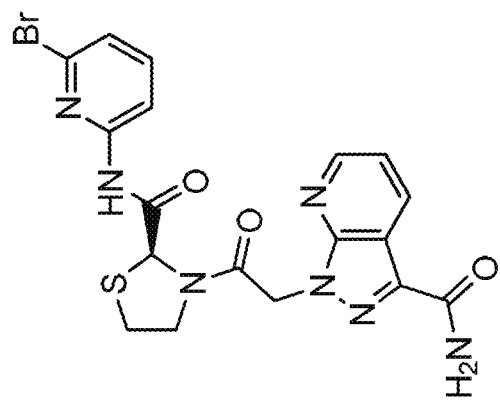

Results of the assay are depicted in Table 15 and FIG. 12. Briefly, C3 was determined to be an active site inhibitor based on having inhibitory activity comparable to a known active site inhibitor of fD, dichloroisocoumarin (DIC). When DIC was used as a positive control in this assay under these conditions, fD activity was reduced to 29±15.8% (mean±SD), which established that C3 was a potent fD inhibitor, operating via the catalytic or active site cleft. The data further established that C2 bound the exosite in a manner similar to that of AFD. The data also established that C1 either worked by a different mechanism of action than C2 and C3, or it functioned like C2 via the exosite, but did not affect fD in exactly the same way to cause allosteric activation of fD.

TABLE 15

Impact of C1, C2, C3, C8 and AFD on fD Esterase activity.

| Aptamer | AFD | C1 | C2 | C3 | C8 |
|---|---|---|---|---|---|
| Activity (%) | 195 | 83 | 147 | 26 | 105 |

Example 6. Identification of fD Inhibitors in Reconstituted Enzymatic fD Assay

In some cases, the disclosure provides for the identification of fD inhibitors in a reconstituted biochemical fD activity assay which is composed of purified proteins fD, FB, and C3b. When fD binds to the complex of FB and C3b (C3bB), FB is cleaved by fD into fragments Ba and Bb (Katschke, Wu, Ganesan, et al. (2012) Inhibiting alternative pathway complement activation by targeting the Factor D exosite. J. Biol. Chem. 287, 12886-12892). The activity of fD can be monitored by the rate of FB cleavage and Ba fragment production using an ELISA that uses an antibody that specifically binds Ba (Quidel, A033).

The FB convertase assay mixture is 0.1% gelatin Veronal buffer and 10 mM $MgCl_2$ with complement proteins fD at or within 5% of 7.5 nM, 15 nM, 30 nM, 60 nM, 120 nM, 240 nM (0.125 µM), factor B (FB) at 125 nM, 250 nM, 500 nM, or 1 µM and C3b at 125 nM, 250 nM, 500 nM, or 1 µM and antibodies or aptamers.

In one example, the concentrations of FB and C3b are equal so they form a 1:1 complex which can then bind fD and allow enzymatically active fD to cleave FB to fragments Ba and Bb. In another example, the FB:C3b complex is present in 4-fold excess of fD. For example, final reaction concentrations of fD of 125 nM and 0.5 µM aptamer (or a concentration range) are mixed for 15 minutes, then 0.5 µM FB and 0.5 µM of C3b are added to the FD/inhibitor mixture and incubated for 30 minutes at 37° C., then 10 mM EDTA in 0.1% gelatin Veronal buffer is added to stop the reaction.

Example 7. Identification of Inhibitors of fD Binding to C3bB

In some aspects, the disclosure provides for the identification of inhibitors of fD binding to FB in complex with C3b. FD is the rate-limiting enzyme in the alternative complement pathway, and converts the proconvertases C3bB and C3b2B to form the active C3 convertase C3bBb or the active C5 convertase C3b2Bb (Katschke et al 2012). For surface plasmon resonance (SPR) to detect fD in a stable complex with FB, catalytically inactive fD (S195A) is used so that it does not cleave the FB upon binding to the FB:C3b complex (Katschke, Wu, Ganesan, et al. (2012) Inhibiting alternative pathway complement activation by targeting the Factor D exosite. J. Biol. Chem. 287, 12886-12892).

When C3b is amine-coupled to a CM5 chip, SPR detects binding of FB as increased mass, and binding of fD to the C3b:FB complex as a further increase in mass. FB, catalytically inactive S195A fD and fD binding compounds in assay buffer (Veronal buffer, 1 mM $NiCl_2$, and 0.05% surfactant P-20) are flowed over the SPR chip at a flow rate of 10, 20, 30, 40, 50, or 60 µL/min, 90 µL. FB is flowed over the immobilized C3b at 0.25, 0.5, 1, 2, or 4 µM, then FB and fD are co-injected at 0.25, 0.5, 1, 2, or 4 µM FB and fD (S195A) at 2-fold dilutions concentration range of 7.8 nM to 8 µM. In some cases, the flow rate is 30 µL/min and the FB concentration is 1 µM, and complexes formed are allowed to dissociate in assay buffer for 5 minutes.

In one example, fD binding compounds are co-injected with a mixture of FB and fD. For example, 1 µM FB and 1 µM fD (S195A) are co-injected with aptamers at a 2-fold dilution range of 1 µM to 128 µM. In one aspect, the fD binding compounds are aptamers that bind fD and prevent fD binding to FB:C3b as determined by a reduced mass detected by SPR.

Example 8. Inhibition of fD in Cell-Based Model Complement Pathology in Stargardt Disease Retinal pigment epithelial (RPE) cells undergo cell death early during the progress of Stargardt disease, and evidence points toward the involvement of the alternative complement pathway (AP) in RPE cell death (Berchuck, Yang, et al (2013) All-trans-retinal (atRal) sensitizes human RPE cells to alternative complement pathway-induced cell death. Invest Ophthalmol Vis Sci 54, 2669-2677). ARPE-19 cells are a spontaneously arising RPE cell line derived from the normal eyes of a 19-year-old male. The ARPE-19 cell line, established using the cuboidal basal cell layer cultured in specific culture media, expresses the RPE-specific markers cellular retinaldehyde binding protein and RPE-65.

Stargardt disease is a hereditary juvenile macular degeneration that occurs in patients with homozygous mutations in the ABCA4 genes, which encode a protein that processes all-trans retinal (Molday (2007) ATP-binding cassette transporter ABCA4: molecular properties and role in vision and macular degeneration. J. Bioenerg Biomembr 39, 507-517). An ABCA4 and RDH8 mouse model of Stargardt disease presents with retinal pathology caused by accumulated atRal, and ABCA4 mutations are present in 16% of AMD patients, suggesting that elevated atRal may contribute to Stargardt disease and AMD disease progression (Berchuck et al 2013).

Mechanistically, atRal decreased expression of CD46 and CD59 on RPE cells in vitro, which increased susceptibility to cell lysis mediated by alternative complement in response to anti-RPE antibody binding to the RPE cell membranes (Berchuck et al 2013).

In some cases, the disclosure provides for the identification of fD inhibitors that inhibit alternative complement-mediated lysis of human retinal pigmented epithelial cells. Briefly, human RPE cells (ARPE-19 cells, ATCC, Manassas, Va., USA) are grown in 1:1 mixture (vol/vol) of Dulbecco's modified Eagle's and Ham's nutrient mixture F-12; (Invitrogen-Gibco, Carlsbad, Calif., USA), non-essential amino acids 10 mM, 0.37% sodium bicarbonate, 0.058% L-glutamine, 10% fetal bovine serum, and antibiotics (penicillin G 100 U/mL, streptomycin sulfate 0.1 mg/mL, gentamicin 10 µg/mL, amphotericin-B 2.5 µg/mL). Cells are incubated at 37° C. in 5% $CO_2$ and 95% relative humidity.

ARPE-19 cells are plated on six-well plates for determining cell viability in an in vitro model of Stargardt disease. 5×10⁵ cells in 2 mL of culture media per well are plated and incubated in standard conditions for 24 hours. To sensitize cells to complement mediated lysis by atRal, ARPE-19 cells are treated with atRal for 90 minutes or 24 hours. To activate the fD-dependent alternative complement pathway, cells are incubated with 24% sheep anti-RPE antibody for 30 minutes and then treated with 6% C1q-depleted human serum. After 90 minutes at 37° C., the supernatant is collected in a 96-well plate and replaced with fresh medium. LDH release is measured in the supernatant using a Cytotoxicity Detection Kit. The effect of fD-neutralizing aptamers is determined in the AP-induced cytotoxicity assay using defined doses (control-no drug, ½×, 1×, 2× and 10×) of all drugs.

Example 9. Treatment of Geographic Atrophy with Anti-fD Aptamer

In this example, a patient is diagnosed with geographic atrophy secondary to AMD. The patient is treated with a therapeutically effective dose of a PEGylated-anti-fD aptamer by intravitreal administration. The aptamer targets the exosite of fD and prevents binding and cleavage of the C3bB complex. The patient is treated once every 4 weeks or once every 8 weeks. After six months of treatment, one year of treatment, and every six months thereafter, the patient is assessed for stabilization of geographic atrophy. The patient shows significantly greater stabilization when compared to an untreated patient and comparable or greater stabilization when compared to a patient who has been treated with an anti-fD antibody fragment therapy once every 4 weeks.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method comprising: administering to a human subject having an ocular disease or disorder a therapeutically effective amount of an aptamer that selectively blocks a catalytic cleft of human complement Factor D, thereby treating the ocular disease or disorder.

2. The method of claim 1, wherein said aptamer inhibits a function associated with human complement Factor D.

3. The method of claim 1, wherein said aptamer is an RNA aptamer or modified RNA aptamer.

4. The method of claim 1, wherein said aptamer inhibits activity of human complement Factor D as measured by a Factor D esterase activity assay as compared to a control.

5. The method of claim 1, wherein said aptamer inhibits activity of human complement Factor D as measured by a hemolysis assay.

6. The method of claim 1, wherein said ocular disease or disorder is selected from the group consisting of: dry age-related macular degeneration, wet age-related macular degeneration, geographic atrophy, and Stargardt disease.

7. The method of claim 1, wherein said therapeutically effective amount is an amount effective to treat said ocular disease or disorder, or an amount effective to ameliorate a symptom associated therewith.

8. The method of claim 1, wherein said administering further comprises administering said therapeutically effective amount of said aptamer to said human subject by intravitreal administration.

9. The method of claim 1, wherein said administering further comprises administering said therapeutically effective amount of said aptamer to said human subject at least once every 8 weeks.

10. The method of claim 1, wherein said administering further comprises administering to said human subject in need thereof a pharmaceutical composition comprising said therapeutically effective amount of said aptamer.

11. The method of claim 1, wherein said human subject is greater than 50 years old.

12. The method of claim 1, wherein said human subject is from 6-20 years old.

13. The method of claim 1, wherein said human subject has one or more mutations in complement factor H, complement component 3, complement component 2, complement factor B, complement factor I, ABC4A, ELOVL4, or any combination thereof.

14. The method of claim 1, wherein said aptamer is conjugated to a polyethylene glycol (PEG) polymer.

15. The method of claim 1, wherein said aptamer comprises one or more modified nucleotides.

16. The method of claim 1, wherein said aptamer has an intravitreal half-life of at least 6 days in a human, an intravitreal half-life of at least 2 days in a rabbit, an intravitreal half-life of at least 3 days in a primate, or any combination thereof.

17. The method of claim 1, wherein said therapeutically effective amount is from about 0.01 mg to about 150 mg of said aptamer in about from 25 µl to about 100 µl volume per eye.

* * * * *

```
                              SEQUENCE LISTING

<160> NUMBER OF SEQ ID NOS: 95

<210> SEQ ID NO 1
<211> LENGTH: 89
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1
gggagugugu acgaggcauu aggccgccac ccaaacugca guccucguaa gucugccugg      60
cggcuuugau acuugaucgc ccuagaagc                                       89

<210> SEQ ID NO 2
<211> LENGTH: 89
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 2
gggagugugu acgaggcauu aguccgccga agucuuuugg cucgguuuuu ucaaggucgg      60
cggcuuugau acuugaucgc ccuagaagc                                       89

<210> SEQ ID NO 3
<211> LENGTH: 89
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 3
gggagugugu acgaggcauu aggccgccac cucguuugau ugcgguuguu cggccgcggg      60
cggcuuugau acuugaucgc ccuagaagc                                       89

<210> SEQ ID NO 4
<211> LENGTH: 80
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
gtgacgactg acatatctgc tccgaggtta ttggggttgg ggcctgggcg attggggcct      60
cgtagttgag tctgagtgct                                                 80

<210> SEQ ID NO 5
<211> LENGTH: 80
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
```
gtgacgactg acatatctgc gtttgggggtt ggggcctggg agtttgggga gcagaaagga        60
cgtagttgag tctgagtgct                                                    80

<210> SEQ ID NO 6
<211> LENGTH: 80
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
gtgacgactg acatatctgc tgtgggtgtt gtgggggtgg gtggtgggcc cttcgccatg        60
cgtagttgag tctgagtgct                                                    80

<210> SEQ ID NO 7
<211> LENGTH: 77
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
gtgacgactg acatatctgc ggcggttggg gtcgaagggc gaggggtggg aggtcgccgt        60
agttgagtct gagtgct                                                       77

<210> SEQ ID NO 8
<211> LENGTH: 80
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
gtgacgactg acatatctgc tattttgggg cctgggtgtt ggggattggg gactatgtgt        60
cgtagttgag tctgagtgct                                                    80

<210> SEQ ID NO 9
<211> LENGTH: 80
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
gtgacgactg acatatctgc tgtggatggt gggggtggt gtgggagggc tggtcggtcg        60
cgtagttgag tctgagtgct                                                    80

<210> SEQ ID NO 10
<211> LENGTH: 80
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
gtgacgactg acatatctgc cctatagggg tgtgggcgag gggtgggtgg tagggcggct        60
cgtagttgag tctgagtgct                                                    80

<210> SEQ ID NO 11
<211> LENGTH: 80
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
gtgacgactg acatatctgc ggaggtgggt gggtgggtgc gtgcgagggc ggtgtaggtc      60
cgtagttgag tctgagtgct                                                 80

<210> SEQ ID NO 12
<211> LENGTH: 80
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
gtgacgactg acatatctgc aaaagttaga ttgacatggt atgcaccgtc tgaggttggt      60
cgtagttgag tctgagtgct                                                 80

<210> SEQ ID NO 13
<211> LENGTH: 80
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
gtgacgactg acatatctgc accacgctag gggtgagggc gaggggtggg tagcgcgtgg      60
cgtagttgag tctgagtgct                                                 80

<210> SEQ ID NO 14
<211> LENGTH: 80
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
gtgacgactg acatatctgc tgtgggtgtt gtggggcgg gtggtgggtg cgtcggtggt      60
cgtagttgag tctgagtgct                                                 80

<210> SEQ ID NO 15
<211> LENGTH: 80
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
gtgacgactg acatatctgc tgcttccagc ggtcatgata tgcactgtct gaagctcggt      60
cgtagttgag tctgagtgct                                                 80

<210> SEQ ID NO 16
<211> LENGTH: 80
<212> TYPE: DNA

```
<213> ORGANISM: Artificial Sequence
<220> FEATURE:
<223> OTHER INFORMATION: Description of Artificial Sequence: Synthetic
      oligonucleotide

<400> SEQUENCE: 16
gtgacgactg acatatctgc tgtgttatga tatgcaccgt ctgagggtag tcgcggggtg    60
cgtagttgag tctgagtgct                                                80

<210> SEQ ID NO 17
<211> LENGTH: 79
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
gtgacgactg acatatctgc tgcttgttta gtgggtgggt gggtggtgtg gtggtgatgc    60
gtagttgagt ctgagtgct                                                 79

<210> SEQ ID NO 18
<211> LENGTH: 80
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
gtgacgactg acatatctgc cttggggttg gggcctgggt gtttggggtg gcctagaagt    60
cgtagttgag tctgagtgct                                                80

<210> SEQ ID NO 19
<211> LENGTH: 80
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
gtgacgactg acatatctgc gctaggggtg ggttggggtt ggtggtgtgc gtgtgggttg    60
cgtagttgag tctgagtgct                                                80

<210> SEQ ID NO 20
<211> LENGTH: 80
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
gtgacgactg acatatctgc tgttgaggtt ggtgggggt gggcggtggg atggttgtgc    60
cgtagttgag tctgagtgct                                                80

<210> SEQ ID NO 21
<211> LENGTH: 80
<212> TYPE: DNA
<213> ORGANISM: Artificial Sequence
<220> FEATURE:
<223> OTHER INFORMATION: Description of Artificial Sequence: Synthetic
      oligonucleotide
```

<400> SEQUENCE: 21
gtgacgactg acatatctgc ttgacagtct gctttgcagg ggccgagagc gccattgcgt     60
cgtagttgag tctgagtgct                                                80

<210> SEQ ID NO 22
<211> LENGTH: 80
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
gtgacgactg acatatctgc tgtggttggt gggggtgga gggtgggagg ccgtgtgtcc      60
cgtagttgag tctgagtgct                                                80

<210> SEQ ID NO 23
<211> LENGTH: 80
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
gtgacgactg acatatctgc tgtggtggtg ggggagggtg gtggggtggc cggcgctcgt     60
cgtagttgag tctgagtgct                                                80

<210> SEQ ID NO 24
<211> LENGTH: 80
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
gtgacgactg acatatctgc tgggttacgt ggttcggggc tagggggtg gggtgtgttt      60 cgtagttgag tctgagtgct                                                80

<210> SEQ ID NO 25
<211> LENGTH: 80
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
gtgacgactg acatatctgc tggtggtgtg cggtgggttc ttgggtggga tgggtggtac     60
cgtagttgag tctgagtgct                                                80

<210> SEQ ID NO 26
<211> LENGTH: 80
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
gtgacgactg acatatctgc tattagatcc tcggtgggtg ggtgggtgtg tggtggtgtg     60
cgtagttgag tctgagtgct                                                        80

<210> SEQ ID NO 27
<211> LENGTH: 80
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
gtgacgactg acatatctgc gggcgtctga gcgcatggat gacccaccga cagattgcgg           60
cgtagttgag tctgagtgct                                                        80

<210> SEQ ID NO 28
<211> LENGTH: 80
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
gtgacgactg acatatctgc gctttgggtg ggctcggtgt gcggtgtgcg ggtgggtttg           60
cgtagttgag tctgagtgct                                                        80

<210> SEQ ID NO 29
<211> LENGTH: 80
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
gtgacgactg acatatctgc gtttggggtt ggggcctggg agtttgggga gcagaaaggg           60
cgtagttgag tctgagtgct                                                        80

<210> SEQ ID NO 30
<211> LENGTH: 80
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
gtgacgactg acatatctgc gggtgggttg ggttgggttt ggtggtggtg cctgttagtt           60
cgtagttgag tctgagtgct                                                        80

<210> SEQ ID NO 31
<211> LENGTH: 80
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
gtgacgactg acatatctgc aggtgggtgg gtgggtgtgt gtgcggtggt gtgatttggc           60
cgtagttgag tctgagtgct                                                        80

```
<210> SEQ ID NO 32
<211> LENGTH: 80
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
gtgacgactg acatatctgc tgtggttggt gggggcggc gggtggggag cctggtgttc    60
cgtagttgag tctgagtgct                                               80

<210> SEQ ID NO 33
<211> LENGTH: 80
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
gtgacgactg acatatctgc tcccgtttga gggcttgtcg acagattgc tggcacgtca    60 cgtagttgag tctgagtgct                                               80

<210> SEQ ID NO 34
<211> LENGTH: 80
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
gtgacgactg acatatctgc tcttggtggt ggtggtgggt tgggatgggt cttgggctgc    60
cgtagttgag tctgagtgct                                               80

<210> SEQ ID NO 35
<211> LENGTH: 80
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35
gtgacgactg acatatctgc ctgtgagggg agggagggtg ggtttggcgg tggcgcaggc    60
cgtagttgag tctgagtgct                                               80

<210> SEQ ID NO 36
<211> LENGTH: 80
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36
gtgacgactg acatatctgc gtggtggtgc gtgggtggtg ggggggggag ctgggtgccc    60
cgtagttgag tctgagtgct                                               80

<210> SEQ ID NO 37
<211> LENGTH: 80
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 37
gtgacgactg acatatctgc tgtgggtgtt gtggggtgg gtggtgggcc cttcgccgtg     60
cgtagttgag tctgagtgct                                                80

<210> SEQ ID NO 38
<211> LENGTH: 80
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38
gtgacgactg acatatctgc ttccggtatg tgtgggtggg tgggtggtgt ggtggtgttg     60
cgtagttgag tctgagtgct                                                80

<210> SEQ ID NO 39
<211> LENGTH: 80
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39
gtgacgactg acatatctgc tctcttctgt tgtgggtggg tgggtggtgt ggtgcgtgtg     60
cgtagttgag tctgagtgct                                                80

<210> SEQ ID NO 40
<211> LENGTH: 80
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40
gtgacgactg acatatctgc ggctgggtgg gttgggttag ggtggtgtgc ggtgggttgc     60
cgtagttgag tctgagtgct                                                80

<210> SEQ ID NO 41
<211> LENGTH: 80
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41
gtgacgactg acatatctgc gtttaggtgg gcgggtgggt gtgcggtggg cggtgttgaa     60
cgtagttgag tctgagtgct                                                80

<210> SEQ ID NO 42
<211> LENGTH: 80
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 42
gtgacgactg acatatctgc ggtgattggg gttggggcct gggcgtttgg ggaccgcatg    60
cgtagttgag tctgagtgct                                                80

<210> SEQ ID NO 43
<211> LENGTH: 80
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43
gtgacgactg acatatctgc gtttggggtt ggggcctggg agtttgggga gcagagagga    60
cgtagttgag tctgagtgct                                                80

<210> SEQ ID NO 44
<211> LENGTH: 80
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44
gtgacgactg acatatctgc taacttgttg gggtttgggg cctgggtgtt ggggttgttt    60
cgtagttgag tctgagtgct                                                80

<210> SEQ ID NO 45
<211> LENGTH: 80
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45
gtgacgactg acatatctgc tgggttggt gggggaggt gggtgggtta tgtgcgctgg    60
cgtagttgag tctgagtgct                                                80

<210> SEQ ID NO 46
<211> LENGTH: 80
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 46
gtgacgactg acatatctgc tgtgggtgtt gtggggtgg gttggtgggc attgcgtgtg    60
cgtagttgag tctgagtgct                                                80

<210> SEQ ID NO 47
<211> LENGTH: 80
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47
gtgacgactg acatatctgc gagtgggttc ggtggtggtg tgtgggaggg ttgggtacgt    60
```

<210> SEQ ID NO 48
<211> LENGTH: 80
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 48
gtgacgactg acatatctgc tggacatgat tgcaccgtat gaggtttagt cgttaatgtg    60
cgtagttgag tctgagtgct                                               80

<210> SEQ ID NO 49
<211> LENGTH: 80
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 49
gtgacgactg acatatctgc agtggggcct gggcgttggg gtttggggtg cctcgtcagt    60
cgtagttgag tctgagtgct                                               80

<210> SEQ ID NO 50
<211> LENGTH: 80
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 50
gtgacgactg acatatctgc atggattttc ggtgggtggg tgggttggtg tggtggtgtg    60
cgtagttgag tctgagtgct                                               80

<210> SEQ ID NO 51
<211> LENGTH: 80
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 51
gtgacgactg acatatctgc tgtggttggt ggggggtggg tggtgggaag gttccggtgc    60
cgtagttgag tctgagtgct                                               80

<210> SEQ ID NO 52
<211> LENGTH: 80
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 52
gtgacgactg acatatctgc ggttgggggtt ggggcctggg tgttggggag caggtagcac    60
cgtagttgag tctgagtgct                                               80

<210> SEQ ID NO 53

```
<211> LENGTH: 80
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 53
gtgacgactg acatatctgc ggcctgggag ggttcggtgg tggtgcgagg gtgggcaagc      60
cgtagttgag tctgagtgct                                                 80

<210> SEQ ID NO 54
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 54
acctagtttg gcttgcauaa gtaacuagca cgtgggctag                            40

<210> SEQ ID NO 55
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 55
acgatcgccc cugtctutaa gaucgaatac tatgggctag                            40

<210> SEQ ID NO 56
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 56
acctagaaag gcttagtgaa gtaaugatca gggcgggatc                            40

<210> SEQ ID NO 57
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 57
acctagttcc cugtctauua gauccgagug tatgccgatc                            40

<210> SEQ ID NO 58
```

```
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 58
acctaggcag tcttgccgaa tttacgagug gggagggatc                              40

<210> SEQ ID NO 59
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 59
acgatcactg cucagcutua ttaacuagcu tcgaccctag                              40

<210> SEQ ID NO 60
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 60
acgatcttcc gccagctgua ttucgaagug cgtgaggatc                              40

<210> SEQ ID NO 61
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 61
acctaggcgg tcttuccgtc gttacgtccu cggcccctag                              40

<210> SEQ ID NO 62
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 62
acctagtttg gcgtagcgua ttaaugggug cggcagctag                              40
```

<210> SEQ ID NO 63
<211> LENGTH: 40
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 63
acgatcgctg acgtucauua gtatgaggca cgtgggctag                                40

<210> SEQ ID NO 64
<211> LENGTH: 41
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 64
tcttaatacg actcactata gggagtgtgt acgaggcatt a                              41

<210> SEQ ID NO 65
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 65
gcttctaggg cgatcaagta tca                                                  23

<210> SEQ ID NO 66

<400> SEQUENCE: 66

000

<210> SEQ ID NO 67
<211> LENGTH: 80
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (21)..(60)
<223> OTHER INFORMATION: a, c, t or g

<400> SEQUENCE: 67
gtgacgactg acatatctgc nnnnnnnnnn nnnnnnnnnn nnnnnnnnnn nnnnnnnnnn          60
cgtagttgag tctgagtgct                                                     80

<210> SEQ ID NO 68
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 68
gtgacgactg acatatctgc                                                     20

<210> SEQ ID NO 69
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 69
agcactcaga ctcaactacg                                              20

<210> SEQ ID NO 70
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 70
aaaaaaaaaa aaaaaaaaaa                                              20

<210> SEQ ID NO 71
<211> LENGTH: 222
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 71

Glu Val Gln Leu Val Gln Ser Gly Pro Glu Leu Lys Lys Pro Gly Ala
1               5                   10                  15

Ser Val Lys Val Ser Cys Lys Ala Ser Gly Tyr Thr Phe Thr Asn Tyr
            20                  25                  30

Gly Met Asn Trp Val Arg Gln Ala Pro Gly Gln Gly Leu Glu Trp Met
        35                  40                  45

Gly Trp Ile Asn Thr Tyr Thr Gly Glu Thr Tyr Ala Asp Asp Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Glu Arg Gly Gly Val Asn Asn Trp Gly Gln Gly Thr Leu Val Thr Val
            100                 105                 110

Ser Ser Ala Ser Thr Lys Gly Pro Ser Val Phe Pro Leu Ala Pro Ser
        115                 120                 125

Ser Lys Ser Thr Ser Gly Gly Thr Ala Ala Leu Gly Cys Leu Val Lys
    130                 135                 140

Asp Tyr Phe Pro Glu Pro Val Thr Val Ser Trp Asn Ser Gly Ala Leu
145                 150                 155                 160

Thr Ser Gly Val His Thr Phe Pro Ala Val Leu Gln Ser Ser Gly Leu
                165                 170                 175

Tyr Ser Leu Ser Ser Val Val Thr Val Pro Ser Ser Ser Leu Gly Thr
            180                 185                 190

Gln Thr Tyr Ile Cys Asn Val Asn His Lys Pro Ser Asn Thr Lys Val
        195                 200                 205

Asp Lys Lys Val Glu Pro Lys Ser Cys Asp Lys Thr His Thr
    210                 215                 220

<210> SEQ ID NO 72
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 72

Asp Ile Gln Val Thr Gln Ser Pro Ser Ser Leu Ser Ala Ser Val Gly
1               5                   10                  15

Asp Arg Val Thr Ile Thr Cys Ile Thr Ser Thr Asp Ile Asp Asp Asp
            20                  25                  30

Met Asn Trp Tyr Gln Gln Lys Pro Gly Lys Val Pro Lys Leu Leu Ile
        35                  40                  45

Ser Gly Gly Asn Thr Leu Arg Pro Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Leu Gln Ser Asp Ser Leu Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 73
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 73
acggagaaag agagagtgta attgctagca taaccgctgc                            40

<210> SEQ ID NO 74
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 74
gtaaccacgt tgccagaccg agtctaccag cgatcctcag                            40

<210> SEQ ID NO 75
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 75
tatgcccaaa tccctcaagt cggccaggat acaccaccgt                              40

<210> SEQ ID NO 76
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 76
aatcaaaagg ctcacgcgcg gattggtcaa ccttacaacc                              40

<210> SEQ ID NO 77
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 77
tcggccttcc cagaccaccg caatccccag ggaacaggca                              40

<210> SEQ ID NO 78
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 78
catcacactg tcaacatacc cagcctgggg aaagacgaac                              40

<210> SEQ ID NO 79
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 79
aacccgcatg ccgatcgatg tcgtgcctcg ctccacgctc                              40

<210> SEQ ID NO 80
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 80
accaggcacc cgacggacta actcatcact caggcgaggg                              40

<210> SEQ ID NO 81
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 81
ucatgccatt actcucgact gugccugaat                                          30

<210> SEQ ID NO 82
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 82
cctgugagcc tgatcgagac atgtcggaag                                          30

<210> SEQ ID NO 83
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 83
gtctaccttc tauaaagggt cctctttacu                                          30

<210> SEQ ID NO 84
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 84
caggtttggu ctugtattgc cgauugccca                                          30

<210> SEQ ID NO 85
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 85

Glu Val Gln Leu Val Gln Ser Gly Pro Glu Leu Lys Lys Pro Gly Ala
1               5                   10                  15

Ser Val Lys Val Ser Cys Lys Ala Ser Gly Tyr Thr Phe Thr Asn Tyr

Gly Met Asn Trp Val Arg Gln Ala Pro Gly Gln Gly Leu Glu Trp Met
            35                  40                  45

Gly Trp Ile Asn Thr Tyr Thr Gly Glu Thr Thr Tyr Ala Glu Asp Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Glu Arg Glu Gly Gly Val Asn Asn Trp Gly Gln Gly Thr Leu Val Thr
                100                 105                 110

Val Ser Ser
        115

<210> SEQ ID NO 86
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 86

Glu Val Gln Leu Val Gln Ser Gly Pro Glu Leu Lys Lys Pro Gly Ala
1               5                   10                  15

Ser Val Lys Val Ser Cys Lys Ala Ser Gly Tyr Thr Phe Thr Asn Tyr
                20                  25                  30

Gly Met Asn Trp Val Arg Gln Ala Pro Gly Gln Gly Leu Glu Trp Met
            35                  40                  45

Gly Trp Ile Asn Thr Tyr Thr Gly Glu Thr Thr Tyr Ala Glu Asp Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Glu Arg Glu Gly Gly Val Ser Asn Trp Gly Gln Gly Thr Leu Val Thr
                100                 105                 110

Val Ser Ser
        115

<210> SEQ ID NO 87
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 87

Asp Ile Gln Val Thr Gln Ser Pro Ser Ser Leu Ser Ala Ser Val Gly
1               5                   10                  15

Asp Arg Val Thr Ile Thr Cys Ile Thr Ser Thr Asp Ile Glu Ser Asp
                20                  25                  30

Met Asn Trp Tyr Gln Gln Lys Pro Gly Lys Val Pro Lys Leu Leu Ile
            35                  40                  45

Ser Gly Gly Asn Thr Leu Arg Pro Gly Val Pro Ser Arg Phe Ser Gly
    50                  55                  60

Ser Gly Ser Gly Thr Asp Phe Thr Leu Thr Ile Ser Ser Leu Gln Pro

```
                65                  70                  75                  80
Glu Asp Val Ala Thr Tyr Tyr Cys Leu Gln Ser Asp Ser Leu Pro Tyr
                    85                  90                  95

Thr Phe Gly Gln Gly Thr Lys Val Glu Ile Lys
                100                 105

<210> SEQ ID NO 88
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 88

Asp Ile Gln Val Thr Gln Ser Pro Ser Ser Leu Ser Ala Ser Val Gly
1               5                   10                  15

Asp Arg Val Thr Ile Thr Cys Ile Thr Ser Thr Asp Ile Glu Ser Asp
                20                  25                  30

Met Asn Trp Tyr Gln Gln Lys Pro Gly Lys Val Pro Lys Leu Leu Ile
                35                  40                  45

Ser Gly Gly Asn Thr Leu Arg Pro Gly Val Pro Ser Arg Phe Ser Gly
            50                  55                  60

Ser Gly Ser Gly Thr Asp Phe Thr Leu Thr Ile Ser Ser Leu Gln Pro
65              70                  75                  80

Glu Asp Val Ala Thr Tyr Tyr Cys Leu Gln Ser Glu Ser Leu Pro Tyr
                85                  90                  95

Thr Phe Gly Gln Gly Thr Lys Val Glu Ile Lys
                100                 105

<210> SEQ ID NO 89
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 89

Asp Ile Gln Val Thr Gln Ser Pro Ser Ser Leu Ser Ala Ser Val Gly
1               5                   10                  15

Asp Arg Val Thr Ile Thr Cys Ile Thr Ser Thr Ser Ile Glu Ser Asp
                20                  25                  30

Met Asn Trp Tyr Gln Gln Lys Pro Gly Lys Val Pro Lys Leu Leu Ile
                35                  40                  45

Ser Gly Gly Asn Thr Leu Arg Pro Gly Val Pro Ser Arg Phe Ser Gly
            50                  55                  60

Ser Gly Ser Gly Thr Asp Phe Thr Leu Thr Ile Ser Ser Leu Gln Pro
65              70                  75                  80

Glu Asp Val Ala Thr Tyr Tyr Cys Leu Gln Ser Asp Ser Leu Pro Tyr
                85                  90                  95

Thr Phe Gly Gln Gly Thr Lys Val Glu Ile Lys
                100                 105

<210> SEQ ID NO 90
<211> LENGTH: 8
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 90

Arg Arg Arg Arg Arg Arg Arg Arg
1               5

<210> SEQ ID NO 91
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 91
agcactcaga ctcaactacg                                                    20

<210> SEQ ID NO 92
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 92

His His His His His His
1               5

<210> SEQ ID NO 93
<211> LENGTH: 89
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (29)..(58)
<223> OTHER INFORMATION: a, c, t, g, unknown or other

<400> SEQUENCE: 93
gggagtgtgt acgaggcatt aggccgccnn nnnnnnnnnn nnnnnnnnnn nnnnnnnngg        60
cggctttgat acttgatcgc cctagaagc                                          89

<210> SEQ ID NO 94
<211> LENGTH: 228
<212> TYPE: PRT
<213> ORGANISM: Homo sapiens

<400> SEQUENCE: 94

Ile Leu Gly Gly Arg Glu Ala Glu Ala His Ala Arg Pro Tyr Met Ala
1               5                   10                  15

Ser Val Gln Leu Asn Gly Ala His Leu Cys Gly Gly Val Leu Val Ala
                20                  25                  30

Glu Gln Trp Val Leu Ser Ala Ala His Cys Leu Glu Asp Ala Ala Asp
            35                  40                  45

Gly Lys Val Gln Val Leu Leu Gly Ala His Ser Leu Ser Gln Pro Glu
        50                  55                  60

Pro Ser Lys Arg Leu Tyr Asp Val Leu Arg Ala Val Pro His Pro Asp
65                  70                  75                  80

Ser Gln Pro Asp Thr Ile Asp His Asp Leu Leu Leu Leu Gln Leu Ser
                85                  90                  95

```
Glu Lys Ala Thr Leu Gly Pro Ala Val Arg Pro Leu Pro Trp Gln Arg
            100                 105                 110

Val Asp Arg Asp Val Ala Pro Gly Thr Leu Cys Asp Val Ala Gly Trp
            115                 120                 125

Gly Ile Val Asn His Ala Gly Arg Arg Pro Asp Ser Leu Gln His Val
            130                 135                 140

Leu Leu Pro Val Leu Asp Arg Ala Thr Cys Asn Arg Arg Thr His His
145                 150                 155                 160

Asp Gly Ala Ile Thr Glu Arg Leu Met Cys Ala Glu Ser Asn Arg Arg
                165                 170                 175

Asp Ser Cys Lys Gly Asp Ser Gly Gly Pro Leu Val Cys Gly Gly Val
            180                 185                 190

Leu Glu Gly Val Val Thr Ser Gly Ser Arg Val Cys Gly Asn Arg Lys
            195                 200                 205

Lys Pro Gly Ile Tyr Thr Arg Val Ala Ser Tyr Ala Ala Trp Ile Asp
            210                 215                 220

Ser Val Leu Ala
225

<210> SEQ ID NO 95
<211> LENGTH: 89
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (29)..(58)
<223> OTHER INFORMATION: a, c, u, g, unknown or other

<400> SEQUENCE: 95
gggagugugu acgaggcauu aggccgccnn nnnnnnnnnn nnnnnnnnnn nnnnnnnngg      60
cggcuuugau acuugaucgc ccuagaagc                                       89
```